US012180399B2

(12) United States Patent
Kakizoe et al.

(10) Patent No.: US 12,180,399 B2
(45) Date of Patent: Dec. 31, 2024

(54) COMPOSITION, FILM, ORGANIC LIGHT EMITTING ELEMENT, METHOD FOR PROVIDING LIGHT EMITTING COMPOSITION, AND PROGRAM

(71) Applicant: KYULUX, INC., Fukuoka (JP)

(72) Inventors: Hayato Kakizoe, Fukuoka (JP); Hiroaki Ozawa, Fukuoka (JP); Ayataka Endo, Fukuoka (JP); YuSeok Yang, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 135 days.

(21) Appl. No.: 17/760,072

(22) PCT Filed: Feb. 3, 2021

(86) PCT No.: PCT/JP2021/003826
§ 371 (c)(1),
(2) Date: Aug. 3, 2022

(87) PCT Pub. No.: WO2021/157593
PCT Pub. Date: Aug. 12, 2021

(65) Prior Publication Data
US 2023/0119624 A1    Apr. 20, 2023

(30) Foreign Application Priority Data

Feb. 4, 2020 (JP) .................................. 2020-017201
May 22, 2020 (JP) .................................. 2020-090095
Sep. 1, 2020 (JP) .................................. 2020-147167

(51) Int. Cl.
*C09K 11/02* (2006.01)
*C07D 405/10* (2006.01)
(Continued)

(52) U.S. Cl.
CPC ............. *C09K 11/02* (2013.01); *C07D 405/10* (2013.01); *C07D 409/14* (2013.01);
(Continued)

(58) Field of Classification Search
CPC ...................................................... C09K 11/02
See application file for complete search history.

(56) References Cited

U.S. PATENT DOCUMENTS

2019/0181353 A1    6/2019   Ihn
2019/0341571 A1*  11/2019   Liaptsis ................. H10K 50/12

FOREIGN PATENT DOCUMENTS

CN        110498790 A    11/2019
EP         3522248 A1     8/2019
(Continued)

OTHER PUBLICATIONS

Japanese and English version of International Preliminary Report on Patentability of Chapter I, i.e., International Search Opinion which we received from the WIPO as the International Bureau of the PCT issued in International Application No. PCT/JP2021/003826 (Jul. 28, 2022).

(Continued)

*Primary Examiner* — William D Young
(74) *Attorney, Agent, or Firm* — FISHERBROYLES, LLP; Roger L. Browdy

(57) ABSTRACT

An organic light emitting element produced by using a light emitting composition that contains both a first compound having a PBHT value more than 0.730 and a second compound having $E_{S1}$ lower than that of the first compound and $\Delta E_{ST}$ less than 0.20 eV is excellent in durability. $E_{S1}$ is the lowest excited singlet energy level, $\Delta E_{ST}$ is the difference between the lowest excited singlet energy level and the lowest excited triplet energy level.

27 Claims, 2 Drawing Sheets

(51) Int. Cl.
- C07D 409/14 (2006.01)
- C07D 491/048 (2006.01)
- C07D 491/153 (2006.01)
- C09K 11/06 (2006.01)
- H10K 50/11 (2023.01)
- H10K 85/60 (2023.01)

(52) U.S. Cl.
CPC ..... *C07D 491/048* (2013.01); *C07D 491/153* (2013.01); *C09K 11/06* (2013.01); *H10K 85/654* (2023.02); *H10K 85/657* (2023.02); *H10K 85/6574* (2023.02); *H10K 85/6576* (2023.02); *C09K 2211/1007* (2013.01); *C09K 2211/1018* (2013.01); *H10K 50/11* (2023.02)

(56) References Cited

FOREIGN PATENT DOCUMENTS

| | | |
|---|---|---|
| JP | 2014-043541 A | 3/2014 |
| JP | 2018-501354 A | 1/2018 |
| JP | 2018-061028 A | 4/2018 |
| JP | 2018-061030 A | 4/2018 |
| JP | 2019-023183 A | 2/2019 |
| JP | 2019-204947 A | 11/2019 |
| KR | 10-2019-0027343 A | 3/2019 |
| KR | 10-2018-0138422 A | 6/2019 |
| KR | 10-2019-0064009 A | 6/2019 |
| WO | 2016/017760 A1 | 2/2016 |
| WO | 2016/181846 A1 | 11/2016 |
| WO | 2019/235402 A1 | 12/2019 |

OTHER PUBLICATIONS

International Search Report and Search Opinion issued in International Application No. PCT/JP2021/003826 (Apr. 13, 2021).
Li et al., Design principles of carbazole/dibenzothiophene derivatives as host material in modern efficent organic light-emitting diodes, Journal of Materials Chemistry C, 2017, vol. 5, 6989-6996.
H. Uoyama, et al., Highly efficient organic light-emitting diodes from delayed fluorescence, Nature 492, 234, 2012.
H. Nakanotani, et al., Promising operational stability of high-efficiency organic light-emitting diodes based on thermally activated delayed fluorescence, Scientific Reports, 3, 2127, 2013.
Extended European Search Report dated Jul. 4, 2023 issued in the corresponding European patent application No. 21750170.9.
Japanese Office Action dated Aug. 6, 2024, in corresponding Japanese patent application No. 2021-575819.

* cited by examiner

[FIG. 1]
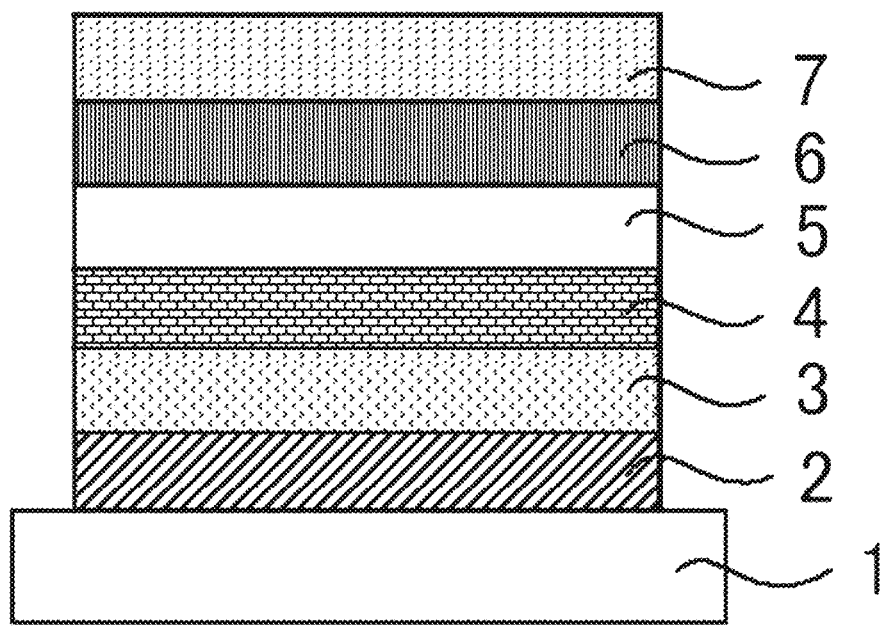
[FIG. 2]
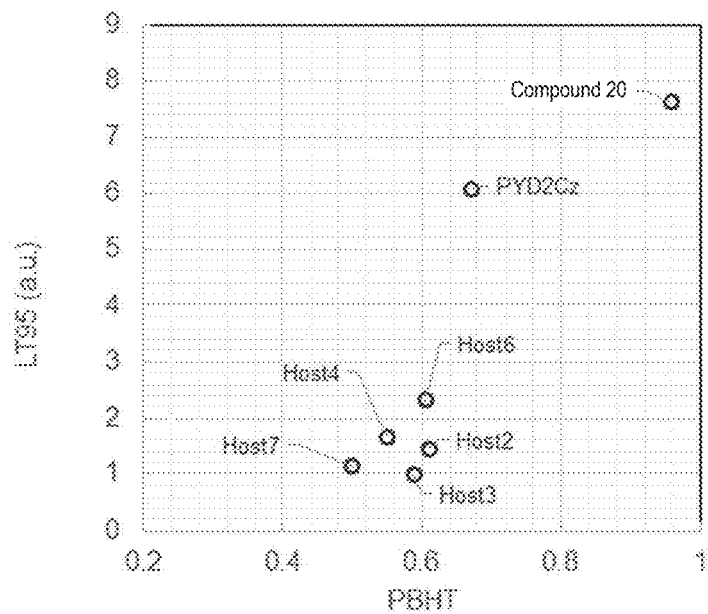

[FIG. 3]
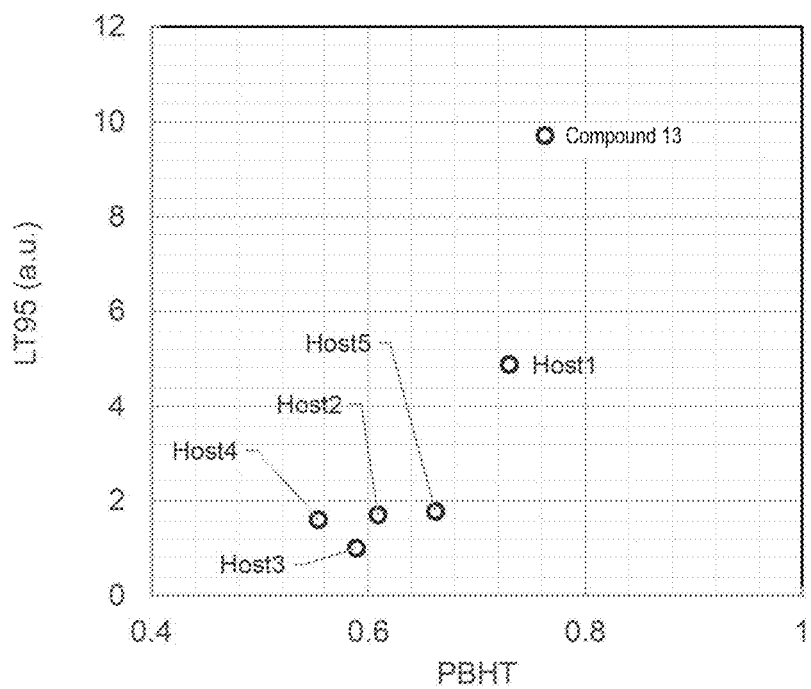

COMPOSITION, FILM, ORGANIC LIGHT EMITTING ELEMENT, METHOD FOR PROVIDING LIGHT EMITTING COMPOSITION, AND PROGRAM

FIELD OF INVENTION

The present invention relates to a composition having excellent luminescent characteristics, and a film and an organic light emitting element that are produced by using the composition. The present invention also relates to a method for providing a light emitting composition and a program that executes the method.

BACKGROUND OF ART

Studies are being actively made for enhancing the luminous efficiency of a light emitting element, such as an organic electroluminescence element (organic EL element). Various ideas have been devised for enhancing the luminous efficiency particularly by newly developing and combining an electron transporting material, a hole transporting material, a light emitting material, and the like which constitute an organic electroluminescence element. Among them, there are seen studies about an organic electroluminescence element in which a delayed fluorescent material is used.

A delayed fluorescent material is a compound that emits fluorescence in returning from the excited singlet state to the ground state after the reverse intersystem crossing from the excited triplet state to the excited singlet state in the excited state. The fluorescence emitted through such a course is observed later than the fluorescence from the excited singlet state that occurs directly from the ground state (normal fluorescence), and thus is referred to as delayed fluorescence. Here, for example, when a light emitting compound is exited by injecting a carrier, the statistical generation probability of the excited singlet state and the excited triplet state is 25%:75%. Accordingly, the increase in luminous efficiency is limited only with the fluorescence from the excited singlet state occurring directly. On the other hand, in a delayed fluorescent material, not only the excited singlet state but also the excited triplet state can be used for fluorescence emission through the course via the reverse intersystem crossing, and thus, a higher luminous efficiency is achieved as compared with a normal delayed fluorescent material.

As such a delayed fluorescent material. PTL 1 proposes a benzene derivative having a heteroaryl group, such as a carbazolyl group, or a diphenylamino group and at least two cyano groups, and confirms that an organic EL element produced by using the benzene derivative in a light emitting layer provided a high luminous efficiency.

NPL 1 reports that a carbazolyl dicyanobenzene derivative represented by the following formula (hereinafter referred to as "4CzIPN") is a thermally activated delayed fluorescent material, and that an organic electroluminescence element produced by using 4CzIPN achieved a high internal EL quantum efficiency. NPL 2 reports that optimization of the structure of an organic electroluminescence element produced by using 4CzIPN led to achievement of a high luminous efficiency and high durability.

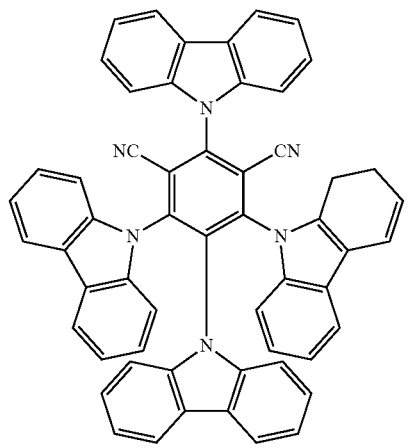

4CzIPN

CITATION LIST

Patent Literature

PTL 1: JP-A-2014-43541

Non-Patent Literature

NPL 1: H. Uoyama, et al., Nature 492, 234 (2012)
NPL 2: H. Nakanotani, et al., Scientific Reports, 3, 2127 (2013)

SUMMARY OF INVENTION

Technical Problem

As described above, the studies so far have been made mainly for the purpose of improving the characteristics of a light emitting element by finding a compound useful as a delayed fluorescent material or optimizing the structure of a light emitting element produced by using a delayed fluorescent material. Thus, many compounds are proposed as a delayed fluorescent material today, and many improvements are proposed in the structure of a light emitting element. On the other hand, when a light emitting element is produced by using a delayed fluorescent material, a film is formed by combining the delayed fluorescent material with a host material, and the host material to be combined here is currently selected through trial and error.

In view of the problem in the current situation, the present inventors have intensively and extensively studied for the purpose of providing a useful index in selection of a host material to be combined with a delayed fluorescent material.

Solution to Problem

As a result of intensive and extensive studies for achieving the above purpose, the present inventors have found that an organic light emitting element having high durability can be provided by using a PBHT value. The present invention is proposed based on the finding, and specifically has the following configuration.

[1] A composition containing both a first compound satisfying the following expression (1a) and a second compound satisfying the following expression (2b), the first compound and the second compound satisfying the following expression (A):

PBHT(1)>0.730    expression (1a)

$\Delta E_{ST}(2)<0.20$ eV    expression (2b)

$E_{S1}(1)>E_{S1}(2)$    expression (A)

wherein PBHT(1) is a PBHT value of the first compound, $\Delta E_{ST}(2)$ is a difference between a lowest excited singlet energy level $E_{S1}(2)$ of the second compound and a lowest excited triplet energy level $E_T(2)$ of the second compound, and $E_{S1}(1)$ is a lowest excited singlet energy level of the first compound.

[2] The composition according to [1], wherein the first compound also satisfies the following expression (1c):

BDE(1)>4.20 eV    expression (1c)

wherein BDE(1) is a cation bond dissociation energy of the first compound.

[3] The composition according to [1], wherein the second compound also satisfies the following expression (2a):

0.200<PBHT(2)<0.400    expression (2a)

wherein PBHT(2) is a PBHT value of the second compound.
[4] The composition according to 111, wherein the first compound also satisfies the following expression (1c) and the second compound also satisfies the following expression (2a):

BDE(1)>4.20 eV    expression (1c)

0.200<PBHT(2)<0.400    expression (2a)

wherein BDE(1) is a cation bond dissociation energy of the first compound and PBHT(2) is a PBHT value of the second compound.
[5] The composition according to any one of [1] to [4], wherein the PBHT(1) is more than 0.910.
[6] The composition according to any one of [1] to [5], wherein the second compound satisfies the following expression (2d):

$\tau_{DELAY}<10$ μs    expression (2d)

wherein $\tau_{DELAY}$ is a delayed fluorescence lifetime of the second compound.
[7] The composition according to any one of [1] to [6], wherein the first compound has one or more structures selected from the group consisting of a triazine structure, a carbazole structure, a fulvalene structure, and a thiovalene structure.
[8] The composition according to any one of [1] to [7], wherein the first compound has at least one of a dibenzofuran structure or a dibenzothiophene structure.
[9] The composition according to [8], wherein the first compound has a structure represented by the following general formula (1):

General formula (1)

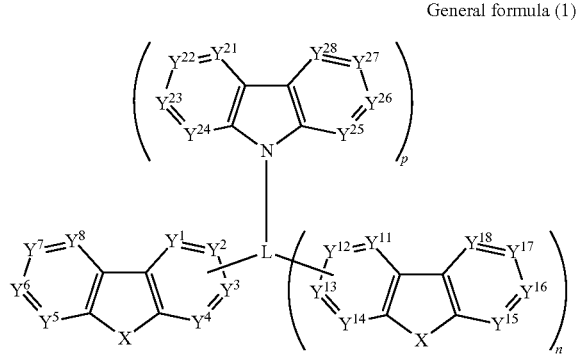

wherein multiple Xs each independently represent O or S, $Y^1$ to $Y^8$ and $Y^{11}$ to $Y^{18}$ each independently represent N or C—R wherein R represents a hydrogen atom, a substituent, or a direct bond to L, $Y^{21}$ to $Y^{28}$ each independently represent N or C—R$^1$ wherein R' represents a hydrogen atom or a substituent, L represents a (n+p+1)-valent conjugated linking group having at least one aromatic ring or heteroaromatic ring, n represents an integer of 0 or more, when n is 2 or more, multiple $Y^{11}$s to $Y^{18}$s may be the same as or different from each other, p represents an integer of 0 or more, when p is 2 or more, multiple $Y^{21}$s to $Y^{28}$s may be the same as or different from each other, and n+p is 1 or more.

[10] The composition according to [8], wherein the first compound has a structure represented by the following general formula (2):

General formula (2)

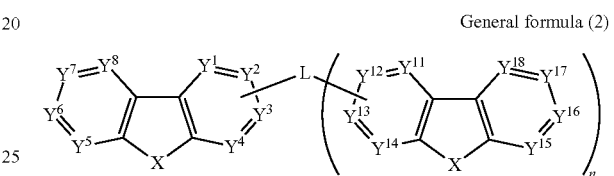

wherein multiple Xs each independently represent O or S, $Y^1$ to $Y^8$ and $Y^{11}$ to $Y^{18}$ each independently represent N or C—R wherein R represents a hydrogen atom, a substituent, or a direct bond to L, L represents a (n+1)-valent conjugated linking group containing at least one aromatic ring or heteroaromatic ring, n represents an integer of 1 or more, and when n is 2 or more, multiple $Y^{11}$s to $Y^{18}$s may be the same as or different from each other.

[11] The composition according to [8], wherein the first compound has a structure represented by the following general formula (3):

General formula (3)

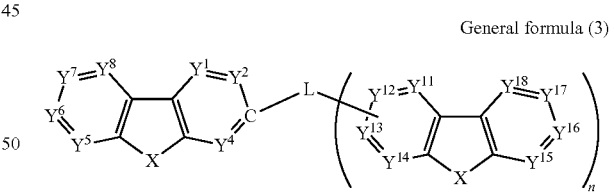

wherein multiple Xs each independently represent O or S, $Y^1, Y^2, {}^4$ to $Y^8$, and $Y^{11}$ to $Y^{18}$ each independently represent N or C—R wherein R represents a hydrogen atom, a substituent, or a direct bond to L, L represents a (n+1)-valent conjugated linking group containing at least one aromatic ring or heteroaromatic ring, n represents an integer of 2 or more, and multiple $Y^{11}$s to $Y^{18}$s may be the same as or different from each other.

[12] The composition according to [8], wherein the first compound has a structure represented by the following general formula (4):

General formula (4)

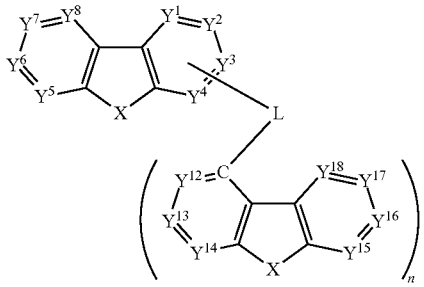

wherein multiple Xs each independently represent O or S, $Y^1$ to $Y^8$ and $Y^{12}$ to $Y^{18}$ each independently represent N or C—R wherein R represents a hydrogen atom, a substituent, or a direct bond to L, L represents a (n+1)-valent conjugated linking group containing at least one aromatic ring or heteroaromatic ring, n represents an integer of 2 or more, and multiple $Y^{12}$s to $Y^{18}$s may be the same as or different from each other.

[13] The composition according to [8], wherein the first compound has a structure represented by the following general formula (5):

General formula (5)

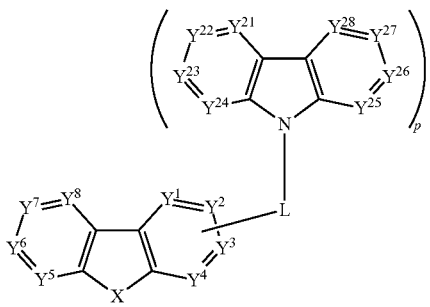

wherein X represents O or S, $Y^1$ to $Y^8$ each independently represent N or C—R wherein R represents a hydrogen atom, a substituent, or a direct bond to L, $Y^{21}$ to $Y^{28}$ each independently represent N or C—$R^1$ wherein $R^1$ represents a hydrogen atom or a substituent, L represents a (p+1)-valent conjugated linking group containing at least one aromatic ring or heteroaromatic ring, p represents an integer of 1 or more, and when p is 2 or more, multiple $Y^{21}$s to $Y^{28}$s may be the same as or different from each other.

[14] The composition according to any one of [9] to [13], wherein L has a structure having one or more rings linked, the rings being selected from the group consisting of a benzene ring and a pyridine ring.

[15] The composition according to any one of [9] to [13], wherein L contains a 1,3-phenylene group or a 2,6-pyridylene group as a linking chain.

[16] The composition according to any one of [9] to [13], wherein L contains a 1,4-phenylene group or a 2,6-pyridylene group as a linking chain.

[17] The composition according to any one of [9] to [12], wherein n is 2.

[18] The composition according to any one of [9] to [17], wherein R is a hydrogen atom or a substituted or unsubstituted aryl group.

[19] The composition according to any one of [1] to [18], wherein a content of the second compound is 0.01 to 70 parts by weight relative to 100 parts by weight of a content of the first compound.

[20] The composition according to any one of [1] to [19], further containing a third compound satisfying the following expression (B):

$$E_{S1}(1) > E_{S1}(2) > E_{S1}(3)$$ expression (B)

wherein $E_{S1}(3)$ is a lowest excited singlet energy level of the third compound.

[21] The composition according to [20], wherein the third compound also satisfies the following expression (3b).

$$\Delta E_{ST}(3) < 0.20 \text{ eV}$$ expression (3b)

wherein $\Delta E_{ST}(3)$ is a difference between the lowest excited singlet energy level $E_{S1}(3)$ of the third compound and a lowest excited triplet energy level $E_{T1}(3)$ of the third compound.

[22] Use of the composition according to any one of [1] to [21] as a light emitting composition.

[23] A film containing the composition according to any one of [1] to [21].

[24] Use of the film according to [23] as a light emitting film.

[25] An organic light emitting element containing the composition according to any one of [1] to [21].

[26] The organic light emitting element according to [25], which emits delayed fluorescence.

[27] The organic light emitting element according to [25] or [26], which is an organic electroluminescence element.

[28] The organic light emitting element according to any one of [25] to [27], wherein the second compound emits light in the largest amount of all materials contained in the light emitting element.

[29] The organic light emitting element according to any one of [26] to [28], wherein the composition is the composition according to [20] or [21] and the third compound emits light in the largest amount of all materials contained in the light emitting element.

[30] A method for providing a light emitting composition containing a first compound and a second compound, the method including designing the first compound to be combined with the second compound that has $\Delta E_{ST}(2)$ of less than 0.20 eV, the method also including designing the second compound so that $E_{S1}(1)$ is higher than $E_{S1}(2)$ and PBHT(l) is more than 0.730.

[31] The method according to [30], wherein the method includes designing the first compound so that PBHT(1) is large.

[32] The method according to [31], wherein the method includes selecting a compound having a larger PBHT(1) from multiple candidate compounds and adopting the compound as the first compound.

[33] A program that executes the method according to any one of [30] to [32].

Advantageous Effects of Invention

When the composition of the present invention is used, an organic light emitting element having excellent durability can be provided. According to the method of the present invention, a composition useful for producing an organic light emitting element having excellent durability can be conveniently designed.

BRIEF DESCRIPTION OF DRAWINGS

FIG. 1 is a schematic cross section illustrating a layer configuration of an organic electroluminescence element.

FIG. 2 is a graph showing a relation between the PBHT value of a first compound and the measurement result of LT95.

FIG. 3 is a graph showing a relation between the PBHT value of a first compound and the measurement result of LT95.

DESCRIPTION OF EMBODIMENTS

The present invention will be described in detail below. The constitutional requirements mentioned below may be described based on a typical embodiment or a specific example of the present invention, but the present invention is not specifically limited to the embodiment or specific example. A numerical range represented with "to" in this description means a range including the numerical values written before and after "to" as the lower limit and the upper limit. The species of isotope of hydrogen atom present in a molecule of a compound used in the present invention is not particularly limited, and, for example, all the hydrogen atoms in the molecule may be H, or a part or all thereof may be $^2$H (deuterium D).

(First Compound)

The first compound is a compound having a PBHT value more than 0.730. The PBHT value is a value proposed by Michael J. Peach, Peter Benfield, Trygve Helgaker, and David J. Tozer, and is named by arranging the initial letters of the family names of the four persons. The PBHT value is a numerical value that represents a property of an orbit in an excited state. There are a singlet PBHT value and a triplet PBHT value, and the present invention adopts the triplet PBHT value. A smaller PBHT value means that the excited state has a charge transfer property (CT property), and a larger PBHT value means that the excited state has a localized electronic property (LE property). The PBHT value is a value $\Lambda$ calculated by the following expression.

$$\Lambda = \frac{\sum_{k,a} \kappa_{ia}^2 O_{ia}}{\sum_{k,a} \kappa_{ia}^2}$$

In the expression, the definition of each member is as follows.

$$O_{ia} = \langle |\varphi_i||\varphi_a| \rangle = \int |\varphi_i(r)||\varphi_a(r)|dr$$

$\varphi_i$: Occupied orbit $\varphi_a$: Virtual orbit $$\begin{pmatrix} A & B \\ B & A \end{pmatrix}\begin{pmatrix} X \\ Y \end{pmatrix} = \omega \begin{pmatrix} 1 & 0 \\ 0 & -1 \end{pmatrix}\begin{pmatrix} X \\ Y \end{pmatrix}$$

$\kappa_{ia} = X_{ia} + Y_{ia}$

The method of calculating the PBHT value is described in detail in J. Chem. Phys. 128, 044118 (2008) "Excitation energies in density functional theory: An evaluation and a diagnostic test", and all the pages of the article is incorporated herein as a part of this description.

The first compound has a PBHT value preferably more than 0.730, preferably more than 0.750, preferably more than 0.800, preferably more than 0.830, preferably more than 0.850, preferably more than 0.900, preferably more than 0.920, preferably more than 0.950, preferably more than 0.980, and preferably more than 0.990.

The first compound is preferably a compound having a cation bond dissociation energy BDE(1) more than 4.20 eV. The cation bond dissociation energy BDE(1) is preferably more than 4.40 eV, preferably more than 4.60 eV, preferably more than 4.80 eV preferably more than 5.00 eV, preferably more than 5.20 eV, preferably more than 5.40 eV, preferably more than 5.60 eV, preferably more than 5.80 eV, preferably more than 6.00 eV, and preferably more than 6.10 eV.

The cation bond dissociation energy can be determined by calculation using b3lyp/6-31gs.

As the first compound, for example, a compound having a PBHT value more than 0.80 and a cation bond dissociation energy more than 4.30 eV can be preferably selected. A compound having a PBHT value more than 0.82 and a cation bond dissociation energy more than 4.35 eV can also be preferably selected. A compound having a PBHT value more than 0.85 and a cation bond dissociation energy more than 4.30 eV can also be preferably selected.

Furthermore, as the first compound, for example, a compound having a PBHT value more than 0.91 and a cation bond dissociation energy more than 4.30 eV can be preferably selected. A compound having a PBHT value more than 0.91 and a cation bond dissociation energy of more than 4.35 eV can also be preferably selected. A compound having a PBHT value more than 0.95 and a cation bond dissociation energy more than 4.30 eV can also be preferably selected.

The structure of the first compound is not particularly limited as long as it satisfies the expression (1a). A preferred first compound has one or more structures selected from the group consisting of a triazine structure, a carbazole structure, a fulvalene structure, and a thiovalene structure. The first compound may have two or more of the structures, and when having two or more, the structures may be the same as or different from each other. A more preferred first compound has at least one of a dibenzofuran structure and a dibenzothiophene structure. The first compound may have two or more dibenzofuran structures, may have two or more dibenzothiophene structures, or may have both a dibenzofuran structure and a dibenzothiophene structure.

As a preferred first compound, a compound having a structure represented by the following general formula (1) can be mentioned.

General formula (1)

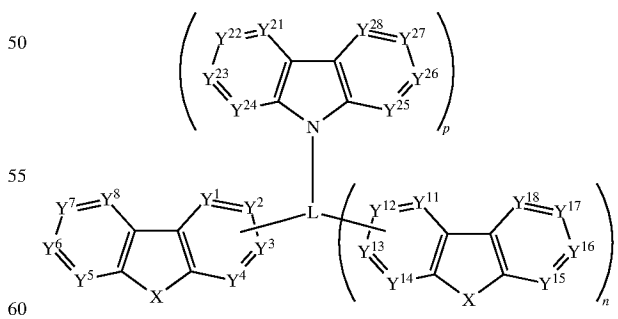

In the general formula (1), multiple Xs each independently represent O or S. All Xs present in the compound may be O or may be S. or both O and S may be present. As a preferred compound, a compound represented by the general formula (1) in which the n Xs constituting the tricyclic structure on the right side are all O can be mentioned. As a preferred compound, a compound represented by the general formula (1) in which the n Xs constituting the tricyclic structure on the right side are all S can be mentioned.

In the general formula (1), n represents an integer of 0 or more, p represents an integer of 0 or more. n+p is 1 or more. When n is 2 or more, multiple $Y^{11}$s to $Y^{18}$s may be the same as or different from each other. When p is 2 or more, multiple $Y^{21}$s to $Y^{28}$s may be the same as or different from each other.

As a preferred compound, a compound in which n is 2 or more can be mentioned, and as a more preferred compound, a compound in which n is 2 can be mentioned. In this case, p is preferably any integer of 0 to 2, and a compound in which p is 0 and a compound in which p is 1 can be mentioned. When n is 2 or more, a compound in which the n $Y^{11}$s are all the same, the n $Y^{12}$s are all the same, the n $Y^{13}$s are all the same, the n $Y^{14}$s are all the same, the n $Y^{15}$s are all the same, the n $Y^{16}$ is are all the same, the n $Y^{17}$ is are all the same, and the n $Y^{18}$s are all the same is preferred. As an embodiment of the present invention, a compound in which n is 3 can be mentioned. As another embodiment of the present invention, a compound in which n is 1 can be mentioned.

As another preferred compound, a compound in which p is 1 can be mentioned. In this case, p is preferably any integer of 1 to 3, and more preferably 1 or 2. n is preferably 0 or 1, and may be 0.

The compound represented by the general formula (1) is preferably a compound having a PBHT value of 0.91 or more, more preferably a compound having a PBHT value of 0.91 or more in which n is 2 or more, and further preferably a compound having a PBHT value of 0.91 or more in which n is 2. A compound having a PBHT value of 0.91 or more in which p is 1 and n is 0 or in which p is 1 and n is 1 is also preferred.

In the general formula (1), $Y^1$ to $Y^8$ and $Y^{11}$ to $Y^{18}$ each independently represent N or C—R, and R represents a hydrogen atom, a substituent, or a direct bond to L. R that represents a direct bond to L is in only one of $Y^1$ to $Y^4$, or in only one of $Y^{11}$ to $Y^{14}$. As an embodiment of the present invention, a compound in which $Y^1$ is C—R and R represents a direct bond to L can be mentioned. As an embodiment of the present invention, a compound in which $Y^2$ is C—R and R represents a direct bond to L can be mentioned. As an embodiment of the present invention, a compound in which $Y^3$ is C—R and R represents a direct bond to L can be mentioned. As an embodiment of the present invention, a compound in which $Y^4$ is C—R and R represents a direct bond to L can be mentioned. As an embodiment of the present invention, a compound in which $Y^{11}$ is C—R and R represents a direct bond to L can be mentioned. As an embodiment of the present invention, a compound in which $Y^{12}$ is C—R and R represents a direct bond to L can be mentioned. As an embodiment of the present invention, a compound in which $Y^{13}$ is C—R and R represents a direct bond to L can be mentioned. As an embodiment of the present invention, a compound in which $Y^{14}$ is C—R and R represents a direct bond to L can be mentioned.

When n is 2 or more, in the n dibenzofuran rings or dibenzothiophene rings, $Y^{11}$ to $Y^{14}$ in which R represents a direct bond to L may be the same or different. Such $Y^{11}$ to $Y^{14}$ are preferably the same.

$Y^1$ to $Y^8$ and $Y^{11}$ to $Y^{18}$ in the general formula (1) may all be C—R. The number of $Y^1$ to $Y^8$ and $Y^{11}$ to $Y^{18}$ that represent N in a molecule may be one or more, may be two or more, may be three or more, may be four or more, may be six or more, or may be nine or more. The number of $Y^1$ to $Y^8$ and $Y^{11}$ to $Y^{18}$ that represent N in a molecule may be 15 or less, may be 10 or less, may be seven or less, may be five or less. As an embodiment of the present invention, a compound in which $Y^1$ is N can be mentioned. As an embodiment of the present invention, a compound in which $Y^2$ is N can be mentioned. As an embodiment of the present invention, a compound in which $Y^3$ is N can be mentioned. As an embodiment of the present invention, a compound in which $Y^4$ is N can be mentioned. As an embodiment of the present invention, a compound in which $Y^5$ is N can be mentioned. As an embodiment of the present invention, a compound in which $Y^6$ is N can be mentioned. As an embodiment of the present invention, a compound in which $Y^7$ is N can be mentioned. As an embodiment of the present invention, a compound in which $Y^8$ is N can be mentioned. As an embodiment of the present invention, a compound in which $Y^{11}$ is N can be mentioned. As an embodiment of the present invention, a compound in which $Y^{12}$ is N can be mentioned. As an embodiment of the present invention, a compound in which $Y^{13}$ is N can be mentioned. As an embodiment of the present invention, a compound in which $Y^{14}$ is N can be mentioned. As an embodiment of the present invention, a compound in which $Y^{15}$ is N can be mentioned. As an embodiment of the present invention, a compound in which $Y^{16}$ is N can be mentioned. As an embodiment of the present invention, a compound in which $Y^{17}$ is N can be mentioned. As an embodiment of the present invention, a compound in which $Y^{18}$ is N can be mentioned.

In the general formula (1). $Y^{21}$ to $Y^{28}$ each independently represent N or C—R'. $R^1$ represents a hydrogen atom or a substituent. The number of $Y^{21}$ to $Y^{28}$ that represent N is preferably zero to three, more preferably zero to two, and may be one. $Y^{21}$ to $Y^{28}$ may all be C—R'.

In the general formula (1), two that are adjacent to each other of $Y^1$ to $Y^8$ and $Y^{11}$ to $Y^{18}$ may both represent C—R in which the Rs are bonded to each other to form a ring structure. In the general formula (1), two that are adjacent to each other of $Y^{21}$ to $Y^{28}$ may both represent C—$R^1$ in which the R's are bonded to each other to form a ring structure. The ring structure is preferably a 5 to 8-membered ring, more preferably a 5 to 7-membered ring, further preferably a 5-membered ring or 6-membered ring. The ring structure formed may be a monocyclic structure, or may be a polycyclic structure in which rings are condensed. The ring structure formed may be an aromatic ring or an aliphatic ring, or may be a hydrocarbon ring or a heterocyclic ring.

Examples of the substituent represented by R and $R^1$ include a hydroxy group, a halogen atom, an alkyl group having 1 to 20 carbon atoms, an alkoxy group having 1 to 20 carbon atoms, an alkylthio group having 1 to 20 carbon atoms, an aryl group having 6 to 40 carbon atoms, an aryloxy group having 6 to 40 carbon atoms, an arylthio group having 6 to 40 carbon atoms, a heteroaryl group having 3 to 40 carbon atoms, a heteroaryloxy group having 3 to 40 carbon atoms, a heteroarylthio group having 3 to 40 carbon atoms, an alkenyl group having 2 to 10 carbon atoms, an alkynyl group having 2 to 10 carbon atoms, a trialkylsilyl group having 3 to 20 carbon atoms, a cyano group, a diarylamino group (the two aryl groups are not bonded to each other), and a diarylamino group (the two aryl groups are bonded to each other to form a ring structure). In the specific examples, a substituent that can be further substituted with a substituent may be substituted or unsubstituted. As the further substituent when the substituent is further substituted, the substituents exemplified above can be mentioned. More preferred substituents are a substituted or unsubstituted alkyl group having 1 to 20 carbon atoms, an alkoxy group having 1 to 20 carbon atoms, a substituted or unsubstituted aryl group having 6 to 40 carbon atoms, and a substituted or unsubstituted heteroaryl group having 3 to 40 carbon atoms. Further preferred substituents are a substituted or unsubstituted alkyl group having 1 to 10 carbon atoms, a substituted or unsubstituted alkoxy group having 1 to 10 carbon atoms, a substituted or unsubstituted aryl group having 6 to 15 carbon atoms, and a substituted or unsubstituted heteroaryl group having 3 to 12 carbon atoms. For example, a substituted or unsubstituted aryl group can be selected and adopted.

All of the Rs present in the general formula (1) except for a direct bond to L may be a hydrogen atom. Only one of the Rs present in the general formula (1) may be a substituent, two may be a substituent, three may be a substituent, four or more may be a substituent, six or more may be a substituent, or nine or more may be a substituent. Of the Rs present in the general formula (1), 15 or less may be a substituent, 10 or less may be a substituent, seven or less may be a substituent, or five or less may be a substituent.

All of the R's present in the general formula (1) may be a hydrogen atom. Only one of the R's present in the general formula (1) may be a substituent, two may be a substituent, three may be a substituent, or four or more substituent. Of the R's present in the general formula (1), eight or less may be a substituent, six or less may be a substituent, four or less may be a substituent, or five or less may be a substituent.

In the general formula (1), L represents a (n+p+1)-valent conjugated linking group having at least one aromatic ring or heteroaromatic ring. The conjugated linking group, as used herein, means that a structure that links the tricyclic structure on the left side of the general formula (1), the n tricyclic structures on the right hand, and the p tricyclic structures on the upper side is a conjugated structure. The structure that links the tricyclic structures may be formed only of aromatic rings or heteroaromatic rings, or may be formed of a combination of an aromatic ring or heteroaromatic ring and one or more structures selected from the group consisting of an aromatic ring, a heteroaromatic ring, an alkenylene group, and an alkynylene group. When two or more structures are combined, structures of the same type (for example, an aromatic ring and an aromatic ring) may be combined or structures of different types (for example, an aromatic ring and an alkenylene group) may be combined. When combined, combinations of an aromatic ring and an aromatic ring, an aromatic ring and a heteroaromatic ring, an aromatic ring and an alkenylene group, a heteroaromatic ring and a heteroaromatic ring, a heteroaromatic ring and an alkenylene group can be exemplified. The aromatic ring, heteroaromatic ring, and alkenylene group, as used herein, may be substituted with a substituent. As examples of the substituent herein, the substituents exemplified in the description of R in the general formula (1) can be mentioned. As examples of the alkenylene group, an ethylene group, a phenylethylene group, a diphenylethylene group, a naphthylethylene group, and a dinaphthylethylene group can be mentioned.

As specific examples of L, a (n+p+1)-valent benzene ring, a (n+p+1)-valent naphthalene ring, a (n+p+1)-valent anthracene ring, a (n+p+1)-valent phenanthrene ring, a (n+p+1)-valent triphenylene ring, a (n+p+1)-valent pyrene ring, a (n+p+1)-valent chrysene ring, and a (n+p+1)-valent pyridine ring can be mentioned. As specific examples of L, a (n+p+1)-valent benzene structure, a (n+p+1)-valent biphenyl structure, a (n+p+1)-valent o-terphenyl structure, a (n+p+1)-valent m-terphenyl structure, and a (n+p+1)-valent p-terphenyl structure can also be mentioned. As specific preferred examples of L, a (n+p+1)-valent benzene structure and a (n+p+1)-valent biphenyl structure can be mentioned, and a (n+p+1)-valent benzene structure is more preferred.

When L is a biphenyl structure, in a preferred embodiment, at least the position 3 of the biphenyl structure is substituted with a tricyclic structure. In a preferred embodiment, at least the position 3 and the position 5 are substituted with a tricyclic structure. In a preferred embodiment, at least the position 3, the position 5, and the position 3' are substituted with a tricyclic structure. In a preferred embodiment, at least the position 3, the position 5, and the position 4' are substituted with a tricyclic structure. In a preferred embodiment, at least the position 3, the position 5, and the position 2' are substituted with a tricyclic structure. In another preferred embodiment, at least the position 4' is substituted with a tricyclic structure. In a preferred embodiment, at least the position 3 and the position 4' are substituted with a tricyclic structure. In another preferred embodiment, at least the position 2' is substituted with a tricyclic structure. In a preferred embodiment, at least the position 3 and the position 2' are substituted with a tricyclic structure.

When L is a benzene structure, in a preferred embodiment, two of the tricyclic structures bonded to the benzene structure are preferably substituted at the meta position or the para position, and are particularly preferably substituted at the meta position. When L contains a phenylene group, the phenylene group may be any of a 1,2-phenylene group, a 1,3-phenylene group, and a 1,4-phenylene group, is preferably a 1,3-phenylene group or a 1,4-phenylene group, and is particularly preferably a 1,3-phenylene group.

When L contains a pyridylene group, the pyridylene group may be any of a 2,3-pyridylene group, a 2,4-pyridylene group, a 2,5-pyridylene group, a 2,6-pyridylene group, a 3,4-pyridylene group, and a 3,5-pyridylene group, and is preferably a 2,6-pyridylene group.

As a preferred first compound, a compound having a structure represented by the following general formula (2) can also be mentioned.

General formula (2)

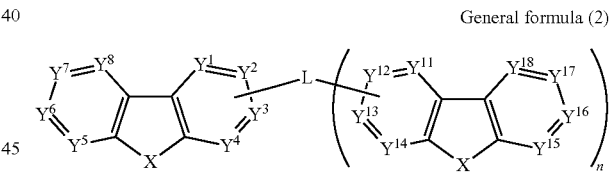

In the general formula (2), multiple Xs each independently represent O or S, $Y^1$ to $Y^8$ and $Y^{11}$ to $Y^{18}$ each independently represent N or C—R, and R represents a hydrogen atom, a substituent, or a direct bond to L. L represents a (n+1)-valent conjugated linking group containing at least one aromatic ring or heteroaromatic ring. n represents an integer of 1 or more. Multiple $Y^{11}$s to $Y^{18}$s may be the same as or different from each other.

About the description and preferred ranges of X, $Y^1$ to $Y^8$, $Y^{11}$ to $Y^{18}$, L, and n, one can refer to the corresponding statements in the general formula (1).

As a preferred embodiment of the present invention, a compound of the general formula (2) in which n is an integer of 2 or more can be mentioned. For example, a compound of the general formula (2) in which n is 2 can be exemplified. As another preferred embodiment of the present invention, a compound of the general formula (2) in which n is 1 and L is a heteroarylene group can be mentioned. For example, a compound in which n is 1 and L is a divalent pyridine ring can be mentioned. As another preferred embodiment of the present invention, a compound of the general formula (2) in which $Y^{12}$ is C—R (R is a single bond to L) can be mentioned. As another preferred embodiment of the present invention, a compound of the general formula (2) in which $Y^2$ is C—R (R is a single bond to L) and $Y^{12}$ is C—R (R is a single bond to L) can be mentioned. As a further preferred embodiment of the present invention, a compound of the general formula (2) in which $Y^2$ is C—R (R is a single bond to L), $Y^{12}$ is C—R (R is a single bond to L), and L is a divalent heteroarylene group, such as a pyridylene group, can be mentioned.

As a preferred example of the first compound, a compound having a structure represented by the following general formula (3) can also be mentioned.

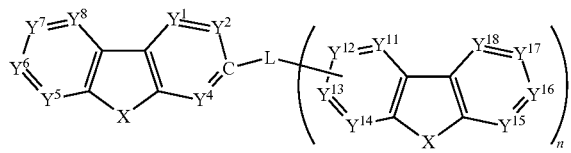

General formula (3)

In the general formula (3), multiple Xs each independently represent O or S, $Y^1$, $Y^2$, $Y^4$ to $Y^8$, and $Y^{11}$ to $Y^{18}$ each independently represent N or C—R and R represents a hydrogen atom, a substituent, or a direct bond to L. L represents a (n+1)-valent conjugated linking group containing at least one aromatic ring or heteroaromatic ring. n represents an integer of 2 or more. Multiple $Y^{11}$s to $Y^{18}$s may be the same as or different from each other.

About the description and preferred ranges of X, $Y^1$, $Y^2$, $Y^4$ to $Y^8$, $Y^{11}$ to $Y^{18}$, L, and n, one can refer to the corresponding statements in the general formula (1). $Y^3$ is C—R and R represents a direct bond to L.

As a preferred embodiment of the present invention, a compound of the general formula (3) in which $Y^{11}$ is C—R and R represents a direct bond to L can be mentioned. As an embodiment of the present invention, a compound in which $Y^{12}$ is C—R and R represents a direct bond to L can be mentioned. As an embodiment of the present invention, a compound in which $Y^{13}$ is C—R and R represents a direct bond to L can be mentioned. As an embodiment of the present invention, a compound in which $Y^{14}$ is C—R and R represents a direct bond to L can be mentioned.

As a preferred first compound, a compound having a structure represented by the following general formula (4) can also be mentioned.

General formula (4)

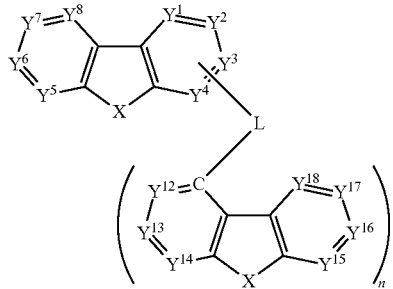

In the general formula (4), multiple Xs each independently represent O or S, $Y^1$ to $Y^8$ and $Y^{12}$ to $Y^{18}$ each independently represent N or C—R, and R represents a hydrogen atom, a substituent, or a direct bond to L. L represents a (n+1)-valent conjugated linking group containing at least one aromatic ring or heteroaromatic ring. n represents an integer of 2 or more. Multiple $Y^{11}$s to $Y^{18}$s may be the same as or different from each other.

About the description and preferred ranges of X, $Y^1$ to $Y^8$, $Y^{12}$ to $Y^{18}$, L, and n, one can refer to the corresponding statements in the general formula (1). $Y^{11}$ is C—R and R represents a direct bond to L.

As an embodiment of the present invention, a compound of the general formula (4) in which $Y^1$ is C—R and R represents a direct bond to L can be mentioned. As an embodiment of the present invention, a compound in which $Y^2$ is C—R and R represents a direct bond to L can be mentioned. As a preferred embodiment of the present invention, a compound in which $Y^3$ is C—R and R represents a direct bond to L can be mentioned. As an embodiment of the present invention, a compound in which $Y^4$ is C—R and R represents a direct bond to L can be mentioned.

As a preferred first compound, a compound having a structure represented by the following general formula (5) can also be mentioned.

General formula (5)

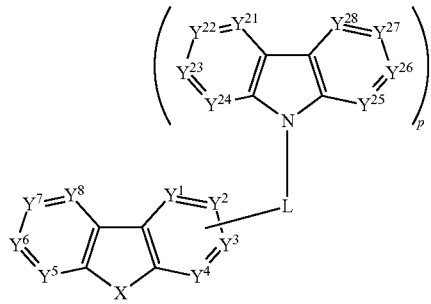

In the general formula (5), X represents O or S, $Y^1$ to $Y^8$ each independently represent N or C—R, and R represents a hydrogen atom, a substituent, or a direct bond to L. $Y^{21}$ to $Y^{28}$ each independently represent N or C—R'. $R^1$ represents a hydrogen atom or a substituent. L represents a (p+1)-valent conjugated linking group containing at least one aromatic ring or heteroaromatic ring. p represents an integer of 1 or more. When p is 2 or more, multiple $Y^{21}$s to $Y^{28}$s may be the same as or different from each other.

About the description and preferred ranges of X, $Y^1$ to $Y^8$, $Y^{21}$ to $Y^{28}$, L, and p, one can refer to the corresponding statements in the general formula (1). As another preferred embodiment of the present invention, a compound of the general formula (5) in which $Y^2$ is C—R (R is a single bond to L) can be mentioned. As another preferred embodiment of the present invention, a compound in which L is a phenylene group, more preferably a 1,3-phenylene group can be mentioned. As another preferred embodiment of the present invention, a compound in which p is 1 can be mentioned.

The dibenzofuran structure and dibenzothiophene structure contained in each of the general formulae (1) to (5) may be bonded to L at the position 1, may be bonded to L at the position 2, may be bonded to L at the position 3, or may be bonded to L at the position 4. When L is a benzene ring (preferably a benzene ring which is bonded at the meta position, such as a m-phenylene group), a compound in which the dibenzofuran structure and dibenzothiophene structure are substituted on L at the position 1 or the position 2 is preferred, and a compound in which the structures are substituted at the position 2 is more preferred. When L has a biphenyl structure, a compound in which the dibenzofuran structure and dibenzothiophene structure are substituted on L at the position 2 or the position 4 is preferred, and a compound in which the structures are substituted at the position 4 is more preferred.

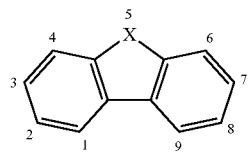

Specific examples of the first compound are exemplified below. However, the first compound that can be used in the present invention is not to be limitedly construed by the specific examples.

Compound 1

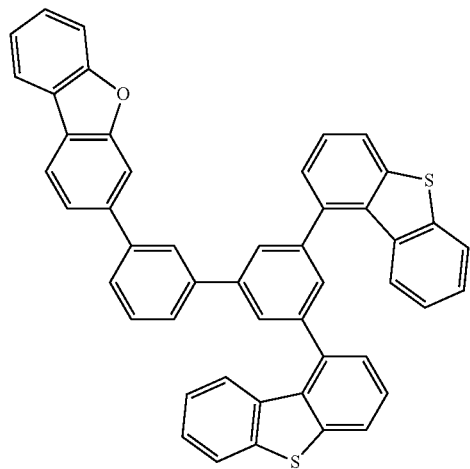

Compound 2

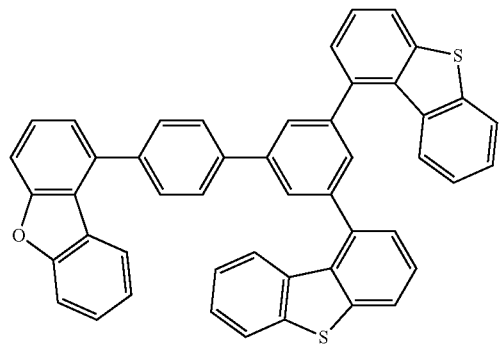

Compound 3

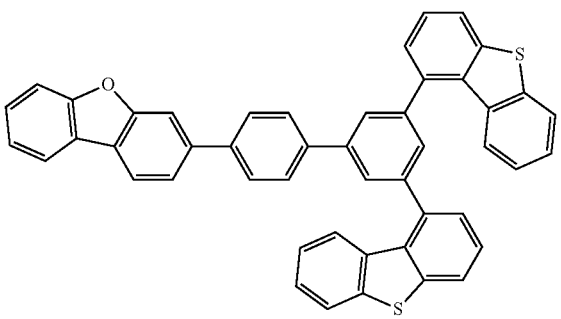

Compound 4

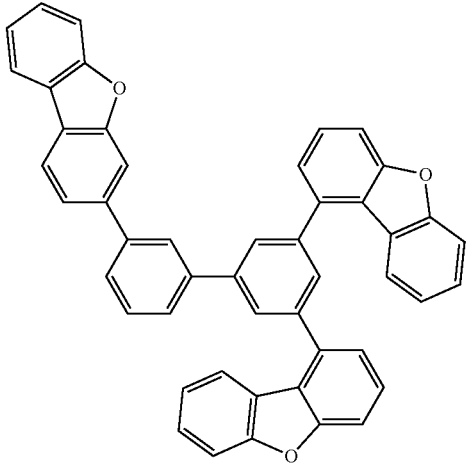

Compound 5

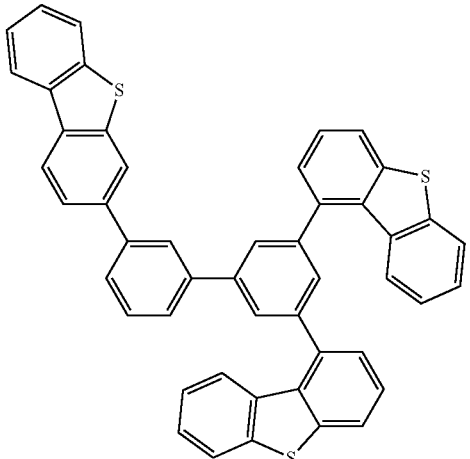

-continued
Compound 6
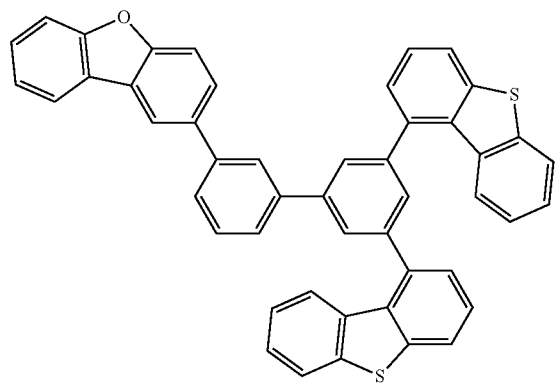
Compound 7
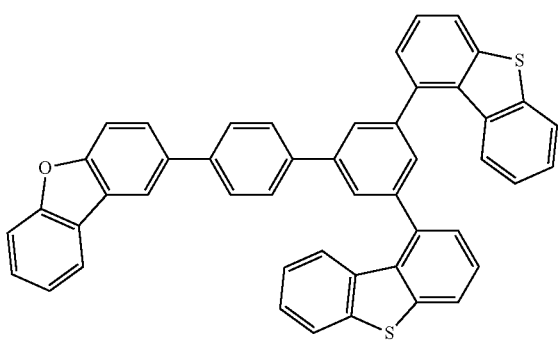
Compound 8
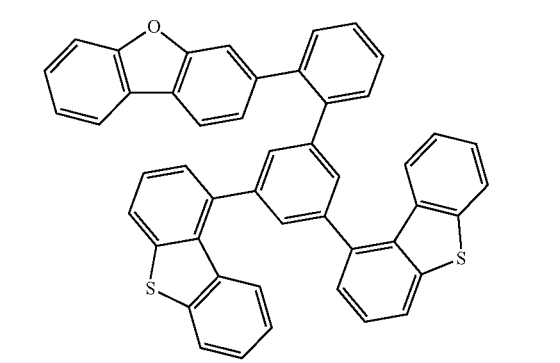
Compound 9
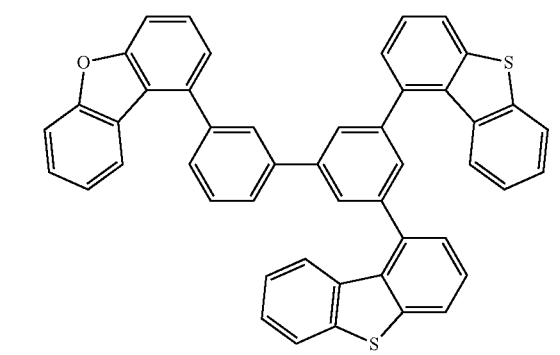
-continued
Compound 10
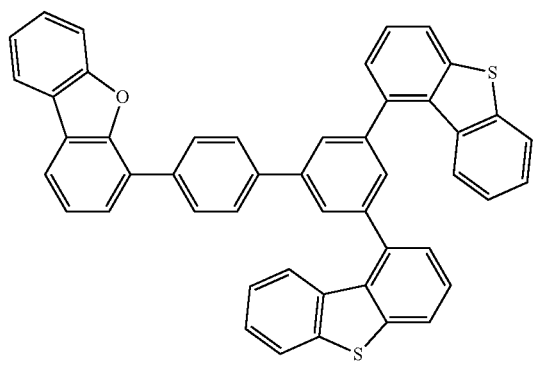
Compound 11
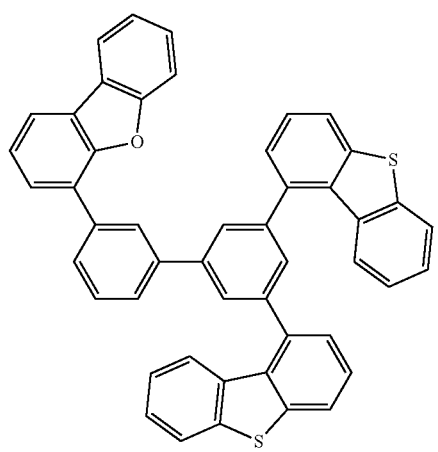
Compound 12
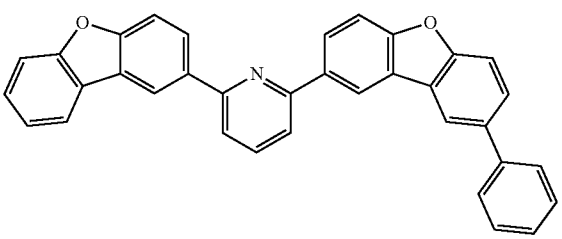
Compound 13
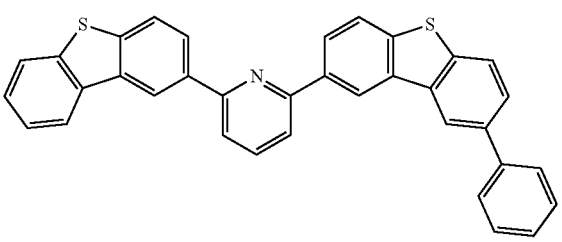

-continued
Compound 14
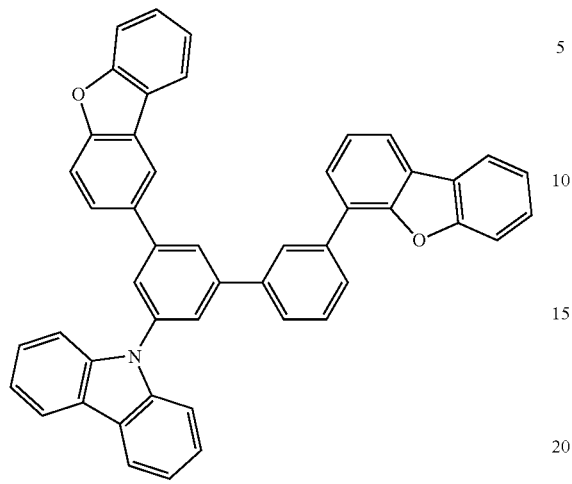
Compound 15
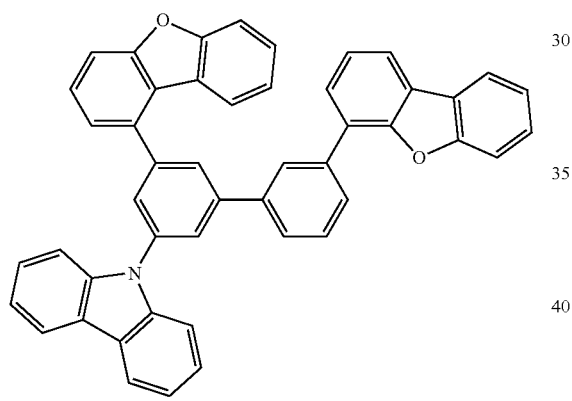
Compound 16
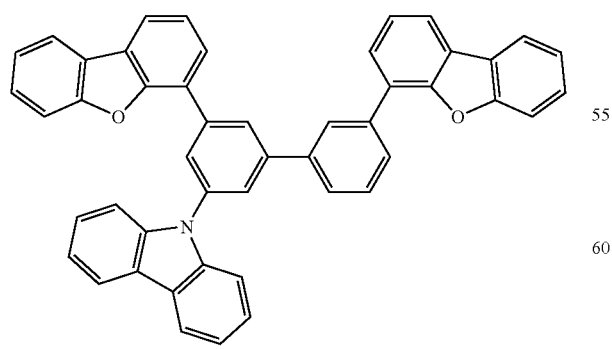
-continued
Compound 17
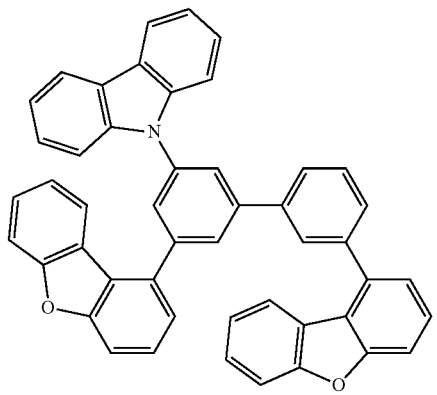
Compound 18
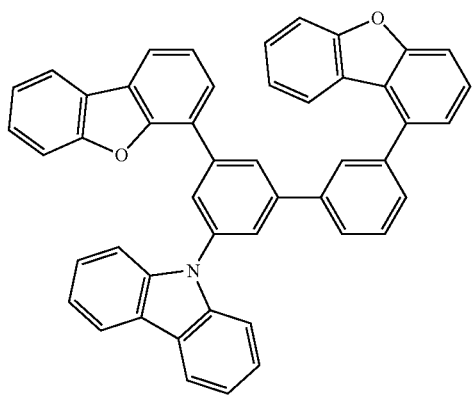
Compound 19
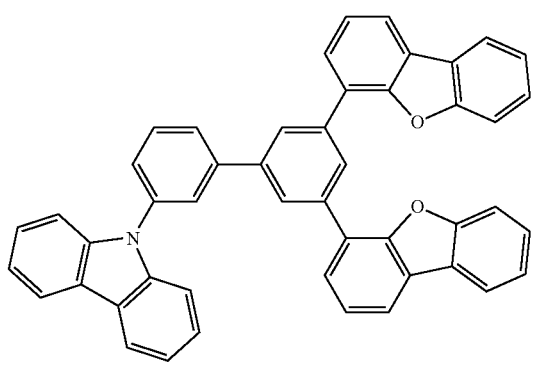
Compound 20
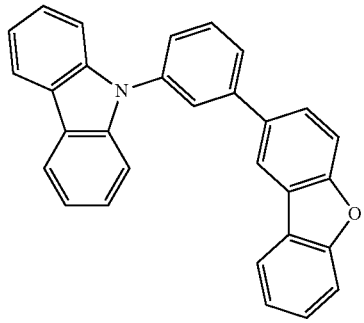

-continued

Compound 21
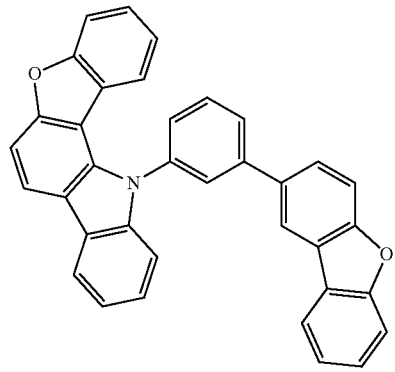

Compound 22
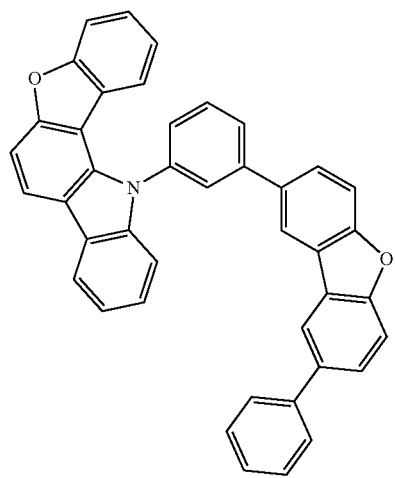

Compound 23
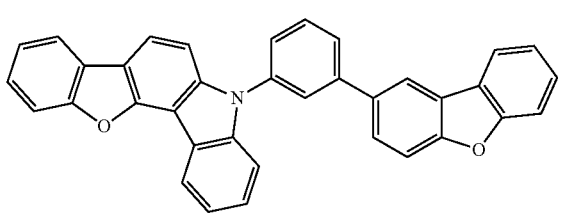

Compound 24
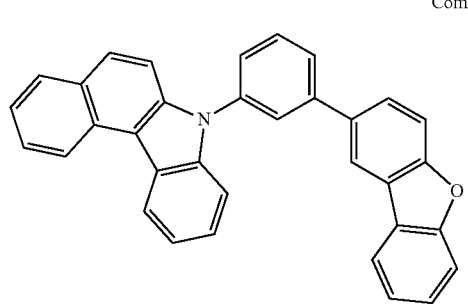

-continued

Compound 25
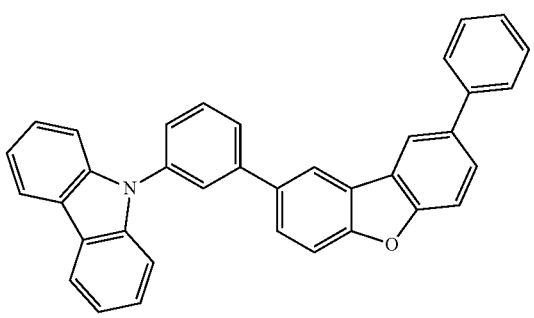

Compound 26
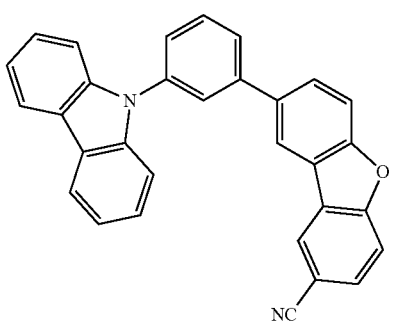

The PBHT values and cation bond dissociation energies of the compounds 1 to 21 are as shown in the following table.

| | PBHT value | Bond dissociation energy (eV) |
|---|---|---|
| Compound 1 | 0.996 | 6.041 |
| Compound 2 | 0.930 | 6.057 |
| Compound 3 | 0.911 | 6.020 |
| Compound 4 | 0.891 | 6.177 |
| Compound 5 | 0.883 | 6.030 |
| Compound 6 | 0.881 | 6.029 |
| Compound 7 | 0.858 | 6.029 |
| Compound 8 | 0.824 | 5.955 |
| Compound 9 | 0.823 | 6.019 |
| Compound 10 | 0.811 | 6.076 |
| Compound 11 | 0.811 | 6.065 |
| Compound 12 | 0.862 | 6.141 |
| Compound 13 | 0.763 | 6.093 |
| Compound 14 | 0.860 | 4.875 |
| Compound 15 | 0.963 | 4.843 |
| Compound 16 | 0.732 | 5.041 |
| Compound 17 | 0.897 | 4.936 |
| Compound 18 | 0.737 | 5.012 |
| Compound 19 | 0.806 | 5.066 |
| Compound 20 | 0.959 | 4.894 |
| Compound 21 | 0.760 | 4.329 |
| Compound 22 | 0.734 | 4.388 |
| Compound 23 | 0.813 | 4.392 |
| Compound 24 | 0.790 | 4.611 |
| Compound 25 | 0.792 | 4.988 |
| Compound 26 | 0.874 | 4.741 |

(Second Compound)

The second compound is a compound having a lowest excited singlet energy level lower than that of the first compound and having $\Delta E_{ST}(2)$ less than 0.20 eV. The second compound tends to easily undergo reverse intersystem crossing from the excited triplet state to the excited singlet state since the lowest excited singlet energy level $E_{S1}(2)$ is close to the lowest excited triplet energy level $E_{T1}(2)$. The occurrence of reverse intersystem crossing in the second compound can be confirmed by observing delayed fluorescence emitted when the excited singlet state generated by reverse intersystem crossing is radiatively deactivated to the ground singlet state.

"Delayed fluorescence" in this description means fluorescence having a fluorescence emission lifetime ($\tau$) of 200 ns (nanoseconds) or more. As used herein, "fluorescence emission lifetime ($\tau$)" refers to a time period determined by measuring the attenuation of emission after completion of optical excitation in a solution or deposited film sample under a condition in the absence of oxygen, such as in a nitrogen atmosphere or under vacuum. In this description, when two or more fluorescence components having different fluorescence emission lifetimes are observed, the emission lifetime of a fluorescence component having the longest emission lifetime is considered as the "fluorescence emission lifetime ($\tau$)". In this description, a fluorescence emission lifetime of 200 ns or more is particularly referred to as delayed fluorescence lifetime ($\tau_{DELAY}$). The delayed fluorescence lifetime ($\tau_{DELAY}$) of the second compound is preferably less than 10 $\mu$s (microseconds).

The second compound is preferably a material that undergoes reverse intersystem crossing from the excited triplet state to the excited singlet state, and more preferably a material that emits delayed fluorescence. Since the second compound undergoes reverse intersystem crossing, the excited triplet state is converted to the excited singlet state, and the excited singlet energy can be efficiently used for light emission of the second compound or a light emitting material (third compound).

The second compound preferably has a smaller $\Delta E_{ST}(2)$, specifically, the $\Delta E_{ST}(2)$ is preferably less than 0.15 eV, less than 0.10 eV, more preferably less than 0.05 eV, and still more preferably less than 0.01 eV, and is ideally 0 eV. The second compound having a smaller $\Delta E_{ST}(2)$ tends to easily undergo reverse intersystem crossing, and can effectively exhibit the action of converting the excited triplet state to the excited singlet state.

The second compound is preferably a compound having a PBHT value more than 0.10, more preferably more than 0.15, and further preferably more than 0.20. The second compound is preferably a compound having a PBHT value less than 0.50, more preferably less than 0.45, and further preferably less than 0.40. The second compound is particularly preferably a compound having a PBHT value more than 0.20 and less than 0.40.

The second compound may be a material constituted of a single compound satisfying the expression (2b), or may be a material constituted of two or more compounds that form an exciplex, the exciplex having a difference between the lowest excited singlet energy level $E_{S1}$ and the lowest excited triplet energy level $E_{T1}$ less than 0.20 eV. The second compound easily undergoes radiative deactivation from the excited triplet state to the ground singlet state at a normal temperature (300K), and thus is preferably not a normal phosphorescent material like a metal complex having a heavy metal element, such as Ir or Pt, as a central metal. That is, the second compound is preferably a compound not containing a metal element, preferably a compound not containing a heavy metal element, preferably a compound constituted only of atoms selected from the group consisting of a carbon atom, a hydrogen atom, a nitrogen atom, an oxygen atom, a sulfur atom, and a silicon atom, preferably a compound constituted only of atoms selected from the group consisting of a carbon atom, a hydrogen atom, a nitrogen atom, an oxygen atom, and a sulfur atom, preferably a compound constituted only of atoms selected from the group consisting of a carbon atom, a hydrogen atom, a nitrogen atom, and an oxygen atom, and preferably a compound constituted only of atoms selected from the group consisting of a carbon atom, a hydrogen atom, and a nitrogen atom.

As the second compound, for example, a compound represented by the following general formula (2A) can be mentioned.

D-L-A                           General formula (2A)

In the general formula (2A). D represents a substituent having a substituted amino group, L represents a substituted or unsubstituted arylene group, or a substituted or unsubstituted heteroarylene group, and A represents a cyano group or a substituted or unsubstituted heteroaryl group containing at least one nitrogen atom as a ring backbone forming atom.

The arylene group or heteroarylene group represented by L may be a monocyclic ring, or may be a condensed ring in which two or more rings are condensed. When L is a condensed ring, the number of rings condensed is preferably two to six, for example, can be selected from two to four. As specific examples of the ring constituting L, a benzene ring, a pyridine ring, a pyrimidine ring, a triazine ring, and a naphthalene ring can be mentioned. As specific examples of the arylene group or heteroarylene group represented by L, a 1,4-phenylene group, a 1,3-phenylene group, a 1,2-phenylene group, a 1,8-naphthylene group, a 2,7-naphthylene group, a 2,6-naphthylene group, a 1,4-naphthylene group, a 1,3-naphthylene group, a 9,10-anthracenylene group, a 1,8-anthracenylene group, a 2,7-anthracenylene group, a 2,6-anthracenylene group, a 1,4-anthracenylene group, a 1,3-anthracenylene group, a group obtained by substituting one of the ring backbone forming atoms of the above groups with a nitrogen atom, a group obtained by substituting two of the ring backbone forming atoms of the above groups with a nitrogen atom, and a group obtained by substituting three of the ring backbone forming atoms of the above groups with a nitrogen atom. The arylene group or heteroarylene group represented by L may have a substituent or may be unsubstituted. When the arylene group or heteroarylene group has two or more substituents, the multiple substituents may be the same as or different from each other. Examples of the substituent include a hydroxy group, a halogen atom, an alkyl group having 1 to 20 carbon atoms, an alkoxy group having 1 to 20 carbon atoms, an alkylthio group having 1 to 20 carbon atoms, an aryl group having 6 to 40 carbon atoms, a heteroaryl group having 3 to 40 carbon atoms, an alkenyl group having 2 to 10 carbon atoms, an alkynyl group having 2 to 10 carbon atoms, a haloalkyl group having 1 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, a trialkylsilylalkynyl group having 5 to 20 carbon atoms, a substituent having a substituted amino group, and a cyano group. In the specific examples, a group that can be further substituted with a substituent may be substituted. Preferred substituents are a substituted or unsubstituted alkyl group having 1 to 20 carbon atoms, an alkoxy group having 1 to 20 carbon atoms, a substituted or unsubstituted aryl group having 6 to 40 carbon atoms, and a substituted or unsubstituted heteroaryl group having 3 to 40 carbon atoms. Further preferred substituents are a substituted or unsubstituted alkyl group having 1 to 10 carbon atoms, a substituted or unsubstituted alkoxy group having 1 to 10 carbon atoms, a substituted or unsubstituted aryl group having 6 to 15 carbon atoms, and a substituted or unsubstituted heteroaryl group having 3 to 12 carbon atoms.

In the heteroaryl group containing at least one nitrogen atom as a ring backbone forming atom in A, the number of the nitrogen atoms as ring backbone forming atoms is preferably one to three. About a preferred range and specific examples of the heteroaryl group, one can refers to the aforementioned preferred range and specific examples of the heteroarylene group represented by L with conversion to monovalent groups. Among them, the heteroaryl group in A is preferably a group formed of a 6-membered ring containing one to three nitrogen atoms as ring backbone forming atoms, and is more preferably a pyridinyl group, a pyrimidinyl group, or a triazinyl group, and further preferably a triazinyl group. The heteroaryl group may be substituted with a substituent. About a preferred range and specific examples of the substituent, one can refer to the aforementioned preferred range and specific examples of the substituent that can be substituted on the arylene group or heteroarylene group represented by L.

A may be such a substituted or unsubstituted heteroaryl group, but is preferably a cyano group. A compound in which A is a cyano group is more preferred than a compound in which A is a triazinyl group.

As the compound represented by the general formula (2A), a compound containing a cyanobenzene backbone represented by the following general formula (2B) or a compound containing a triazine backbone represented by the following general formula (2C) can be mentioned.

General formula (2B)

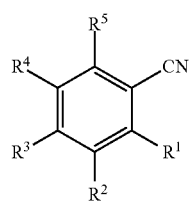

In the general formula (2B), zero to four of $R^1$ to $R^5$ represent a cyano group, at least one of $R^1$ to $R^5$ represents a substituent having a substituted amino group, and the others of $R^1$ to $R^5$ represent a hydrogen atom or a substituent that is not a substituent having a substituted amino group nor a cyano group.

General formula (2C)

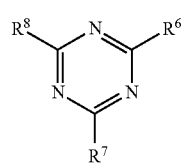

In the general formula (2C), at least one of $R^6$ to $R^8$ represents a substituted amino group and the others of $R^6$ to $R^8$ represent a hydrogen atom or a substituent that is not a substituent having a substituted amino group nor a cyano group.

The substituent having a substituted amino group mentioned for the general formula (2A) to (2C) is preferably a substituent having a diarylamino group, and the two aryl groups constituting the diarylamino group may be linked to each other to form, for example, a carbazolyl group. The substituent having a substituted amino group in the general formula (2B) may be any of $R^1$ to $R^5$, and, for example, $R^2$, $R^3$, $R^4$, $R^1$ and $R^3$, $R^1$ and $R^4$, $R^1$ and $R^5$, $R^2$ and $R^3$, $R^1$, $R^3$, and $R^5$, $R^1$, $R^2$, and $R^3$, $R^1$, $R^3$, and $R^4$, $R^2$, $R^3$, and $R^4$, $R^1$, $R^2$, $R^3$, and $R^4$, $R^1$, $R^2$, $R^3$, $R^4$, and $R^5$ and the like can be preferably exemplified. The substituent having a substituted amino group in the general formula (2C) may be any of $R^6$ to $R^8$, and, for example, $R^6$, $R^6$ and $R^7$, $R^6$, $R^7$, and $R^8$ can be exemplified.

The substituent having a substituted amino group mentioned for the general formula (2A) to (2C) is preferably a substituent represented by the following general formula (W1). Two substituents represented by the general formula (W1) may be present in a molecule, or three or more such substituents may be present therein. In the case of a compound represented by the general formula (2A) or the general formula (2B), four or more substituents represented by the general formula (W1) may be present in a molecule. The position of substitution with the substituent represented by the general formula (W1) is not particularly limited.

General formula (W1)

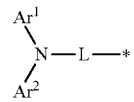

In the general formula (W1), $Ar^1$ and $Ar^2$ each independently represent a substituted or unsubstituted aryl group or a substituted or unsubstituted heteroaryl group. L represents a single bond, a substituted or unsubstituted arylene group, or a substituted or unsubstituted heteroarylene group. * represents a bonding position to the carbon atom (C) in the general formulae (2A) to (2C).

$Ar^1$ and $Ar^2$ in the general formula (W1) may be bonded to each other to form a ring structure together with a nitrogen atom in the general formula (W1).

The arylene group or heteroarylene group represented by $Ar^1$ and $Ar^2$ may be a monocyclic group or a condensed ring in which two or more rings are condensed. In the case of a condensed ring, the number of the rings condensed is preferably two to six, and, for example, can be selected from two to four. Specific examples of the rings constituting $Ar^1$ and $Ar^2$ include a benzene ring, a pyridine ring, a pyrimidine ring, a triazine ring, and a naphthalene ring. As specific examples of the arylene group or heteroarylene group represented by $Ar^1$ and $Ar^2$, a phenyl group, a 1-naphthyl group, a 2-naphthyl group, a 1-anthracenyl group, a 2-anthracenyl group, a 9-anthracenyl group, a 2-pyridyl group, a 3-pyridyl group, and a 4-pyridyl group can be mentioned. The arylene group or heteroarylene group represented by $Ar^1$ and AP may have a substituent or may be unsubstituted. When the group has two or more substituents, the multiple substituents may be the same as or different from each other. Examples of the substituent include a hydroxy group, a halogen atom, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an aryl-substituted amino group having 1 to 20 carbon atoms, an aryl group having 6 to 40 carbon atoms, a heteroaryl group having 3 to 40 carbon atoms, an alkenyl group having 2 to 10 carbon atoms, an alkynyl group having 2 to 10 carbon atoms, an alkylamide group having 2 to 20 carbon atoms, an arylamide group having 7 to 21 carbon atoms, and a trialkylsilyl group having 3 to 20 carbon atoms. In the specific examples, a substituent that can be further substituted by a substituent may be substituted. Preferred substituents are an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an aryl-substituted amino group having 1 to 20 carbon atoms, an aryl group having 6 to 40 carbon atoms, and a heteroaryl group having 3 to 40 carbon atoms.

The substituent represented by the general formula (W1) is preferably a substituent represented by the following general formula (W2).

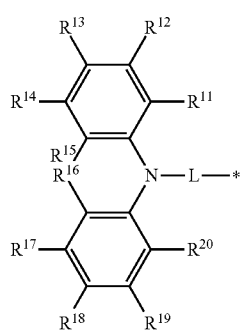

General formula (W2)

In the general formula (W2), $R^{11}$ to $R^{20}$ each independently represent a hydrogen atom or a substituent. L represents a single bond, a substituted or unsubstituted arylene group, or a substituted or unsubstituted heteroarylene group. $R^{11}$ and $R^{12}$, $R^{12}$ and $R^{13}$, $R^{11}$ and $R^{14}$, $R^{14}$ and $R^{15}$, $R^{15}$ and $R^{16}$, $R^{16}$ and $R^{17}$, $R^{17}$ and $R^{18}$, $R^{18}$ and $R^{19}$, and $R^{19}$ and $R^{20}$ may be bonded to each other to form a linking group required for forming a ring structure. $R^{15}$ and $R^{16}$ may be bonded to each other to form a single bond or a linking group. * represents a bonding position to the carbon atom (C) in the general formulae (2A) to (2C).

About specific examples and preferred ranges of the substituent that can be represented by $R^{11}$ to $R^{20}$, one can refer to the corresponding statements about the substituent of the arylene group or heteroarylene group represented by $Ar^1$ and $Ar^2$ in the general formula (2A).

The ring structure formed by $R^{11}$ and $R^{12}$, $R^{12}$ and $R^{13}$, $R^{13}$ and $R^{14}$, $R^{14}$ and $R^{15}$, $R^{15}$ and $R^{16}$, $R^{16}$ and $R^{17}$, $R^{17}$ and $R^{18}$, $R^{18}$ and $R^{19}$, or $R^{19}$ and $R^{20}$ bonded to each other may be an aromatic ring, may be an aliphatic ring, or may be a ring containing a heteroatom. The ring structure may be a condensed ring of two or more rings. The heteroatom, as used herein, is preferably an atom selected from the group consisting of a nitrogen atom, an oxygen atom, and a sulfur atom. As examples of the ring structure formed, a benzene ring, a naphthalene ring, a pyridine ring, a pyridazine ring, a pyrimidine ring, a pyrazine ring, a pyrrole ring, an imidazole ring, a pyrazole ring, an imidazoline ring, an oxazole ring, an isooxazole ring, a thiazole ring, an isothiazole ring, a cyclohexadiene ring, a cyclohexene ring, a cyclopentaene ring, a cycloheptatriene ring, a cycloheptadiene ring, and a cycroheptaene ring can be mentioned.

In the general formulae (W1) and (W2). L represents a single bond, a substituted or unsubstituted arylene group, or a substituted or unsubstituted heteroarylene group. L is preferably a single bond or a substituted or unsubstituted arylene group.

The aromatic ring constituting the arylene group represented by L may be a monocyclic ring, or may be a condensed ring in which two or more aromatic rings are condensed, or may be a linked ring in which two or more aromatic rings are linked. When two or more aromatic rings are linked, the aromatic rings may be linked in a linear form or may be linked in a branched form. The number of carbons of the aromatic ring constituting the arylene group represented by L is preferably 6 to 22, more preferably 6 to 18, further preferably 6 to 14, and furthermore preferably 6 to 10. As specific examples of the arylene group, a phenylene group, a naphthalenediyl group, and a biphenylene group can be mentioned.

The heterocyclic ring constituting the heteroarylene group represented by L may be a monocyclic ring, or may be a condensed ring in which one or more heterocyclic rings and an aromatic ring or heterocyclic ring are condensed, or may be a linked ring in which one or more heterocyclic rings and an aromatic ring or heterocyclic ring are linked. The number of carbon atoms of the heterocyclic ring is preferably 5 to 22, more preferably 5 to 18, further preferably 5 to 14, and furthermore preferably 5 to 10. The heteroatom constituting the heterocyclic ring is preferably a nitrogen atom. As specific examples of the heterocyclic ring, a pyridine ring, a pyridazine ring, a pyrimidine ring, a triazole ring, and a benzotriazole ring can be mentioned.

A preferred group represented by L is a phenylene group. When L is a phenylene group, the phenylene group may be any of a 1,2-phenylene group, a 1,3-phenylene group, and a 1,4-phenylene group, but is preferably a 1,4-phenylene group. L may be substituted by a substituent. The number and the substitution position of substituents of L are not particularly limited. About the description and preferred ranges of the substituents that can be introduced in L, one can refer to the aforementioned description and preferred ranges of the substituent that can be represented by $R^{11}$ to $R^{20}$.

The substituent represented by the general formula (W2) is preferably a substituent represented by any one of the following general formulae (W3) to (W7).

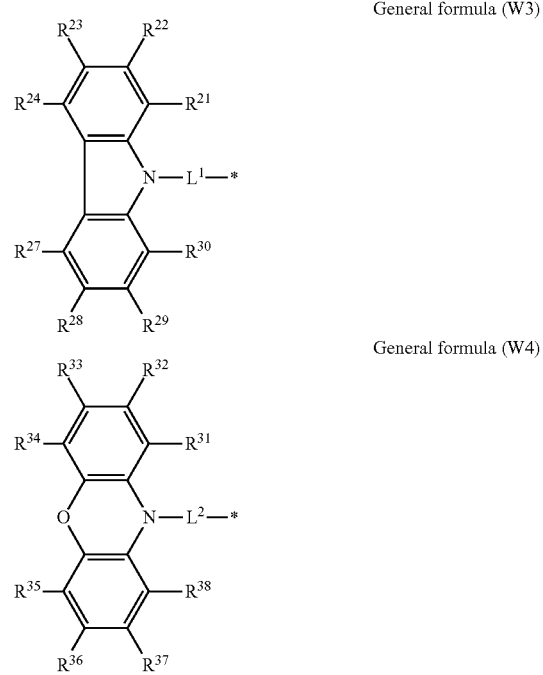

General formula (W3)

General formula (W4)

-continued

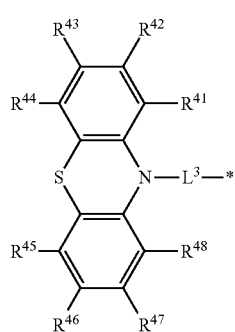

General formula (W5)

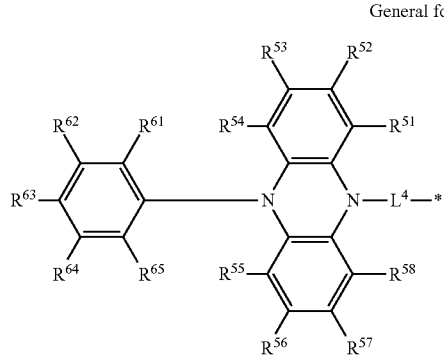

General formula (W6)

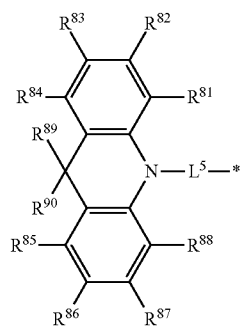

General formula (W7)

In the general formulae (W3) to (W7), $R^{21}$ to $R^{24}$, $R^{27}$ to $R^{38}$, $R^{41}$ to $R^{48}$, $R^{51}$ to $R^{58}$, $R^{61}$ to $R^{81}$, and $R^{90}$ each independently represent a hydrogen atom or a substituent. About the description and preferred ranges of the substituent herein, one can refer to the aforementioned description and preferred ranges of the substituent of $R^{11}$ to $R^{20}$, $R^{21}$ to $R^{24}$, $R^{27}$ to $R^{38}$, $R^{41}$ to $R^{48}$, $R^{51}$ to $R^{58}$, $R^{61}$ to $R^{65}$, $R^{71}$ to $R^{79}$, and $R^{81}$ to $R^{90}$ each also preferably independently represent a group represented by any one of the general formulae (W3) to (W7). At least two of $R^{21}$, $R^{23}$, $R^{28}$, and $R^{30}$ of the general formula (W3) are each preferably a substituted or unsubstituted alkyl group. More preferably, all of $R^{21}$, $R^{23}$, $R^{28}$, $R^{30}$ are each a substituted or unsubstituted alkyl group. $R^{21}$ and $R^{30}$ are each a substituted or unsubstituted alkyl group, or $R^{23}$ and $R^{28}$ are each a substituted or unsubstituted alkyl group. The substituted or unsubstituted alkyl group is more preferably a substituted or unsubstituted alkyl group having 1 to 6 carbon atoms. $R^{89}$ and $R^{90}$ of the general formula (W7) are each preferably a substituted or unsubstituted alkyl group, and more preferably a substituted or unsubstituted alkyl group having 1 to 6 carbon atoms. The number of substituents in the general formula (W3) to (W7) is not particularly limited. It is also preferred that all are unsubstituted (that is, each a hydrogen atom). In each of the general formulae (W3) to (W7), when there are two or more substituents, the substituents may be the same or different. When there is a substituent in the general formulae (W3) to (W7), the substituent is, in the general formula (W3), preferably any one of $R^{22}$ to $R^{24}$ and $R^{27}$ to $R^{29}$, more preferably at least one of $R^{23}$ and $R^{28}$. In the general formula (W4), the substituent is preferably any one of $R^{32}$ to $R^{37}$. In the general formula (W5), the substituent is preferably any one of $R^{42}$ to $R^{47}$. In the general formula (W6), the substituent is preferably any one of $R^{52}$, $R^{53}$, $R^{56}$, $R^{57}$, $R^{62}$ to $R^{64}$. In the general formula (W7), the substituent is preferably any one of $R^{82}$ to $R^{87}$, $R^{89}$, $R^{90}$.

In the general formulae (W3) to (W7), $R^{21}$ and $R^{22}$, $R^{22}$ and $R^{23}$, $R^{23}$ and $R^{24}$, $R^{27}$ and $R^{28}$, $R^{28}$ and $R^{29}$, $R^{29}$ and $R^{30}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{64}$ and $R^{65}$, $R^{54}$ and $R^{61}$, $R^{54}$ and $R^{81}$, $R^{82}$ and $R^{82}$, $R^{82}$ and $R^{83}$, $R^{83}$ and $R^{84}$, $R^{85}$ and $R^{86}$, $R^{87}$ and $R^{88}$, $R^{88}$ and $R^{89}$, $R^{89}$ and $R^{90}$ may be bonded to each other to form a ring structure. About the description and preferred examples of the ring structure, one can refer to the description and preferred examples of the ring structure that $R^{11}$ and $R^{12}$ or the like are bonded to each other to from in the general formula (W2).

In the general formula (W3) to (W7), $L^1$ to $L^5$ each represent a single bond, a substituted or unsubstituted arylene group, or a substituted or unsubstituted heteroarylene group. * represents a bonding position to the carbon atom (C) in the general formula (2A) to (2C). About the description and preferred ranges of the arylene group or heteroarylene group represented by $L^1$ to $L^5$ and the substituent that can be introduced into the groups, one can refer to the description and preferred ranges of the arylene group or heteroarylene group represented by L and the substituent that can be introduced into the groups. $L^1$ to $L^5$ are each preferably a single bond or a substituted or unsubstituted arylene group.

The second compound is, in many cases, a compound known as a compound that emits delayed fluorescence. As such compounds, compounds included in the general formulae described in WO2013/154064, Paragraphs 0008 to 0048 and 0095 to 0133, WO2013/011954, Paragraphs 0007 to 0047 and 0073 to 0085, WO2013/011955, Paragraphs 0007 to 0033 and 0059 to 0066, WO2013/081088, Paragraphs 0008 to 0071 and 0118 to 0133, JP-A-2013-256490, Paragraphs 0009 to 0046 and 0093 to 0134, JP-A-2013-116975, Paragraphs 0008 to 0020 and 0038 to 0040, WO2013/133359, Paragraphs 0007 to 0032 and 0079 to 0084, WO2013/161437, Paragraphs 0008 to 0054 and 0101 to 0121, JP-A-2014-9352, Paragraphs 0007 to 0041 and 0060 to 0069, JP-A-2014-9224, and Paragraphs 0008 to 0048 and 0067 to 0076, in particular, compounds exemplified therein, can be preferably mentioned. These patent literatures are incorporated herein as a part of this description.

In addition, as the compound (delayed fluorescent body) that emits delayed fluorescence, compounds included in the general formulae described in JP-A-2013-253121, WO2013/133359, WO2014/034535, WO2014/115743, WO2014/122895, WO2014/126200, WO2014/136758, WO2014/133121, WO2014/136860, WO2014/196585, WO2014/189122, WO2014/168101, WO2015/008580, WO2014/203840, WO2015/002213, WO2015/016200, WO2015/019725, WO2015/072470, WO2015/108049. WO2015/080182, WO2015/072537, WO2015/080183. JP-A-2015-129240, WO2015/129714, WO2015/129715, WO2015/

133501, WO2015/136880, WO2015/137244, WO2015/137202, WO2015/137136, WO2015/146541, WO2015/159541, in particular, compounds exemplified therein, can be preferably mentioned. These patent literatures are incorporated herein as a part of this description.

The emission wavelength of the second compound is not particularly limited, and can be appropriately selected according to the intended use of the composition of the present invention. For example, when the composition of the present invention is used in a light emitting layer of an organic light emitting element for image display or color display, the second compound is preferably a compound having a maximum emission wavelength in a red region (620 to 750 nm), a green region (495 to 570 nm), or a blue region (450 to 495 nm).

Specific examples of the second compound will be shown below. However, the second compound that can be used in the present invention is not to be limitedly construed by these specific examples.

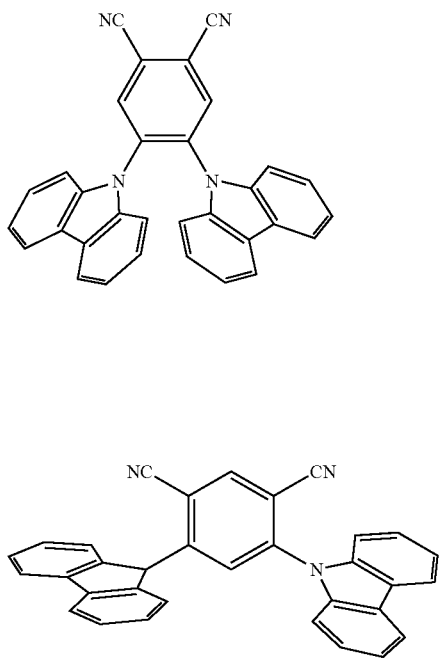

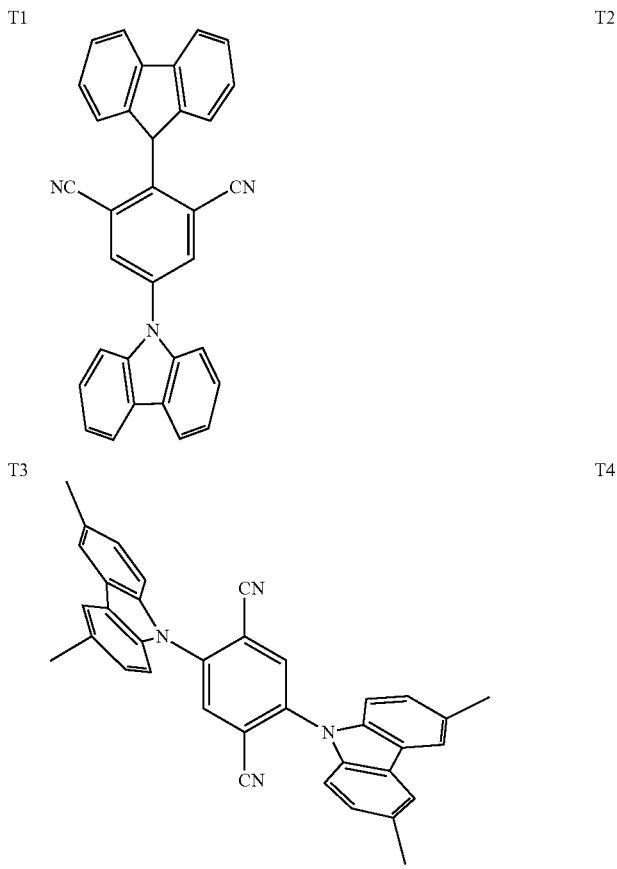

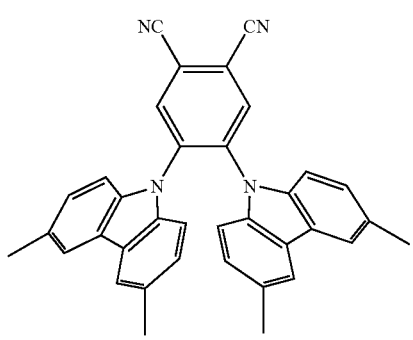

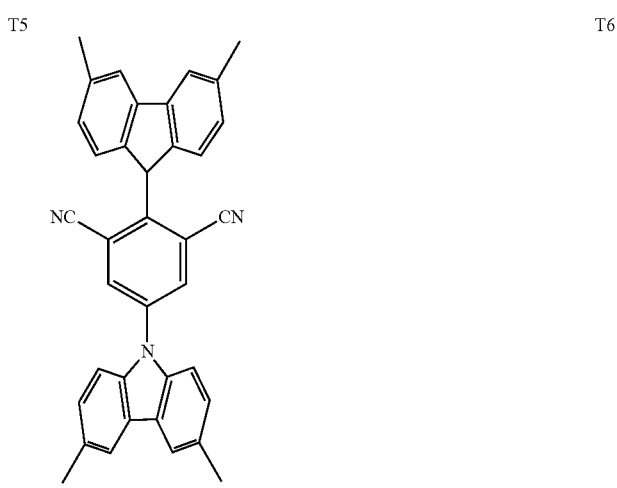

T7
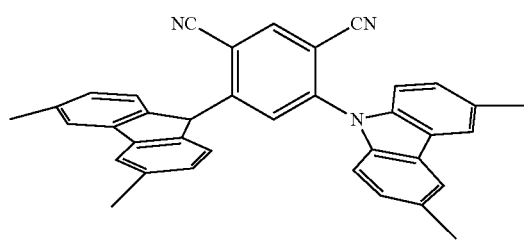
T8
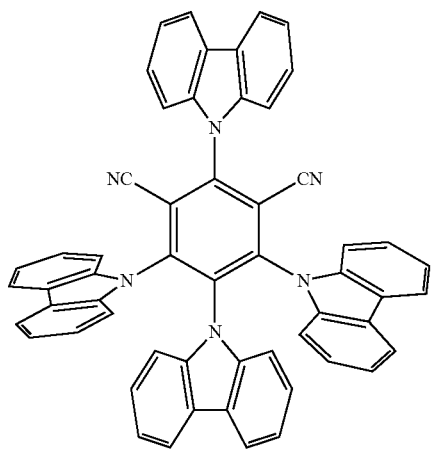
T9
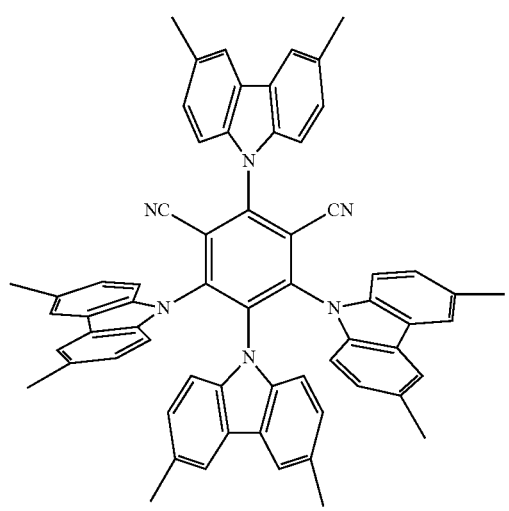
T10
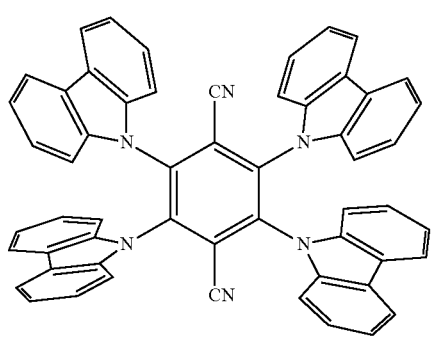
T11
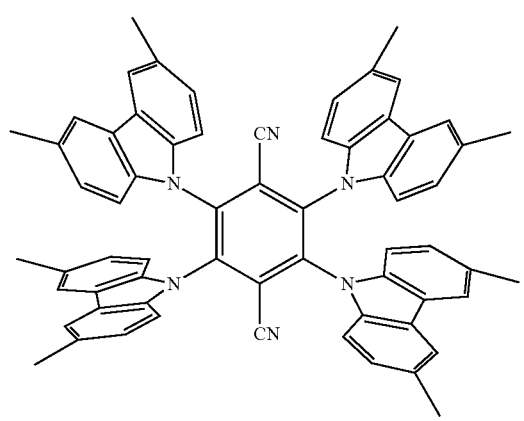
T12
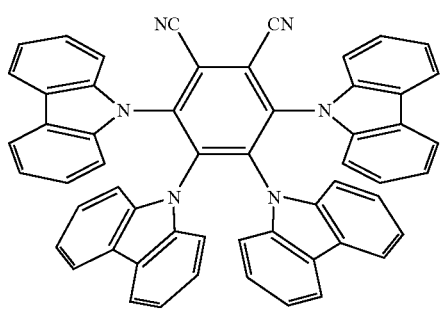

-continued
T13
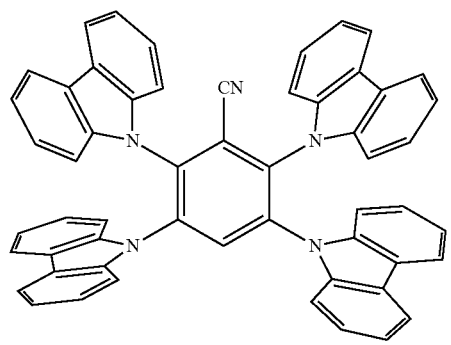
T14
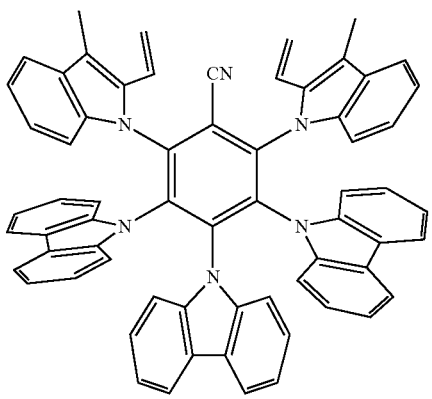
T15
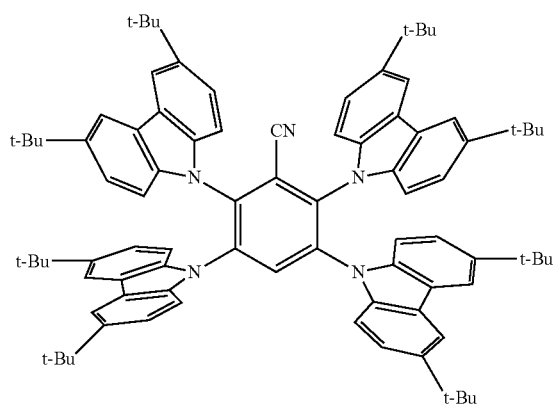
T16
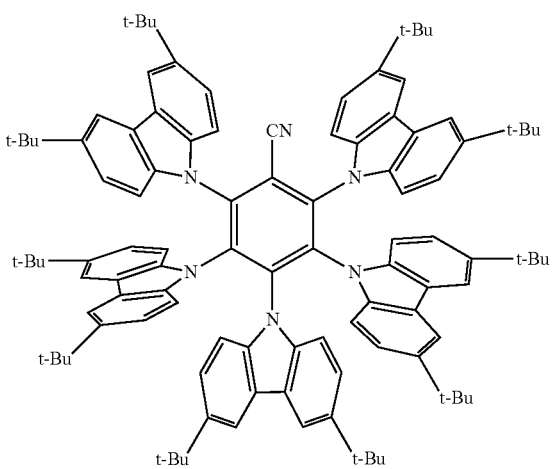
T17
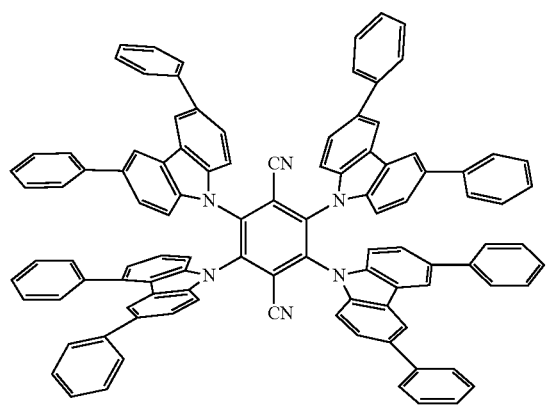
T18
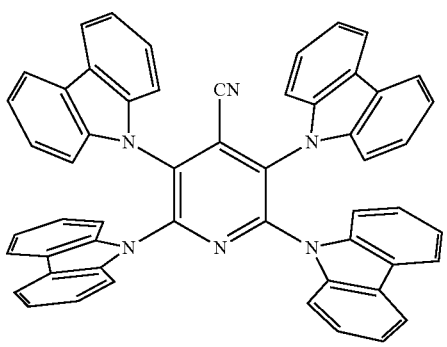
T20
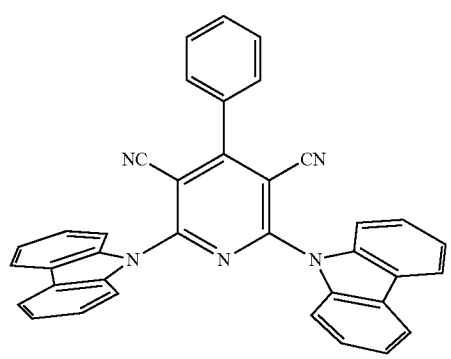
T19
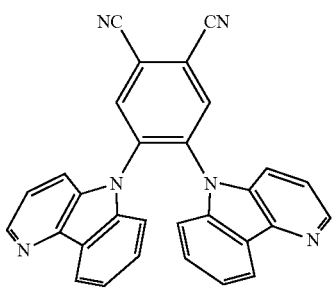

-continued
T21
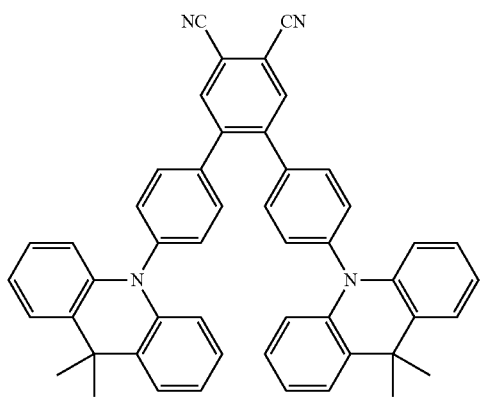
T22
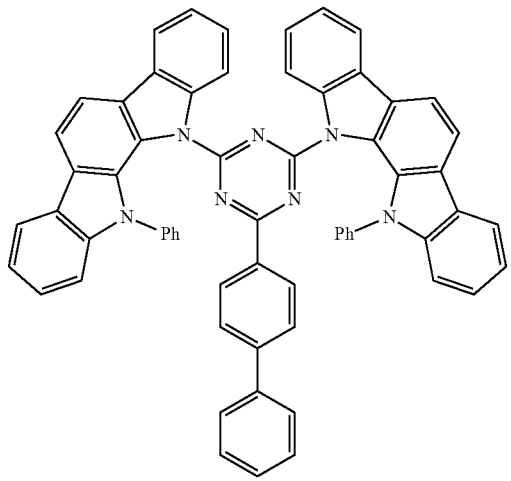
T23
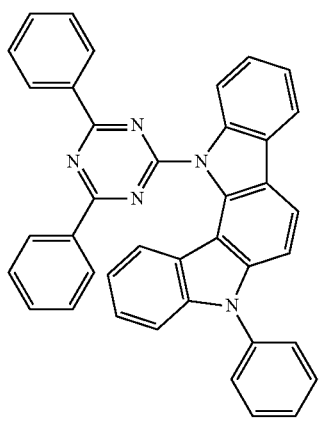
T24
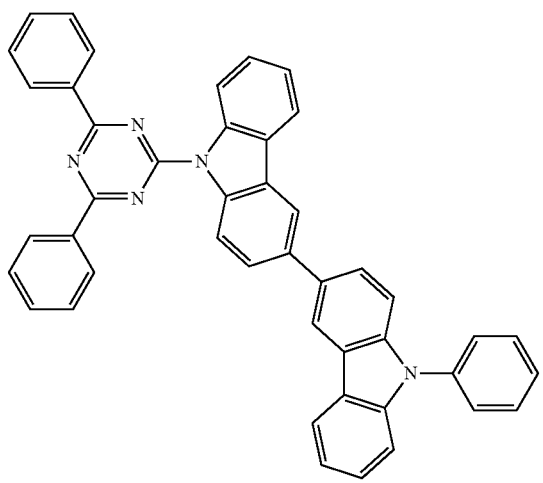
T25
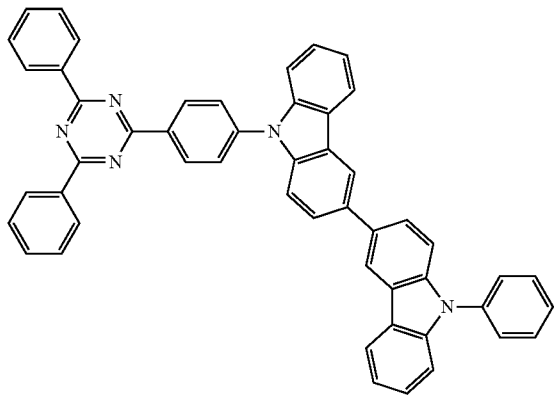
T26
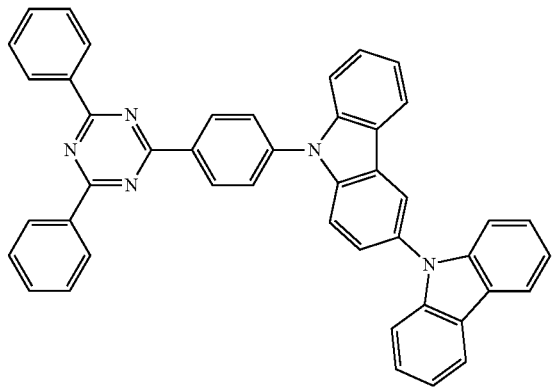

-continued
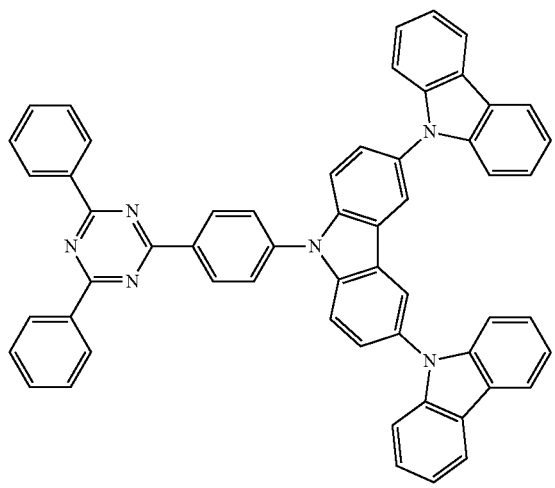
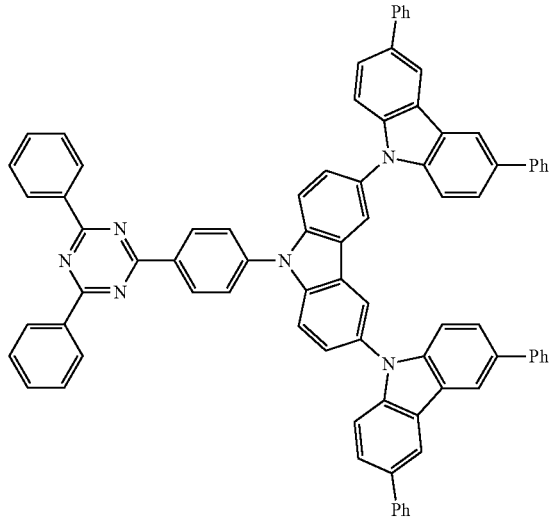
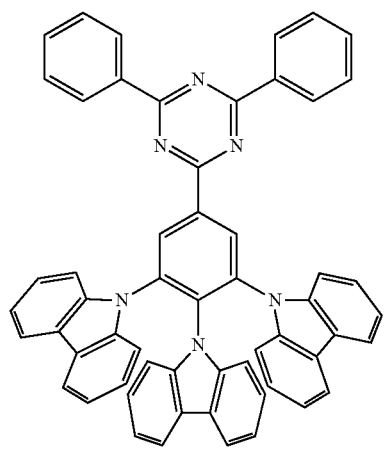
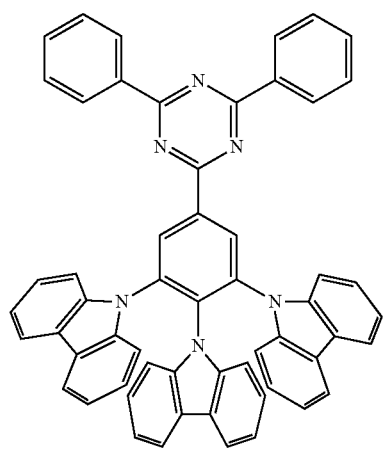
T29

-continued
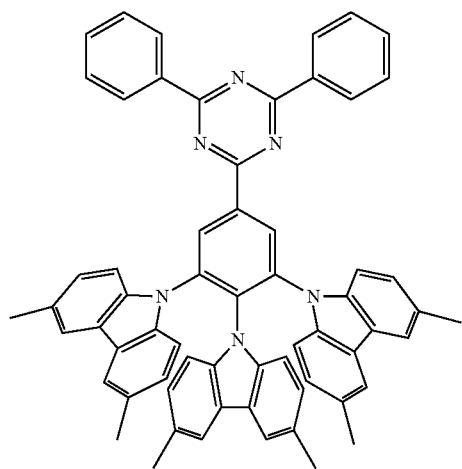
T30
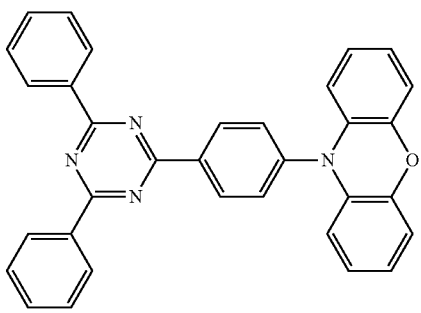
T31
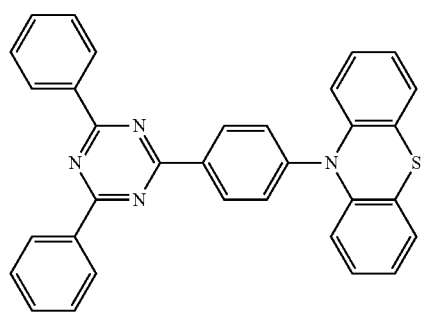
T32
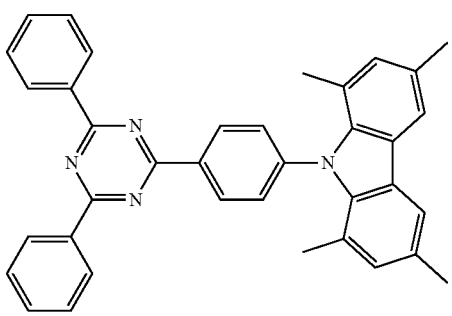
T33
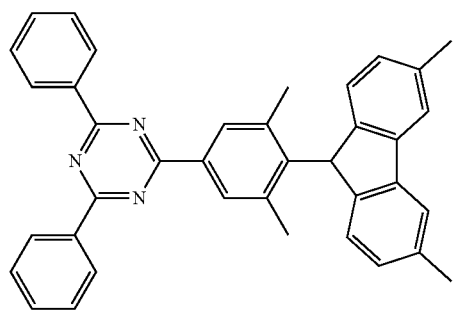
T34
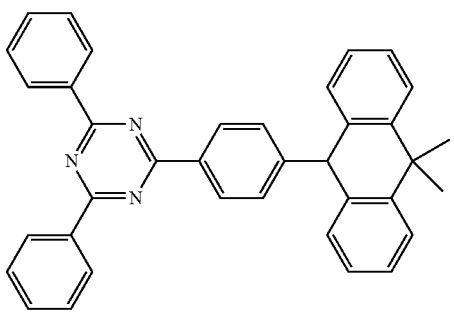
T35
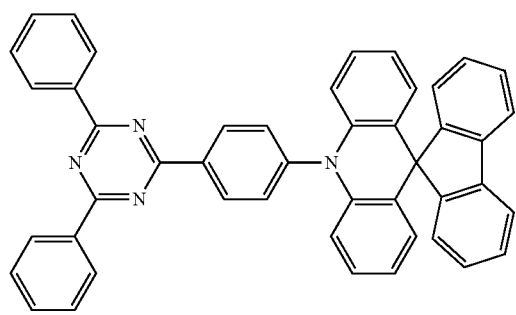
T33

-continued
T36
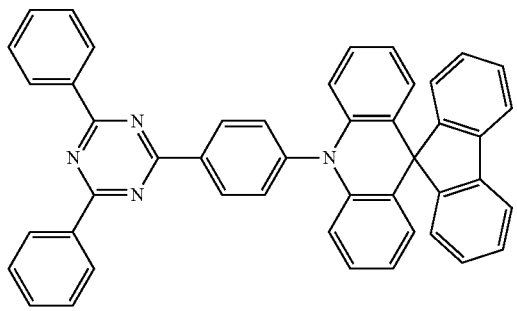
T37
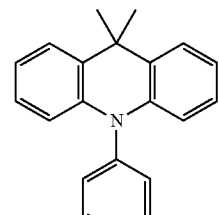
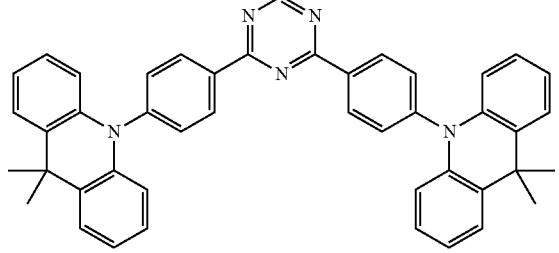
T39
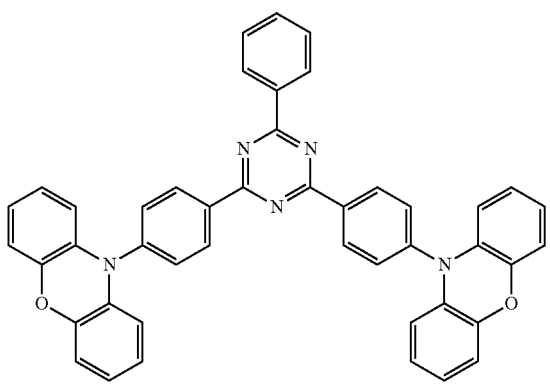
T38
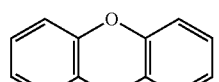
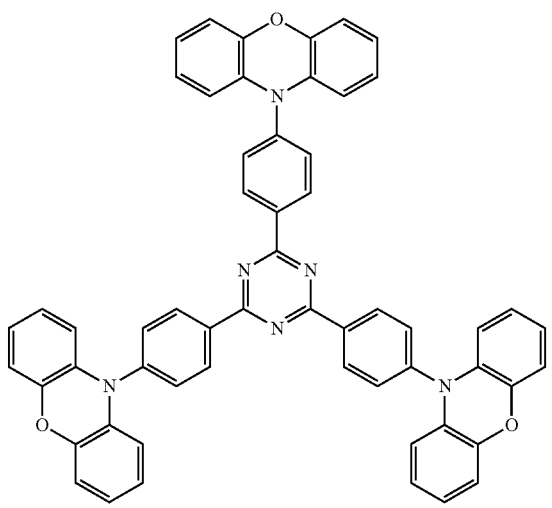
T40
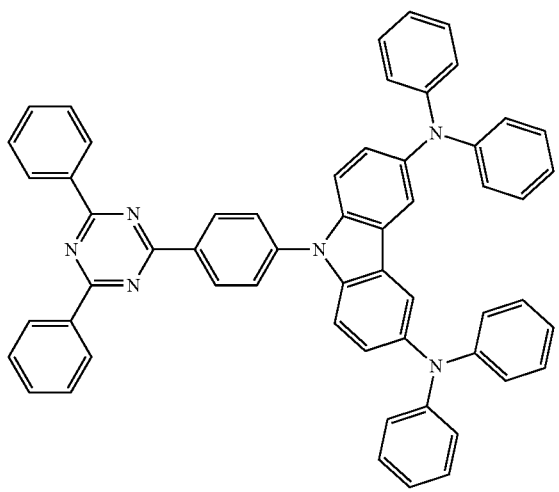
T41
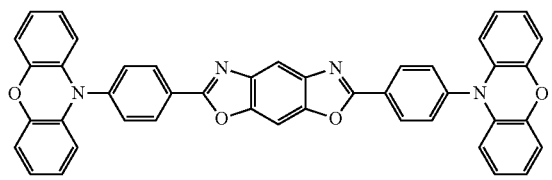

T37
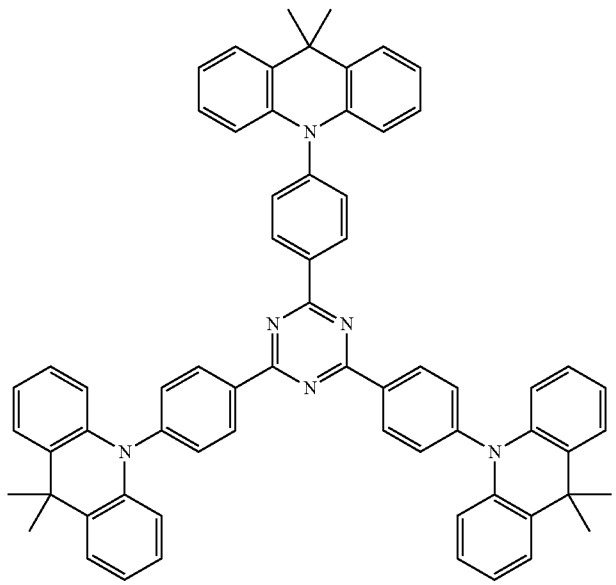
T42
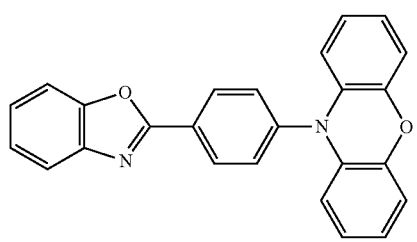
T43
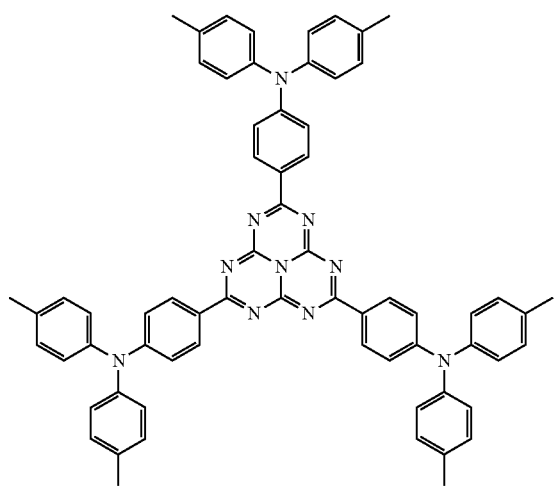
T44
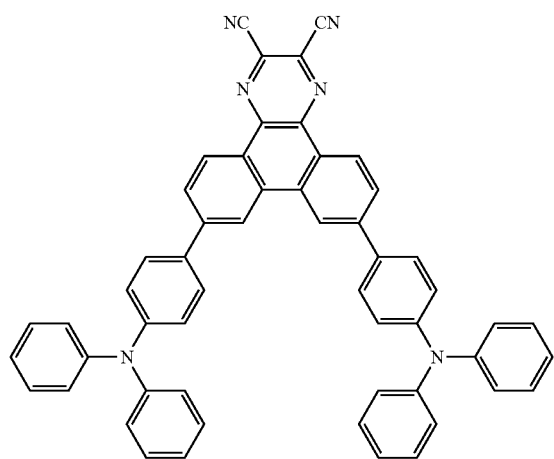

T45
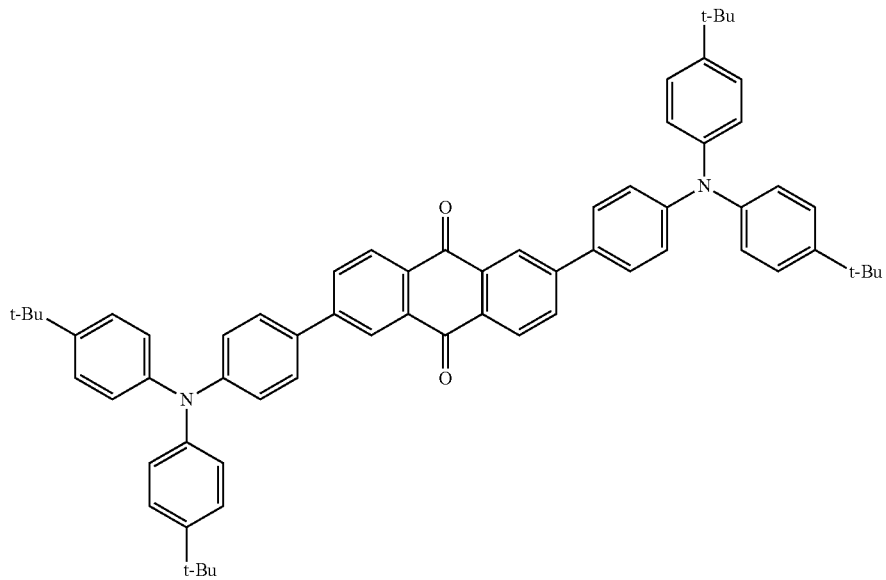
T47
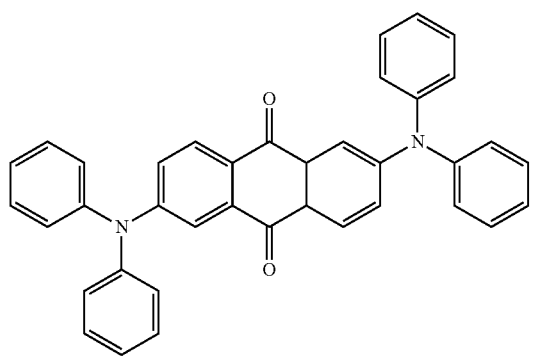
T48
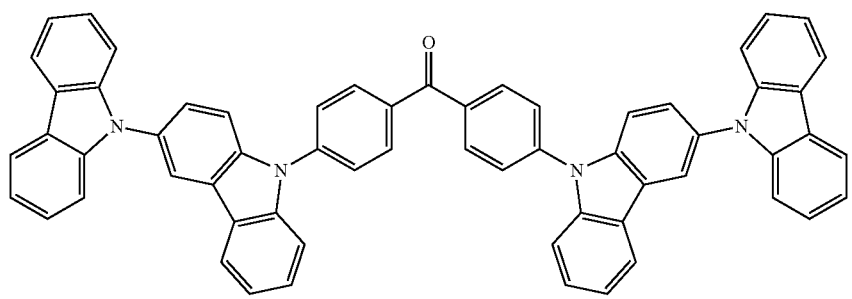
T49 T50
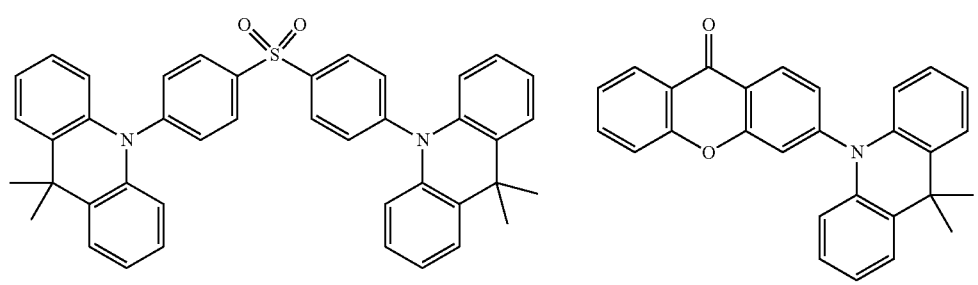

-continued
T51
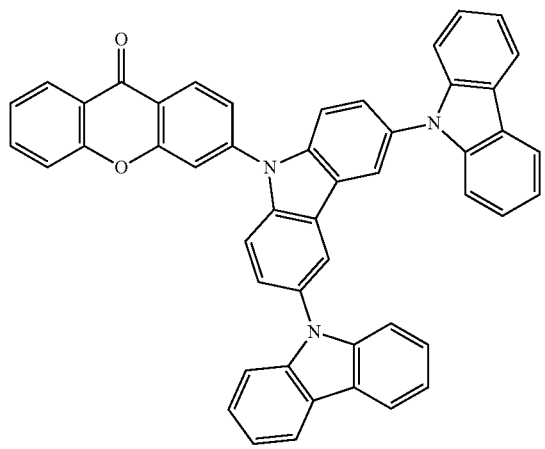
T52
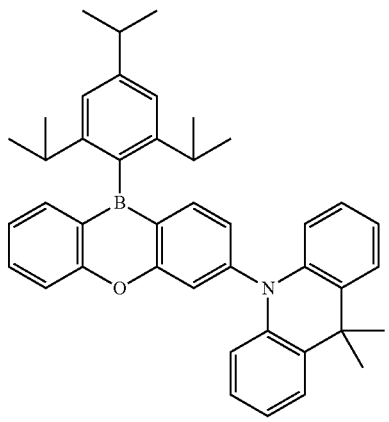
T53
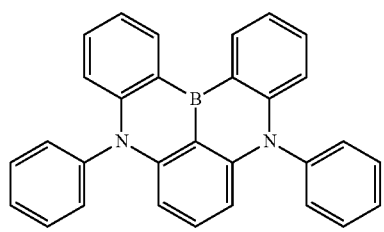
T54
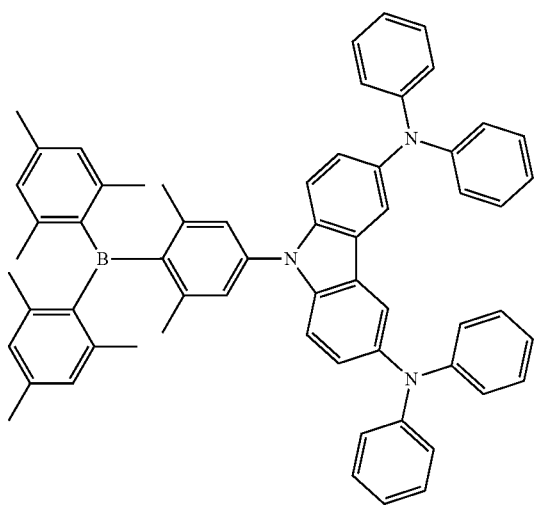
T55
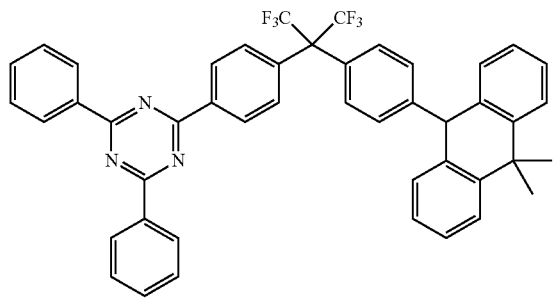
T56
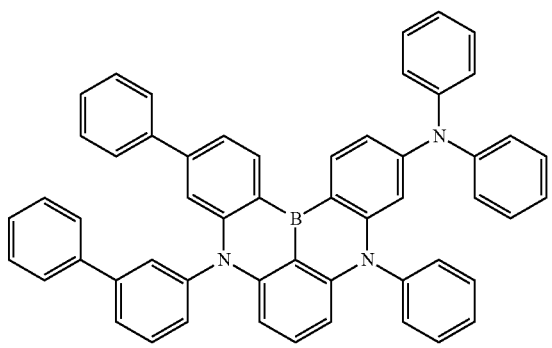

-continued
T57
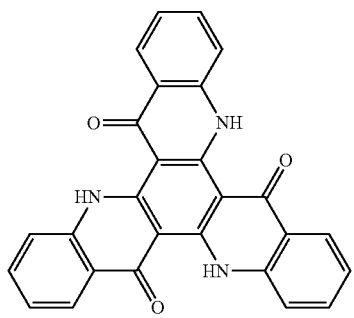
T58
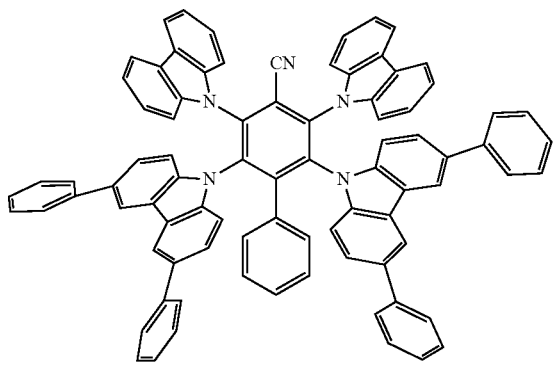
T59
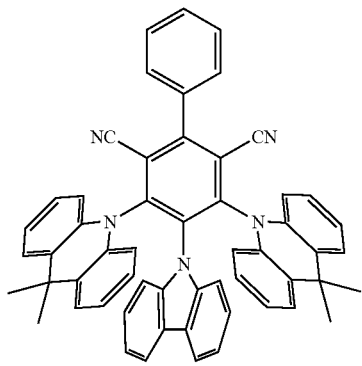
T60
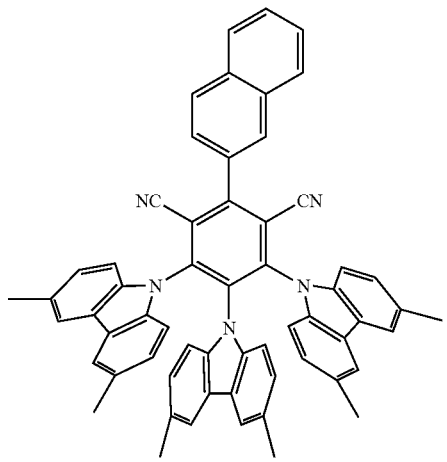
T61
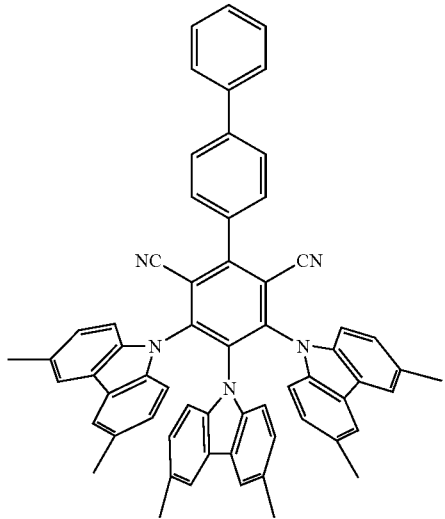
T62
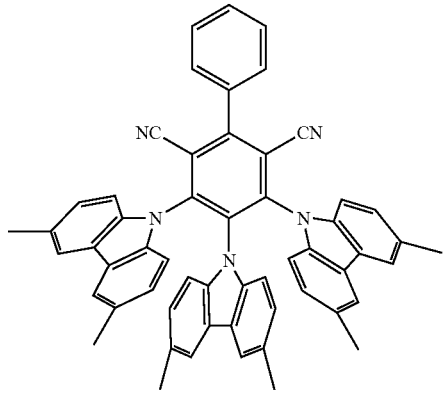

-continued
T63
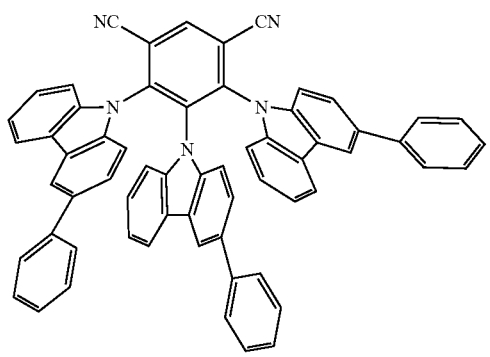
T64
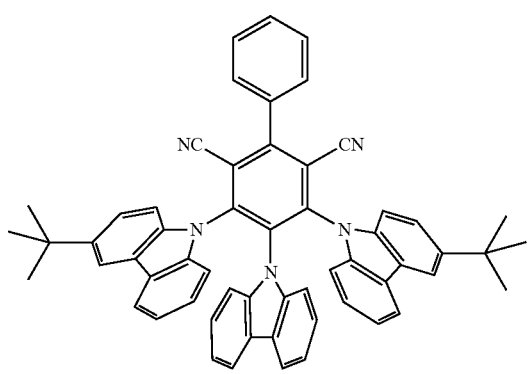
T65
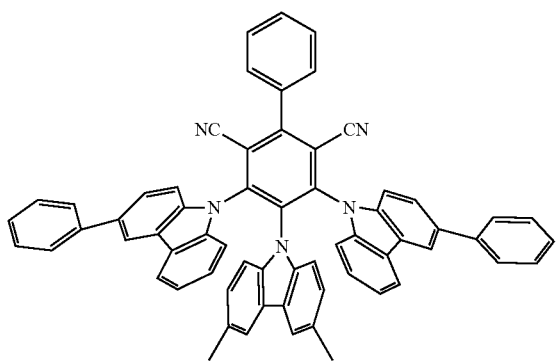
T66
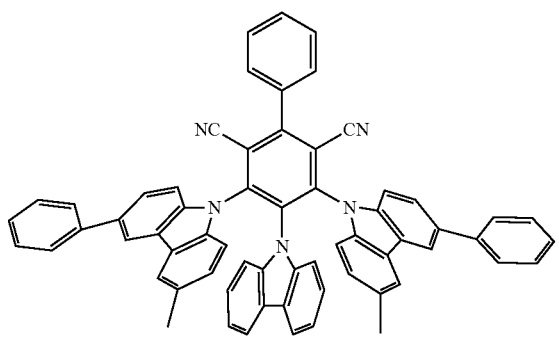
T67
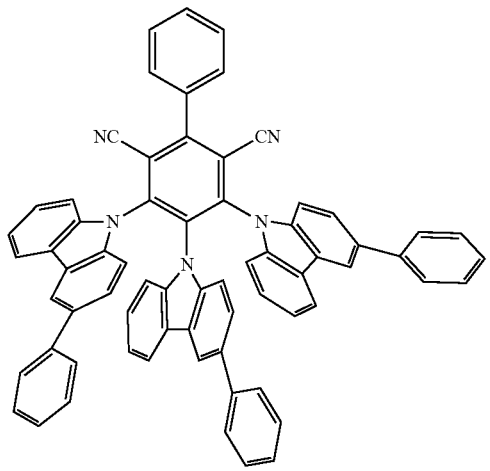
T68
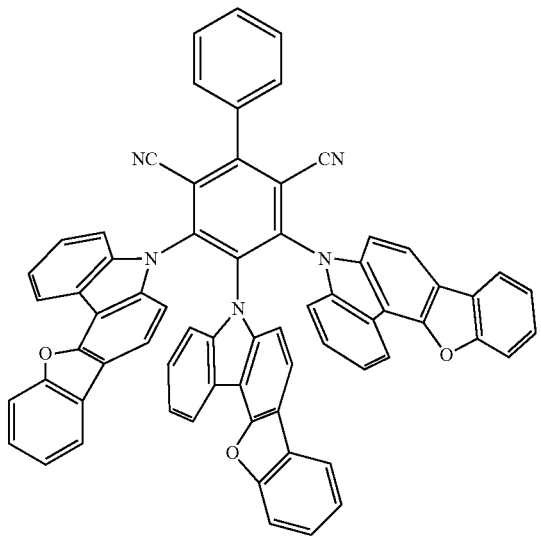

-continued
T69
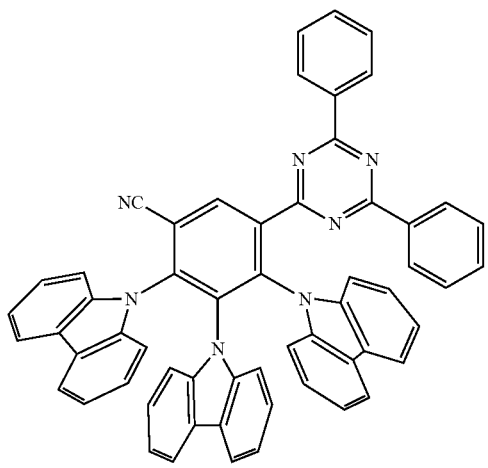
T70
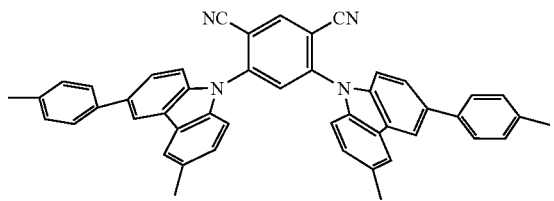
T71
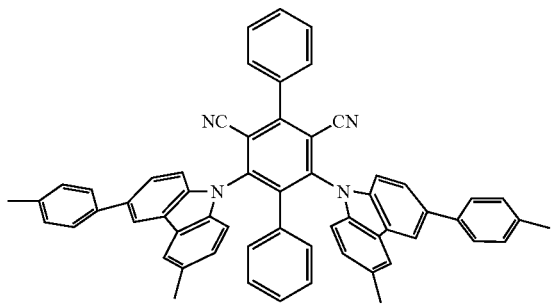
T72
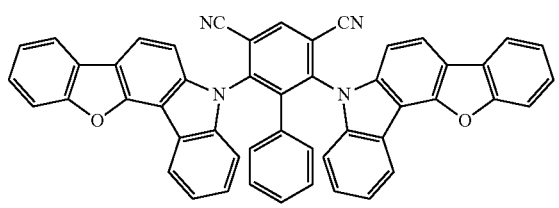
T73
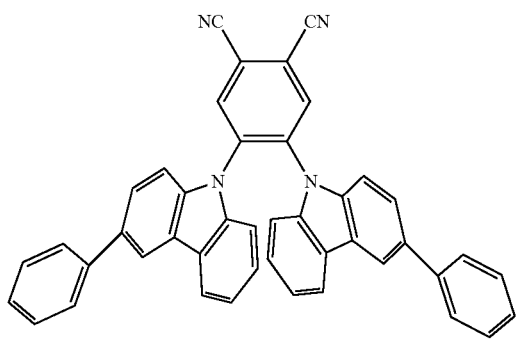
T74
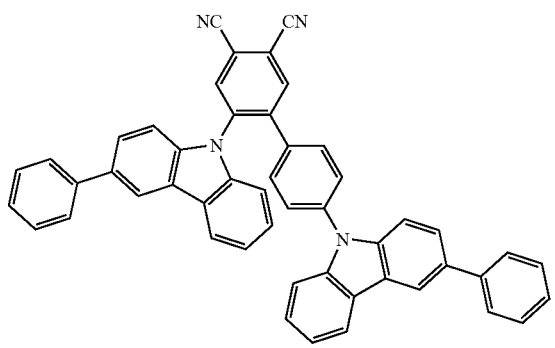
T75
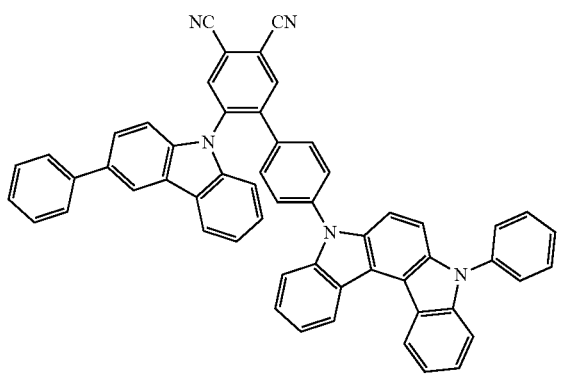
T76
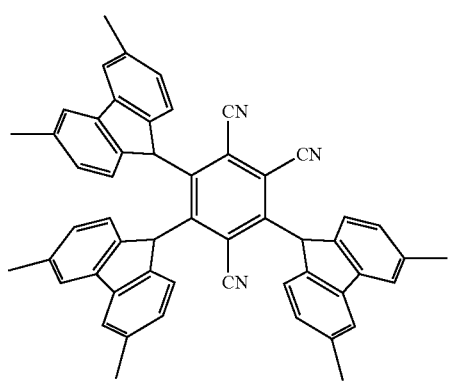

-continued

T77
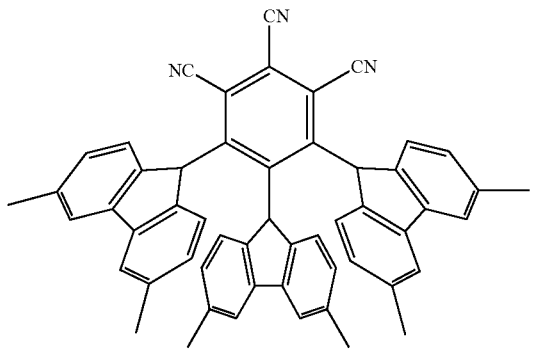

T78
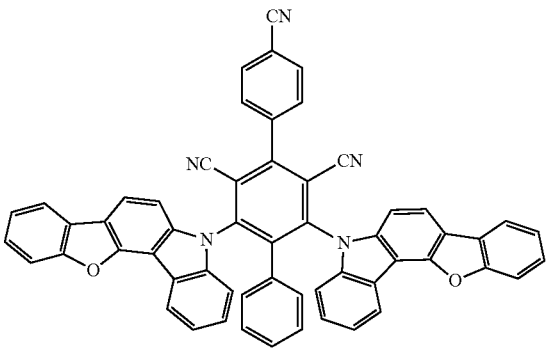

T79
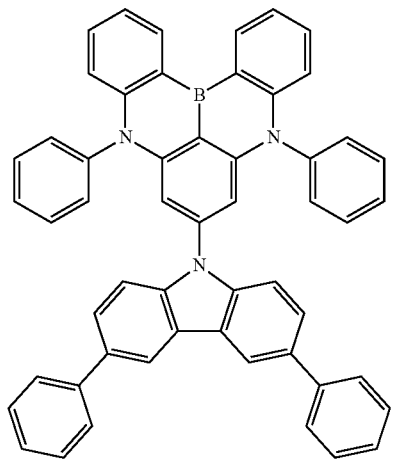

T80
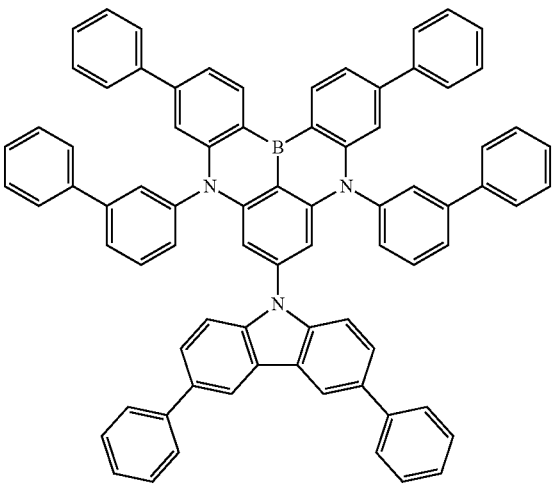

(Composition Containing First Compound and Second Compound)

The composition of the present invention contains a first compound and a second compound. The composition of the present invention may be constituted only of the first compound and the second compound, or may contain a compound other than the first compound and the second compound.

The first compound and the second compound satisfy the relation of the expression (A). Thus, the lowest excited singlet energy level $E_{S1}(1)$ of the first compound is higher than the lowest excited singlet energy level $E_{S1}(2)$ of the second compound.

Accordingly, movement of the excited singlet energy from the first compound to the second compound easily occurs. A difference between $E_{S1}(1)$ and $E_{S1}(2)$, $[E_{S1}(1)-E_{S1}(2)]$, may be, for example, 0.1 eV or more, 0.2 eV or more, 0.3 eV or more, or 0.5 eV or more, and may be 1.2 eV or less, 1.0 eV or less, 0.8 eV or less, or 0.6 eV or less.

The lowest excited triplet energy level $E_{T1}(1)$ of the first compound is preferably higher than the lowest excited triplet energy level $E_{S1}(2)$ of the second compound. Accordingly, the excited triplet energy is confined in the molecule of the second compound, and the generation probability of reverse intersystem crossing from the excited triplet state to the excited singlet state thereof can be increased. As a result, a composition having a high luminous efficiency can be obtained.

The lowest excited singlet energy level $E_{S1}$ and the lowest excited triplet energy level $E_{T1}$ can be determined by the following measurement method. In measurement, a compound to be measured is dissolved in toluene to provide a solution sample or a compound to be measured is subjected to co-deposition together with a host material so that the concentration of the compound to be measured is 6% by weight to provide a film sample. The host material is selected from materials that have a lowest excited singlet energy level higher than $E_{S1}$ of the compound to be measured and have a lowest excited triplet energy level higher than $E_{T1}$ of the compound to be measured. Note that $E_{S1}$ and $E_{T1}$ in this description are values measured using a film sample having a thickness of 100 nm obtained by co-deposition of a compound to be measured together with mCP on an Si substrate so that the concentration of the compound to be measured is 6% by weight.

(1) Lowest Excited Singlet Energy Level $E_{S1}$

A fluorescence spectrum of a sample is measured at a normal temperature (300K). The emission during the period from immediately after incidence of exciting light to 100 nanoseconds after the incidence is integrated to obtain a fluorescence spectrum with the emission intensity on the vertical axis and the wavelength on the horizontal axis. In the fluorescence spectrum, the vertical axis indicates the emission and the horizontal axis indicates the wavelength. In the emission spectrum, a tangent is drawn on a rising portion on the lower wavelength side, and the value of wavelength λedge [nm] at the point at which the tangent is intersected with the horizontal axis is obtained. The value of wavelength is converted into an energy value according to the following conversion equation and the energy value is defined as $E_{S1}$.

Conversion equation: $E_{S1}[eV]=1239.85/\lambda_{edge}$

For measuring the emission spectrum, for example, a nitrogen laser (MNL200, manufactured by Lasertechnik Berlin) can be used as an exciting light source and a streak camera (model C4334, manufactured by Hamamatsu Photonics K.K.) can be used as a detector.

(2) Lowest Excited Triplet Energy Level $E_{T1}$

The same sample as for the lowest excited singlet energy level $E_{S1}$ is cooled to 77[K], and the sample for measuring phosphorescence is irradiated with exciting light (337 nm), and using a streak camera, the intensity of the phosphorescence is measured. The emission during the period from 1 millisecond after the incidence of the exciting light to 10 milliseconds after the incidence is integrated to obtain a phosphorescent spectrum with the emission intensity on the vertical axis and the wavelength on the horizontal axis. A tangent is drawn on a rising portion on the lower wavelength side of the phosphorescent spectrum, and the value of wavelength kedge [nm] at the point at which the tangent is intersected with the horizontal axis is obtained. The value of wavelength is converted into an energy value according to the following conversion equation, and the energy value is defined as $E_{T1}$.

Conversion equation: $E_{T1}[eV]=1239.85/\lambda_{edge}$

The tangent on a rising portion on the lower wavelength side of the phosphorescent spectrum is drawn in the following manner. A tangent at each point on the phosphorescent spectrum curve is considered toward the longer wavelength side while moving, on the spectrum curve, from the lower wavelength side of the phosphorescent spectrum to the maximum value on the lowest wavelength side of all the maximum values of the spectrum. The slope of the tangent increases as the curve rises (that is, as the vertical axis increases). A tangent drawn at a point at which the slope is the maximum value is taken as a tangent on a rising portion on the lower wavelength side of the phosphorescent spectrum. Note that the maximal point having a peak intensity of 10% or less of the maximum peak intensity of the spectrum is not included in the maximum values on the lowest wavelength side, and a tangent drawn at a point at which the slope is the maximum value which point is closest to the maximum value of the lowest wavelength side is taken as the tangent on a rising portion of the lower wavelength side of the phosphorescent spectrum.

In the composition of the present invention, the first compound is to satisfy the expression (1a), the second compound is to satisfy the expression (2b), and the first compound and the second compound is to satisfy the relation of the expression (A).

In a preferred embodiment, in the composition of the present invention, the first compound satisfies the expression (1a) and the expression (1c), the second compound satisfies the expression (2b), and the first compound and the second compound satisfy the relation of the expression (A).

In another preferred embodiment, in the composition of the present invention, the first compound satisfies the expression (1a), the second compound satisfies the expression (2a) and the expression (2b), and the first compound and the second compound satisfy the relation of the expression (A).

In another preferred embodiment, in the composition of the present invention, the first compound satisfies the expression (1a) and the expression (1c), the second compound satisfies the expression (2a) and the expression (2b), and the first compound and the second compound satisfy the relation of the expression (A).

Relative to 100 parts by weight of the content of the first compound contained in the composition of the present invention, the content of the second compound is preferably 0.01 parts by weight or more, for example, the content can be selected from the ranges of 0.1 parts by weight or more, 1 part by weight or more, 3 parts by weight or more, 5 parts by weight or more, and 9 parts by weight or more. The content of the second compound relative to 100 parts by weight of the content of the first compound can be selected from, for example, the ranges of less than 50 parts by weight, 30 parts by weight or less, 20 parts by weight or less, 15 parts by weight or less, 10 parts by weight or less, 6 parts by weight or less, 2 parts by weight or less, and 0.5 parts by weight or less. For example, the content may be selected from the range of 30 to 70 parts by weight, or may be selected from the range of 40 to 55 parts by weight.

The content of the first compound in the composition of the present invention is preferably 30% by weight or more, and more preferably 50% by weight or more. For example, the content can be in the range of 70% by weight or more, 80% by weight or more, 90% by weight or more, 95% by weight or more, or 99% by weight or more. The content of the first compound in the composition of the present invention is preferably 99.99% by weight or less, and, for example, can be in the range of 99.9% by weight or less, 99% by weight or less, 95% by weight or less, 85% by weight or less, 75% by weight or less, 55% by weight or less, or 35% by weight or less. For example, the content may be selected from the range of 50 to 90% by weight, or may be selected from the range of 60 to 80% by weight.

The composition of the present invention preferably contains no metal element, and preferably contain no heavy metal element. The composition of the present invention is preferably constituted only of atoms selected from the group consisting of a carbon atom, a hydrogen atom, a nitrogen atom, an oxygen atom, a sulfur atom, and a silicon atom, is preferably constituted only of atoms selected from the group consisting of a carbon atom, a hydrogen atom, a nitrogen atom, an oxygen atom, and a sulfur atom, is preferably constituted only of atoms selected from the group consisting of a carbon atom, a hydrogen atom, a nitrogen atom, and an oxygen atom, and is preferably constituted only of atoms selected from the group consisting of a carbon atom, a hydrogen atom, and a nitrogen atom.

The composition of the present invention can be adjusted so that, in the emission from the composition of the present invention, the amount of emission from the second compound is the largest. In this case, the amount of emission from the second compound is preferably 50% or more of the entire amount of emission from the composition, and can be adjusted to 70% or more, 90% or more, 95% or more, 99% or more, 99.9% or more, or 100%.

Note that, in this description, when an amount of emission from a composition is mentioned, it shows an amount of emission when the composition is made into a thin film, the thin film is inserted between a pair of electrodes to produce an element, and the element is subjected to current excitation.

(Third Compound)

The composition of the present invention may contain, in addition to the first compound and the second compound, a third compound satisfying the following expression (B).

$$E_{S1}(1) > E_{S1}(2) > E_{S1}(3) \qquad \text{expression (B)}$$

In the expression (B), $E_{S1}(1)$ represents the lowest excited singlet energy level of the first compound. $E_{S1}(2)$ represents the lowest excited singlet energy level of the second compound, and $E_{S1}(3)$ represents the lowest excited singlet energy level of the third compound.

The difference between $E_{S1}(2)$ and $E_{S1}(3)$, $[E_{S1}(2)-E_{S1}(3)]$, may be, for example, 0.1 eV or more, 0.2 eV or more, 0.3 eV or more, or 0.5 eV or more, and may be 1.2 eV or less, 1.0 eV or less, 0.8 eV or less, or 0.6 eV or less. When the third compound satisfying the expression (B) is adopted, the excited singlet energy of the second compound easily moves to the third compound, the energy of the excited singlet state generated by reverse intersystem crossing of the second compound can be efficiently used for light emission of the third compound.

The third compound is preferably a fluorescence material. "Fluorescence material" in the present invention means an organic material that emits fluorescence when a solution sample in toluene or dichloromethane or a deposited film sample is irradiated with exciting light at 20° C. Here, "fluorescence" is light emitted in deactivation from an excited singlet state to a ground singlet state, and can be distinguished from phosphorescence in that fluorescence is not extinguished by introduction of a triplet quencher or oxygen, the triplet quencher having a lowest excited singlet energy level $S_{1,q}$ and a lowest excited triplet energy level $T_{1,q}$ that satisfy the following relation with respect to the lowest excited singlet energy level $S_{1,f}$ and the lowest excited triplet energy level $T_{1,f}$ of a fluorescence material.

$$S_{1,q} > S_{1,f}$$

$$T_{1,q} < T_{1,f}$$

The fluorescence material in the present invention may be a material that emits phosphorescence together with fluorescence, but the intensity of the fluorescence in this case is preferably 9 times or more higher than the intensity of the phosphorescence.

As the third compound, a compound having a fluorescence emission lifetime (I) less than 200 ns (nanoseconds) may be adopted, or a delayed fluorescent material having a fluorescence emission lifetime (T) of 200 ns (nanoseconds) or more may be adopted.

About the description of the fluorescence emission lifetime (T), one can refer to the description of the fluorescence emission lifetime ($\tau$) of the second compound.

The third compound preferably satisfies the following expression (3b).

$$\Delta E_{ST}(3) < 0.20 \text{ eV} \qquad \text{expression (3b)}$$

In the expression (3b), $\Delta E_{ST}(3)$ is a difference between the lowest excited singlet energy level $E_{S1}(3)$ of the third compound and the lowest excited triplet energy level $E_{T1}(3)$ of the third compound.

$\Delta E_{ST}(3)$ of the third compound can be in the range of, for example, less than 0.15 eV, less than 0.10 eV, less than 0.05 eV, or less than 0.01 eV. A third compound having a smaller $\Delta E_{ST}(3)$ tends to more easily undergo reverse intersystem crossing, and more effectively exhibits the action of converting the excited triplet state to the excited singlet state.

The third compound may be a material constituted of a single compound that satisfies the expression (B), or may be a material constituted of two or more compounds that form an exciplex, the lowest excited singlet energy level $E_{S1}$ of the exciplex satisfying the expression (B). When the third compound forms an exciplex, the difference between the lowest excited singlet energy level $E_{S1}$ and the lowest excited triplet energy level $E_{T1}$ of the exciplex is preferably less than 0.20 eV. The third compound is preferably a compound containing no metal element, is preferably a compound containing no heavy metal element, is preferably a compound constituted only of atoms selected from the group consisting of a carbon atom, a hydrogen atom, a nitrogen atom, an oxygen atom, a sulfur atom, and a silicon atom, is preferably a compound constituted only of atoms selected from the group consisting of a carbon atom, a hydrogen atom, a nitrogen atom, an oxygen atom, and a sulfur atom, is preferably a compound constituted only of atoms selected from the group consisting of a carbon atom, a hydrogen atom, a nitrogen atom, and an oxygen atom, and is preferably a compound constituted only of atoms selected from the group consisting of a carbon atom, a hydrogen atom, and a nitrogen atom.

When the composition of the present invention contains the third compound, the content of the third compound is preferably less than the content of the first compound.

The content of the third compound is preferably less than the content of the second compound. The content of the third compound relative to 100 parts by weight of the total amount of the first compound and the second compound is preferably 0.01 parts by weight or more, and, for example, can be selected from the ranges of 0.1 parts by weight or more, 1 part by weight or more, 3 parts by weight or more, 5 parts by weight or more, and 9 parts by weight or more. The content of the third compound relative to 100 parts by weight of the total amount of the first compound and the second compound, for example, can be selected from the ranges of 30 parts by weight or less, 20 parts by weight or less, 15 parts by weight or less, 10 parts by weight or less, 6 parts by weight or less, 2 parts by weight or less, and 0.5 parts by weight or less. For example, the content may be selected from the range of 0.01 to 5 parts by weight, or may be selected from the range of 0.1 to 3% by weight.

When the composition of the present invention contains the third compound, adjustment can be made so that the amount of emission from the third compound is the largest in the emission from the composition of the present invention. In this case, the amount of emission from the third compound is preferably 50% or more of the entire amount of emission from the composition, and can be adjusted to 70% or more, 90% or more, 95% or more, 99% or more, 99.9% or more, or 100%.

Even when the composition of the present invention contains the third compound, adjustment can be made so that the amount of emission from the second compound is the largest in the emission from the composition of the present invention. In this case, the amount of emission from the second compound may be adjusted to 50% or more, 70% or more, 90% or more, 95% or more, 99% or more, or 99.99% or more of the entire amount of emission from the composition, or the amount of emission from the third compound may be adjusted within the range of 0.01 to 50%, within the range of 0.01 to 30%, within the range of 0.01 to 10%, within the range of 0.01 to 5%, or within the range of 0.01 to 1%.

The amount of emission from the second compound and the third compound can be controlled by adjusting the types and contents of the second compound and the third compound.

The emission wavelength of the third compound is not particularly limited, and can be appropriately selected according to the intended use of the composition of the present invention. For example, when the composition of the present invention is used in a light emitting layer of an organic light emitting element for image display or color display, the third compound is preferably a compound having a maximum emission wavelength in a red region (620 to 750 nm), a green region (495 to 570 nm), or a blue region (450 to 495 nm).

As the third compound, for example, a compound having a multiple resonance effect, such as an anthracene derivative, a tetracene derivative, a naphthacene derivative, a pyrene derivative, a perylene derivative, a chrysene derivative, a rubrene derivative, a coumarin derivative, a pyran derivative, a stilbene derivative, a fluorene derivative, an anthryl derivative, a pyrromethene derivative, a terphenyl derivative, a terphenylene derivative, a fluoranthene derivative, an amine derivative, a quinacridone derivative, an oxadiazole derivative, a malononitrile derivative, a pyran derivative, a carbazole derivative, a julolidine derivative, a thiazole derivative, and a compound having a boron-containing polycyclic aromatic backbone, for example, a diazaboranaphthoanthracene, can be used. The exemplified backbones may have a substituent or may not have a substituent. The exemplified backbones may be combined with each other.

As specific examples of the third compound, the compounds mentioned as specific examples of the second compound can be mentioned. However, the third compound is to be selected so as to satisfy the relation of the expression (B) with respect to the second compound. A compound used as the third compound preferably shows a PL emission quantum yield of 60% or more, more preferably 80% or more. A compound used as the third compound preferably shows an instant fluorescence lifetime of 50 ns or less, more preferably 20 ns or less. The instant fluorescence lifetime here means, for a compound exhibiting thermally activated delayed fluorescence, an emission lifetime of a component that attenuates fastest of all the multiple exponentially attenuating components observed in a measurement of emission lifetime. A compound used as the third compound preferably has a fluorescence emission rate from S1 to the ground state that is higher than the intersystem crossing rate from S1 to T1. About a method of calculating the rate constant of the compound, one can refer to a known literature about thermally activated delayed fluorescent materials (H. Uoyama, et al., Nature 492, 234 (2012), K. Masui, et al., Org. Electron. 14, 2721, (2013), etc.).

As specific examples of other compounds that can be used as the third compound, the compounds described below can be exemplified. In the structures of the exemplified compounds, t-butyl and t-Bu both represent a tertiary butyl group. However, in the present invention, the compound that can be used as the third compound is not to be limitedly construed by the specific examples.

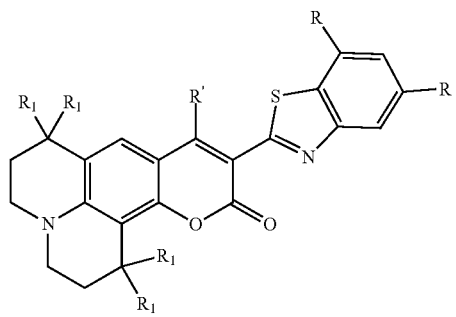

F1: R1=R=R'= H
F2: R1=CH$_3$,R=R'=H
F3: R1=CH$_3$,R=H; R' =CH$_3$
F4: R1=CH$_3$,R=t-butyl; R' = H

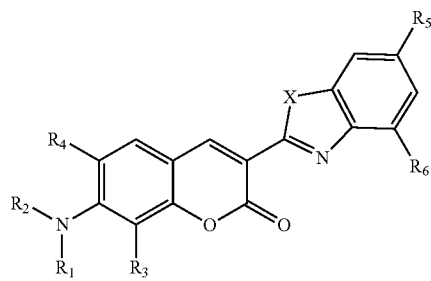

F5: R$_{1-2}$=CH$_3$, R$_{3-6}$=H, X=S
F6: R$_{1-2}$=CH$_3$, R$_{3-6}$=H, X=O

-continued
F7
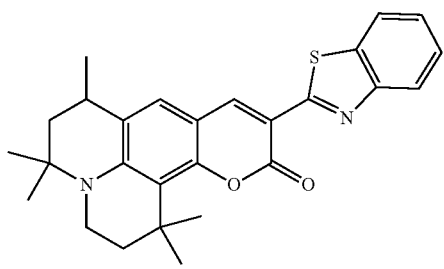
F8
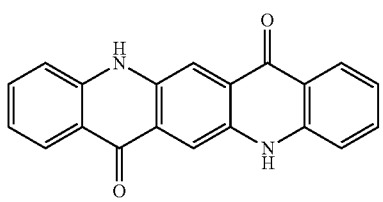
F9
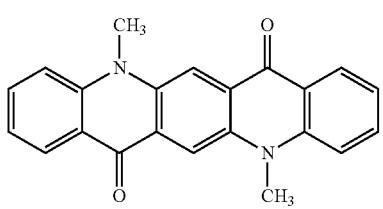
F10
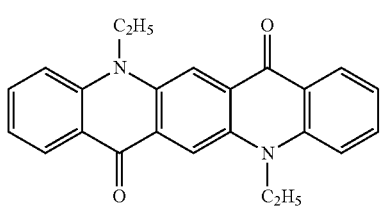
F11
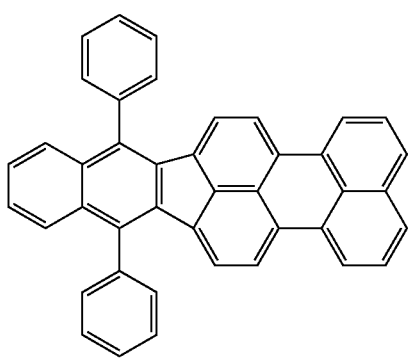
F12
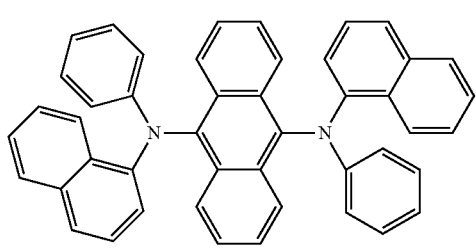

-continued
F13
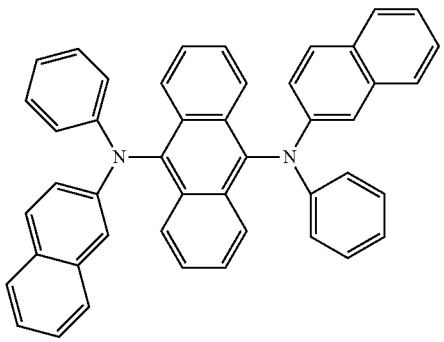
F14
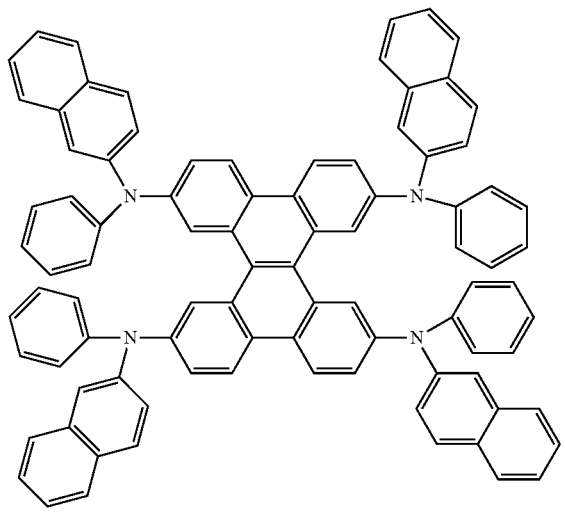
F15
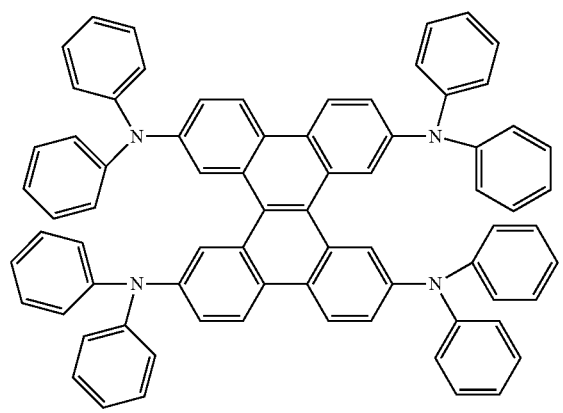
F16
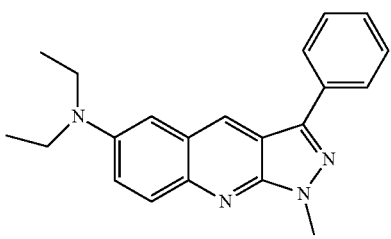

-continued
F17
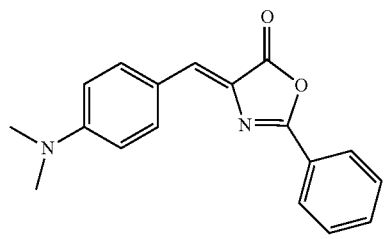
F18
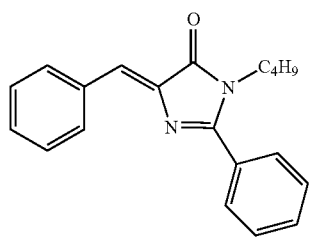
F19
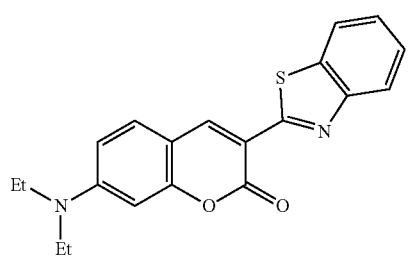
F20
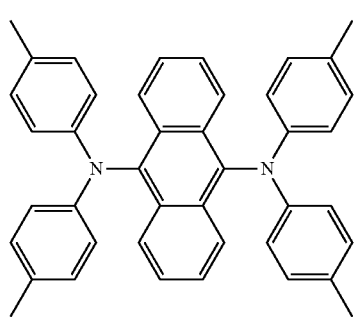
F21
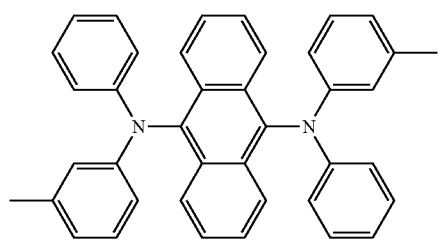
F22
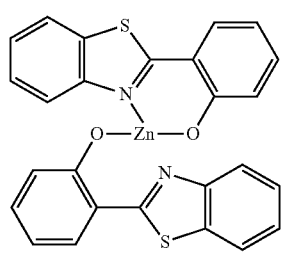

-continued
F23
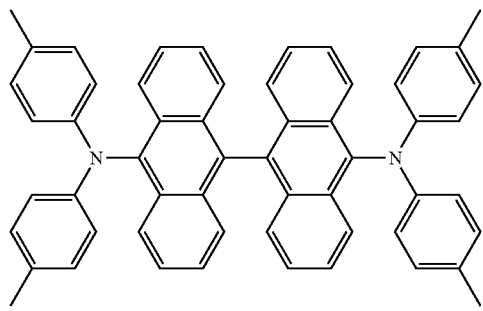
F24
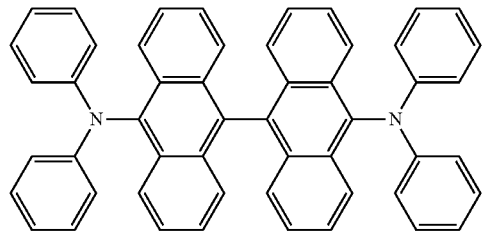
F25
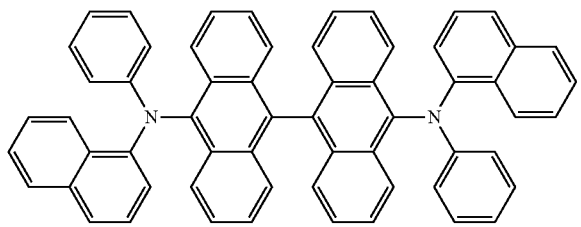
F26
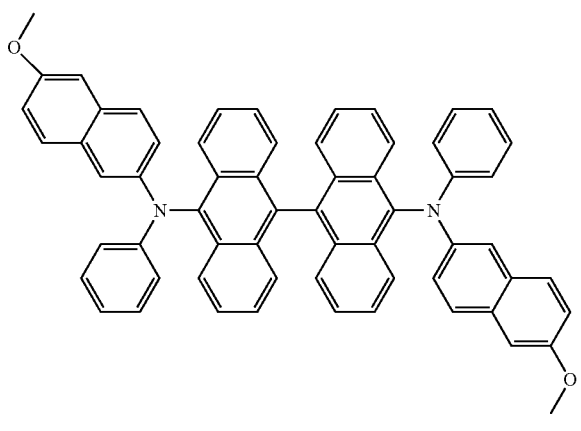
F27
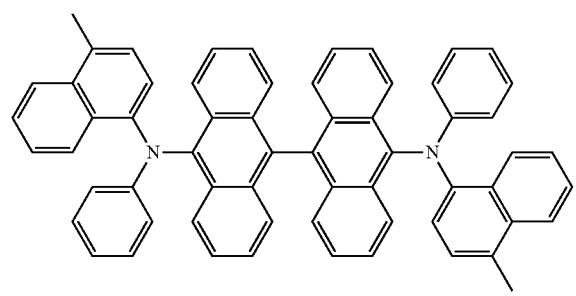

-continued
F28
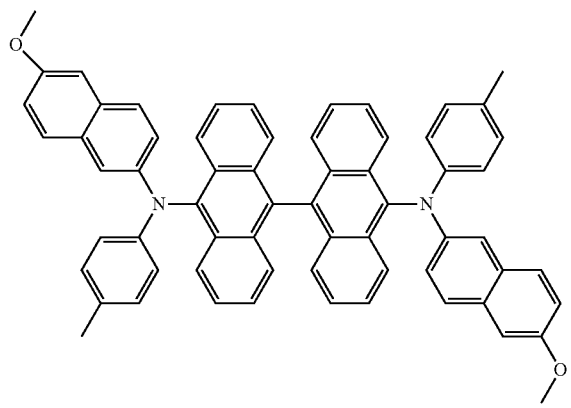
F29
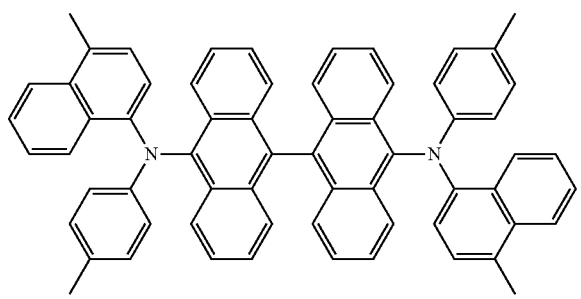
F30
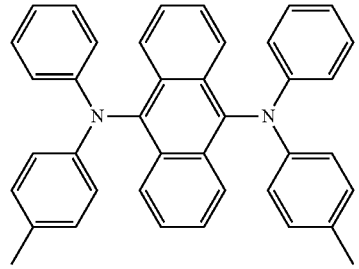
F31
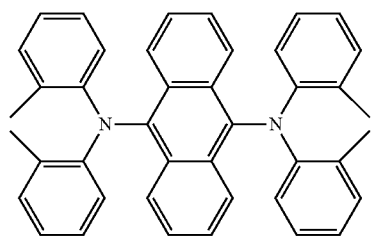
F32
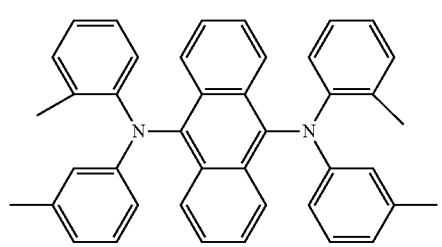

-continued
F33
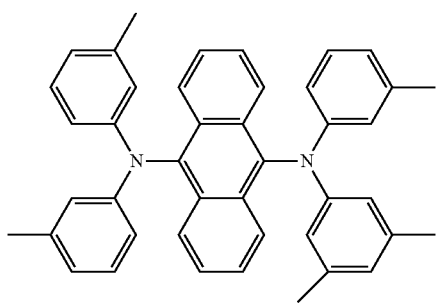
F34
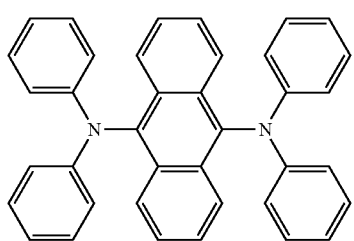
F35
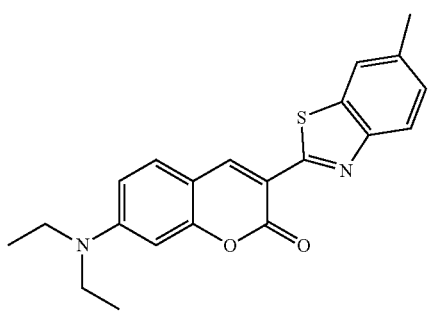
F36
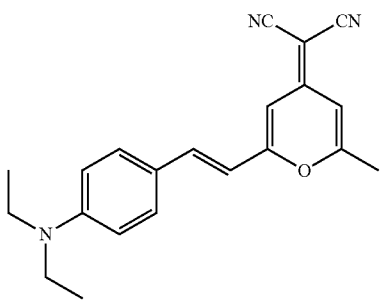
F37
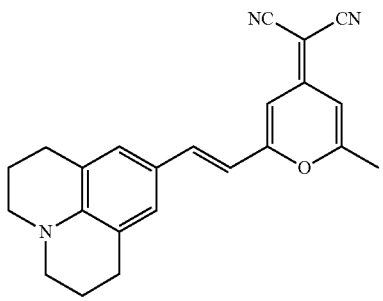

-continued
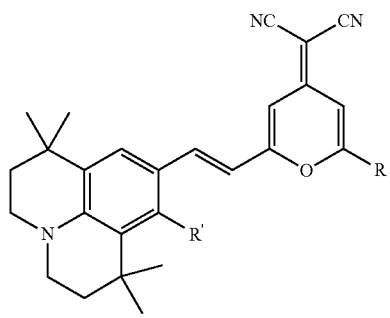
F38: R= t-butyl; R' = H
F39: R= iso-propyl; R' = H
F40: R= t-butyl; R' = OCH₃
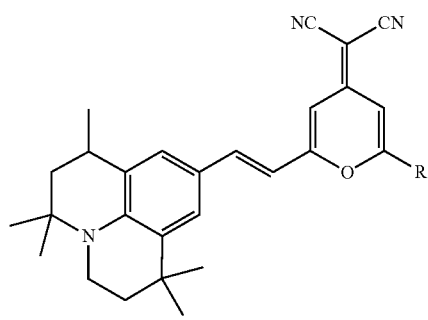
F41: R= CH₃
F42: R= C₂H₅
F43: R= iso-propyl
F44: R= t-butyl
F45
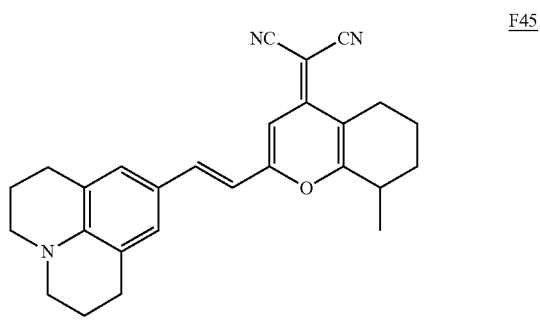
F46
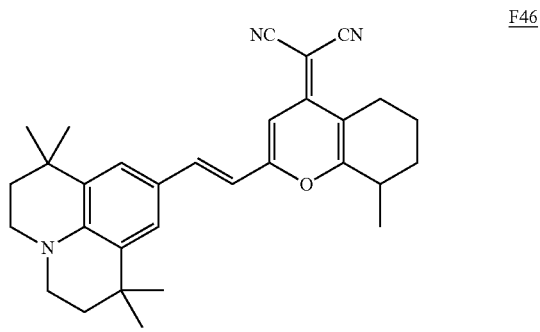

-continued
F47
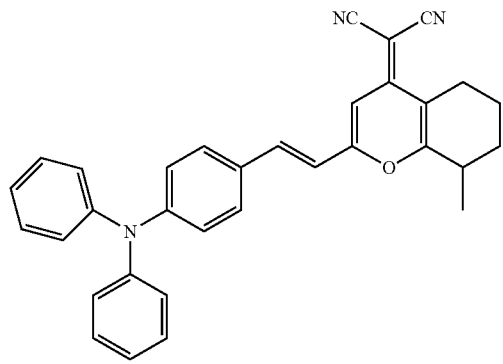
F48
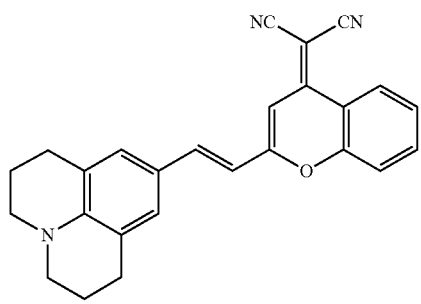
F49
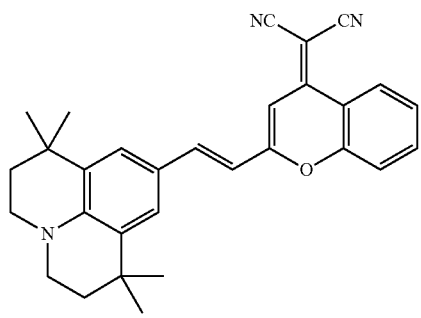
F50
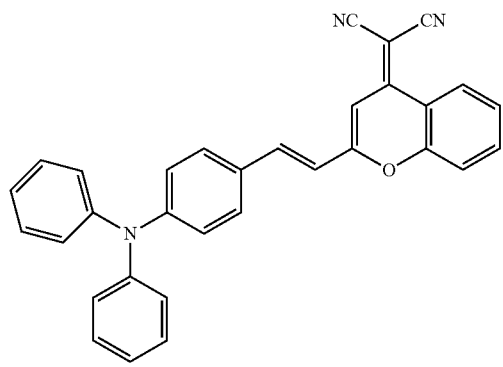
F51
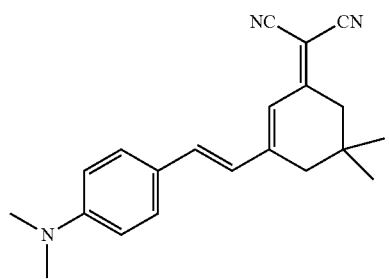

-continued
F52
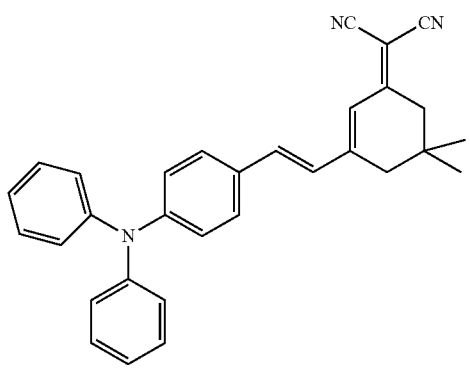
F53
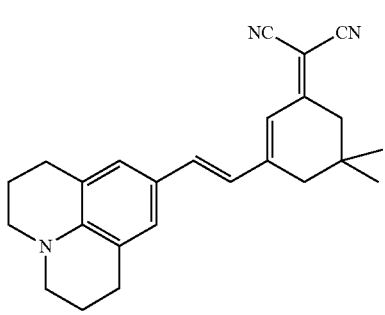
F54
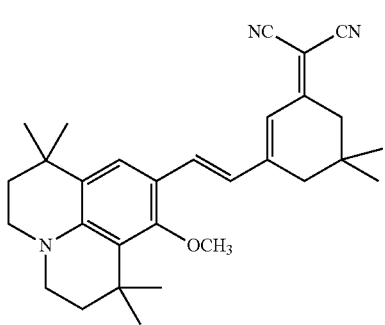
F55
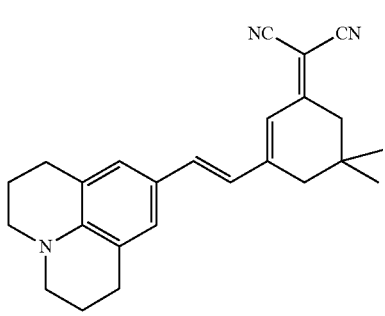
F55
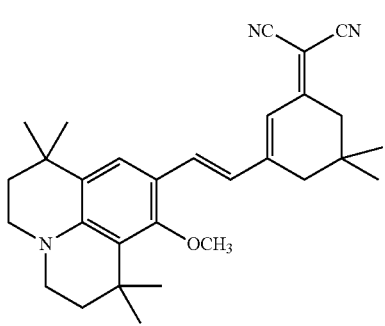

-continued
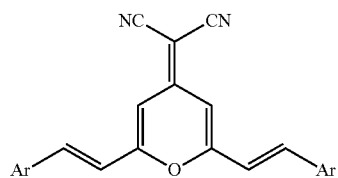
Ar=
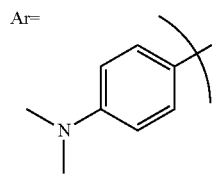
F56
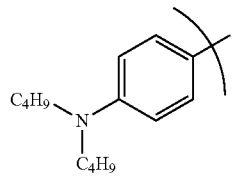
F57
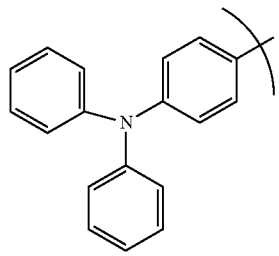
F58
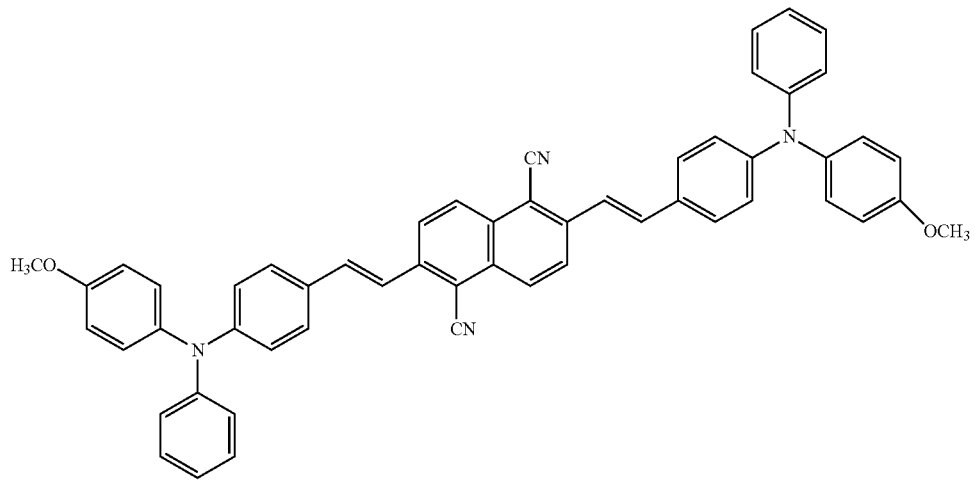
F59
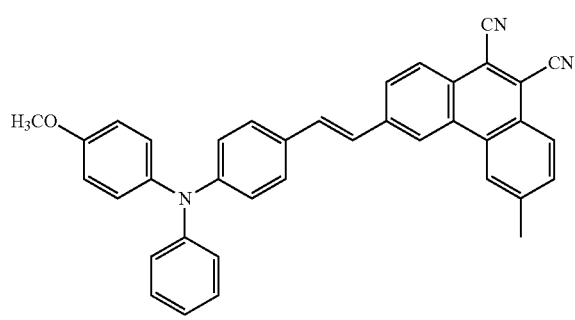
F60

-continued
F61
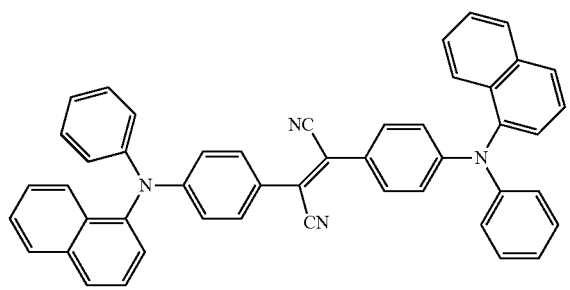
F62
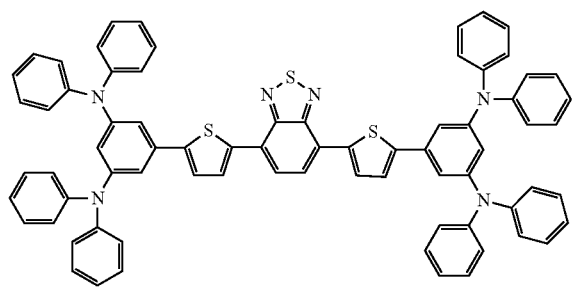
F63
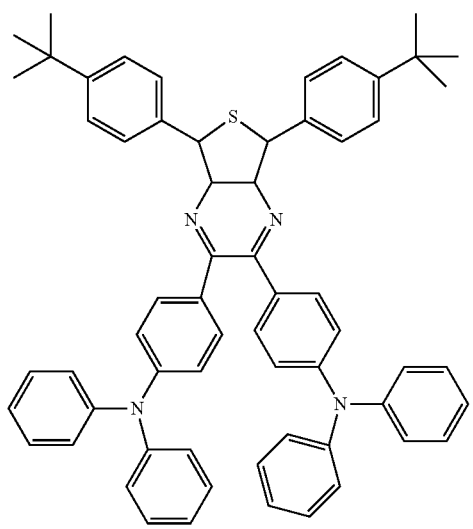
F64
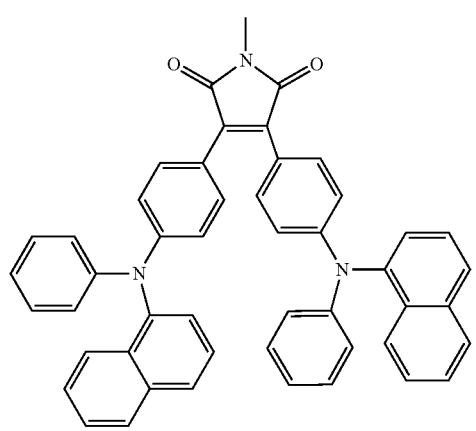

-continued
F65
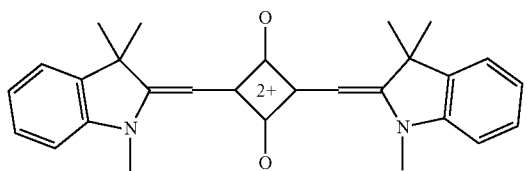
F66
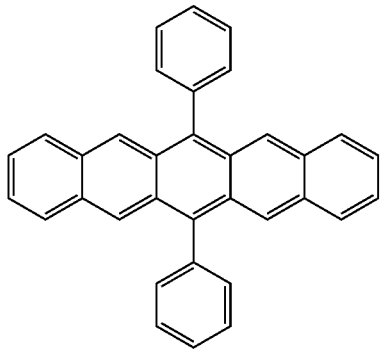
F67
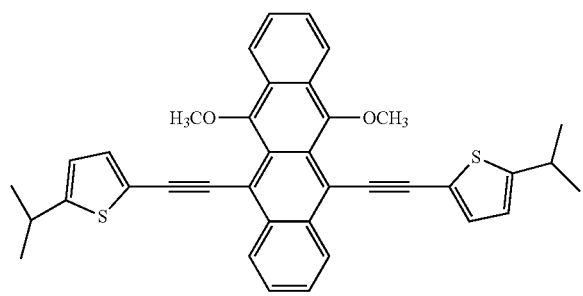
F68
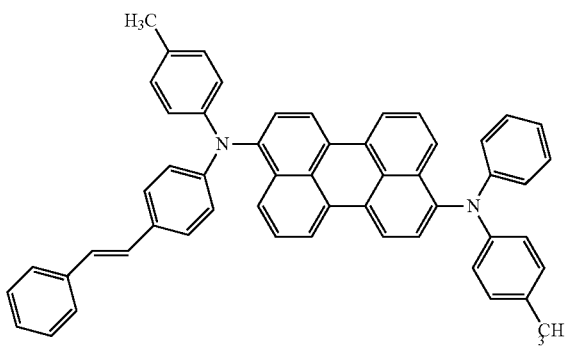
F69
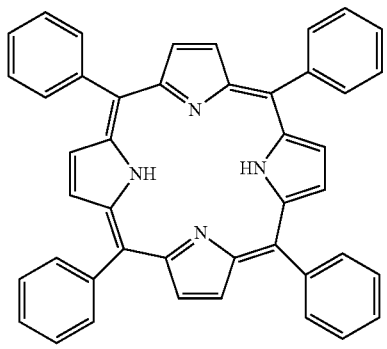

-continued
F70
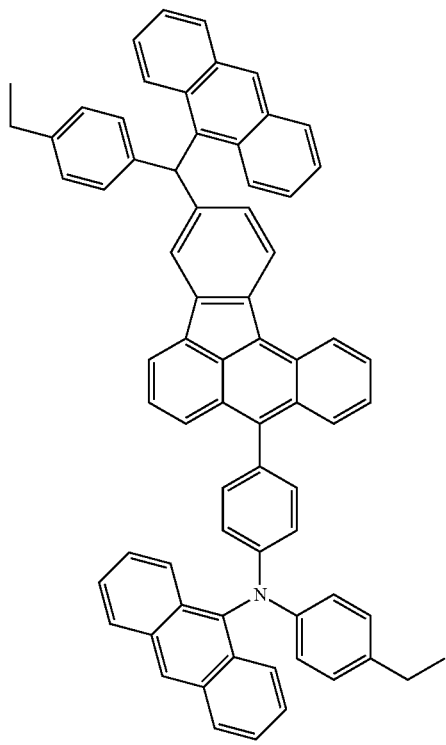
F71
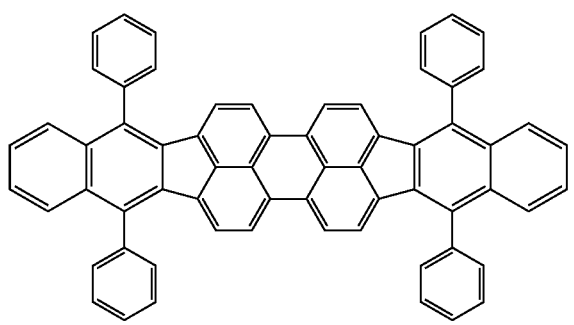
F72
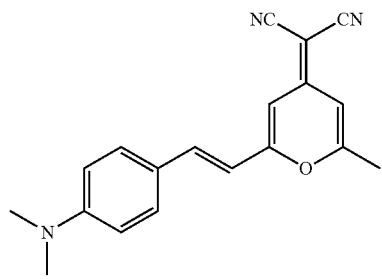

-continued
F73
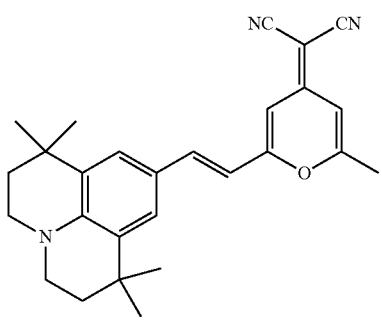
F74
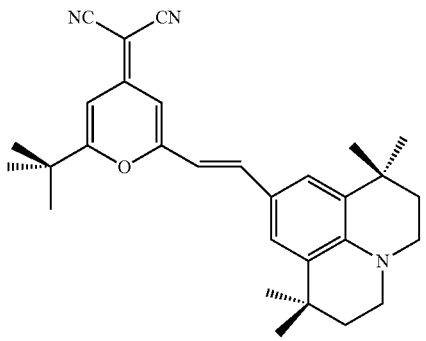
F75
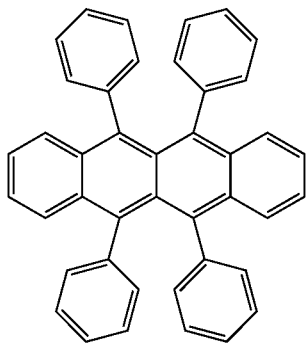
F76
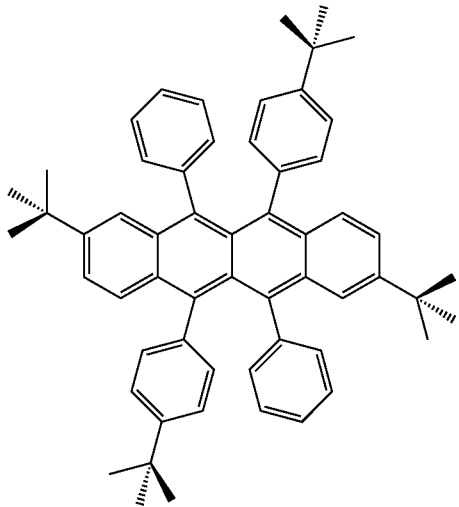

-continued
F77
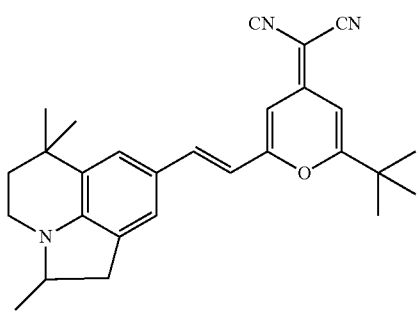
F78
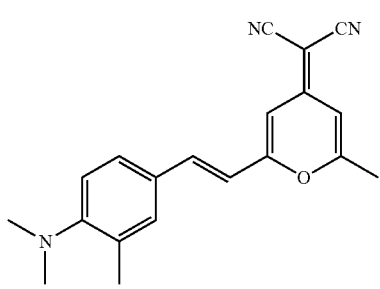
F79
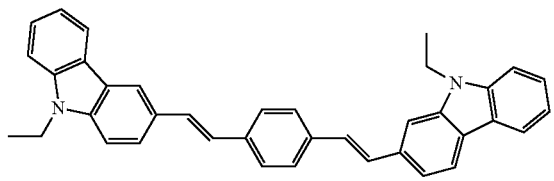
F80
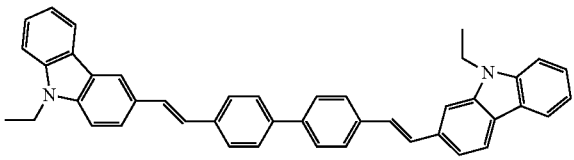
F81
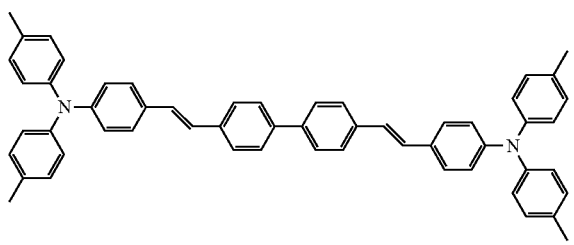
F82
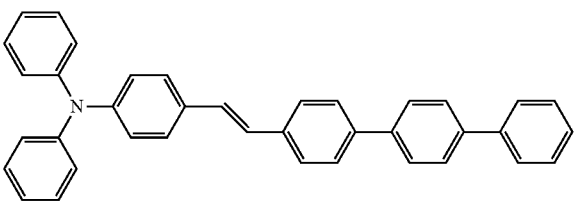

-continued
F83
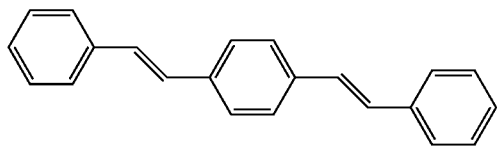
F84
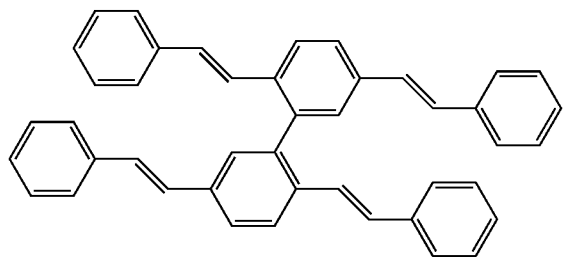
F85
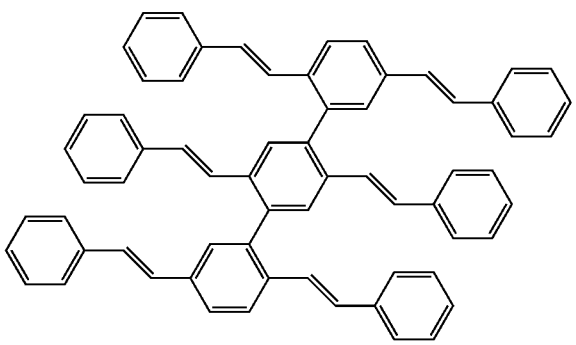
F86
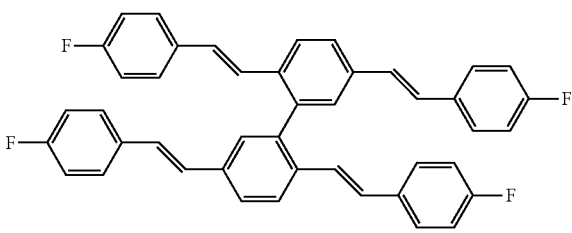
F87
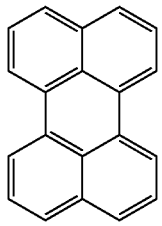
F88
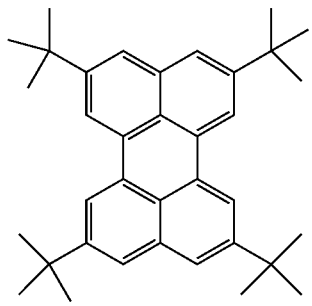

-continued
F89
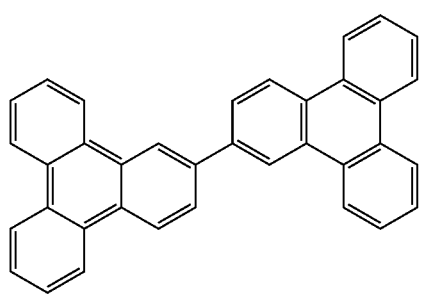
F90
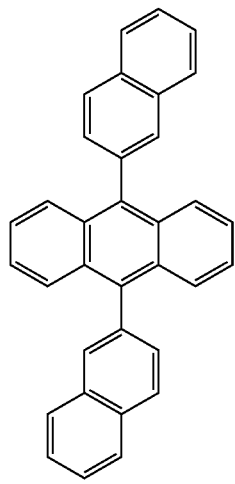
F91
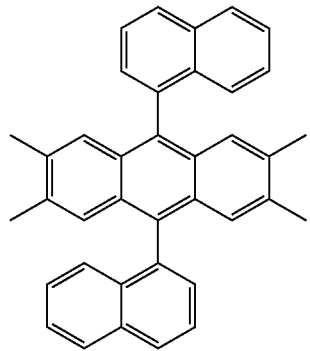
F92
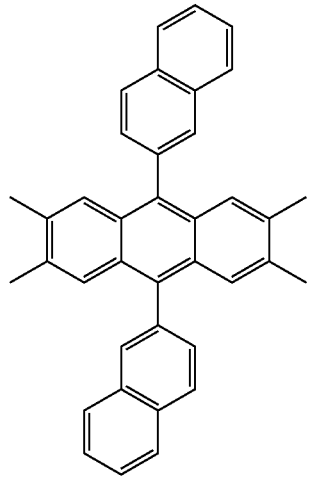

-continued
F93
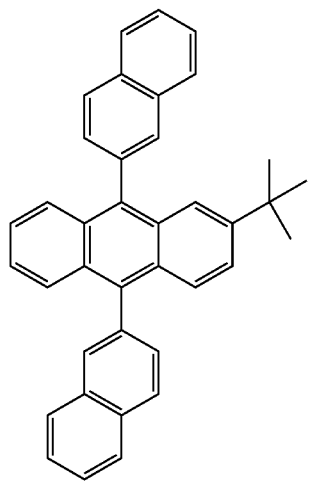
F94
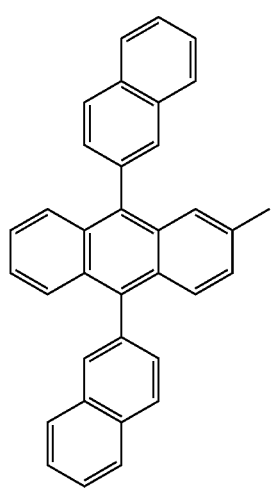
F95
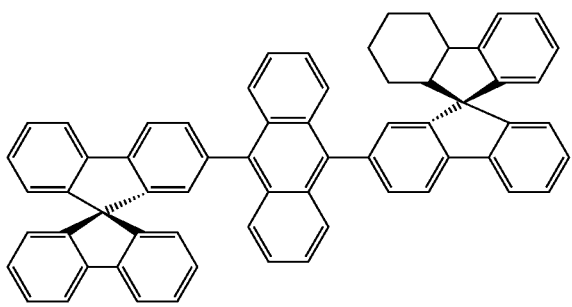
F96
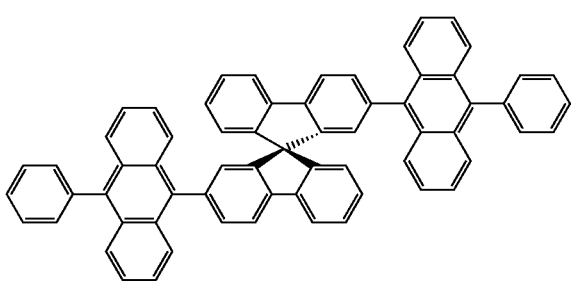

-continued
F97
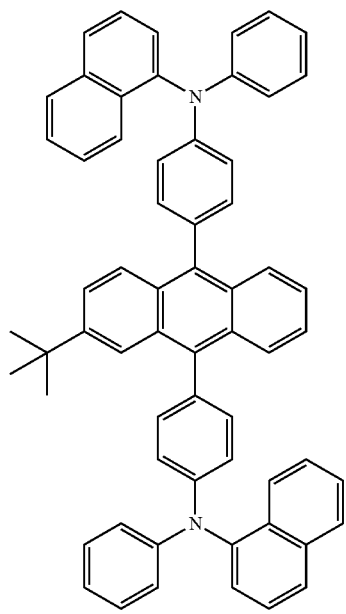
F98
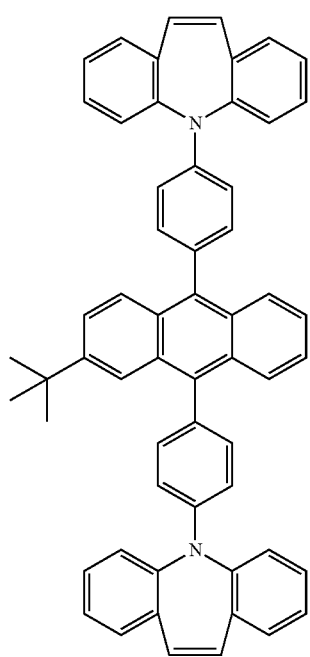

-continued
F99
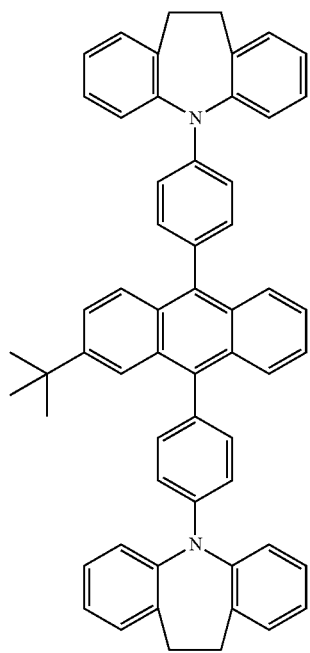
F100
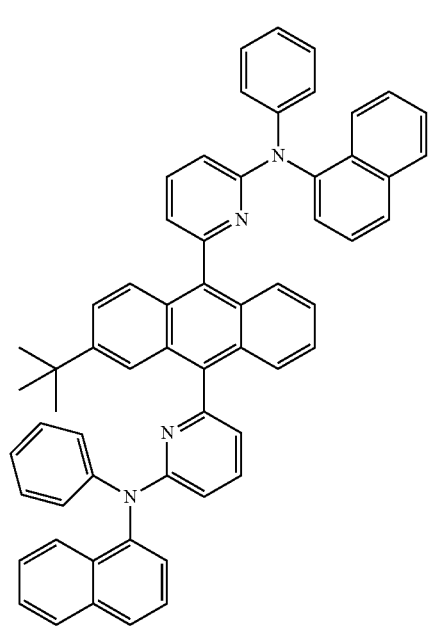

-continued
F101
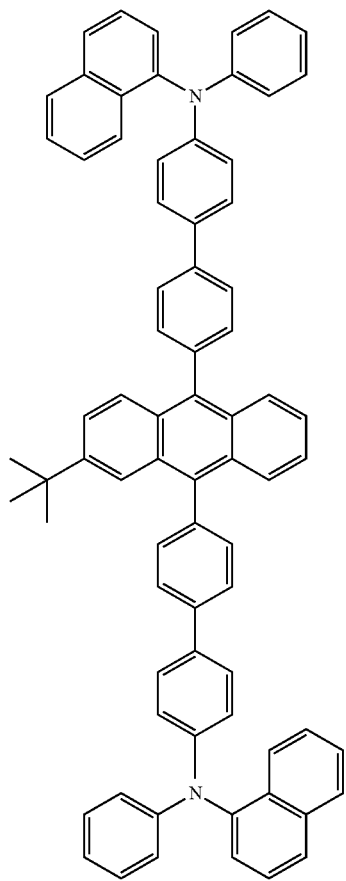
F102
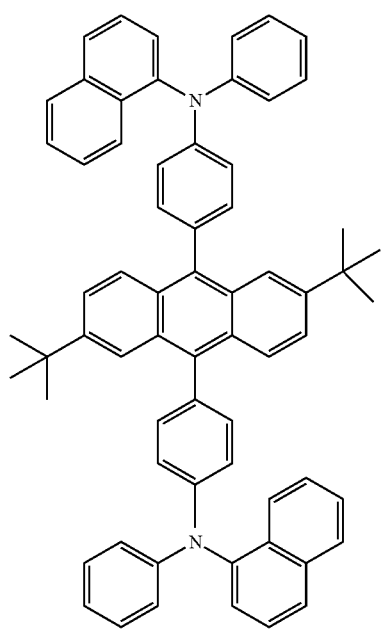

-continued
F103
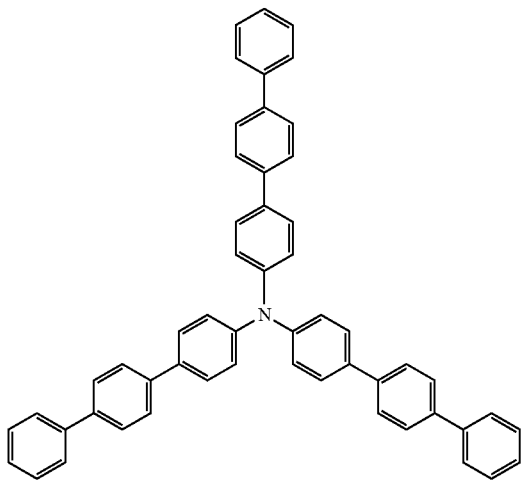
F104
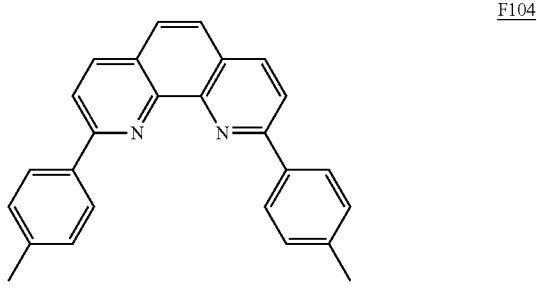
F105
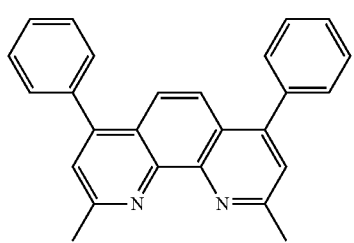
F106
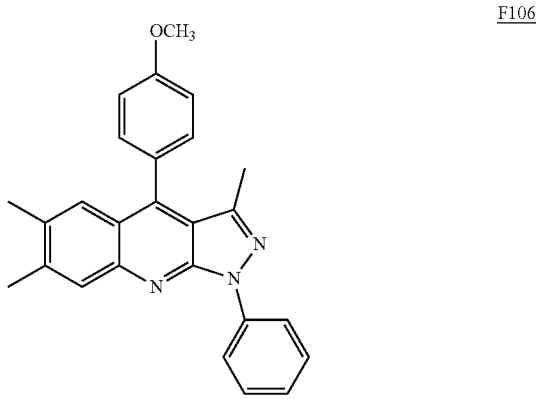
F107
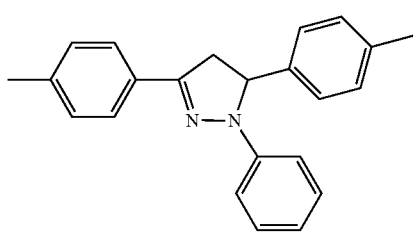

-continued
F108
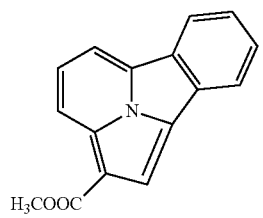
F109
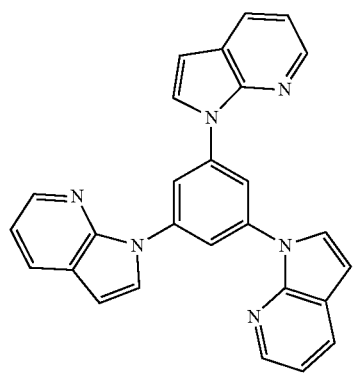
F110
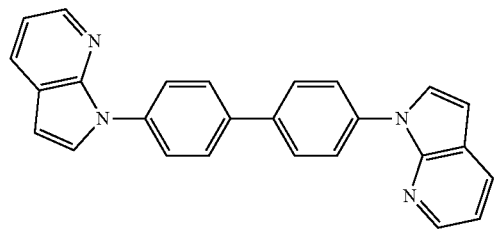
F111
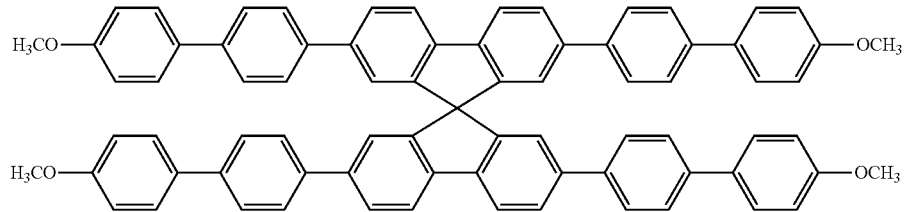
F112
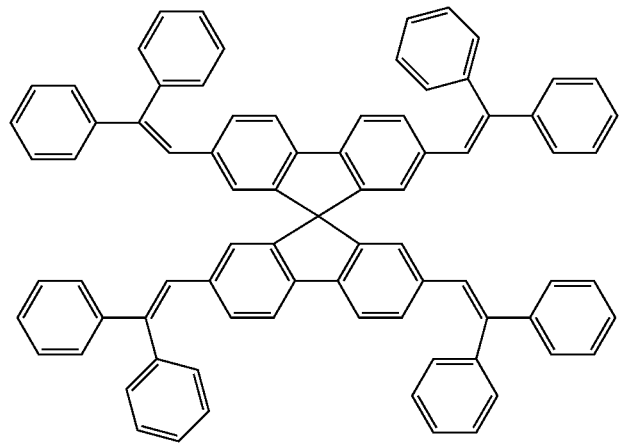

F113
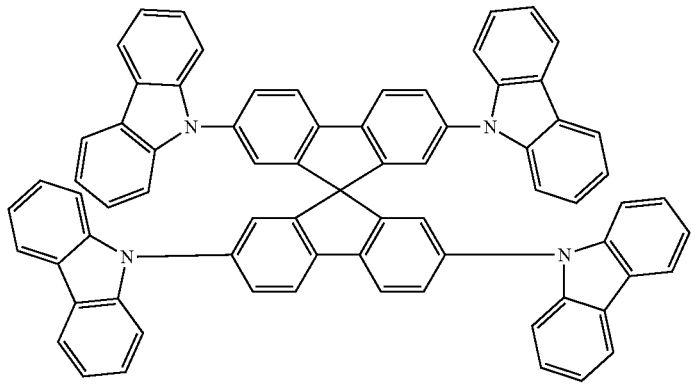
F114
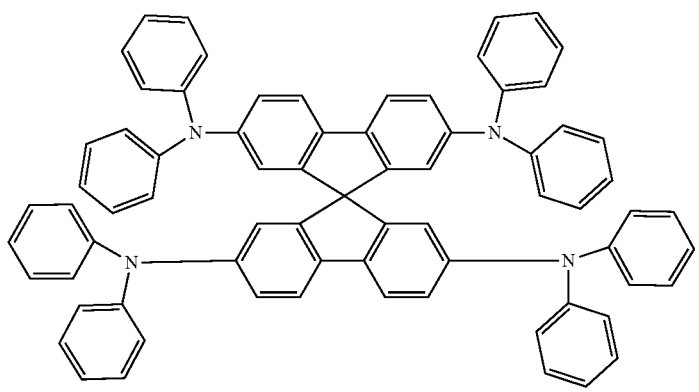
F115
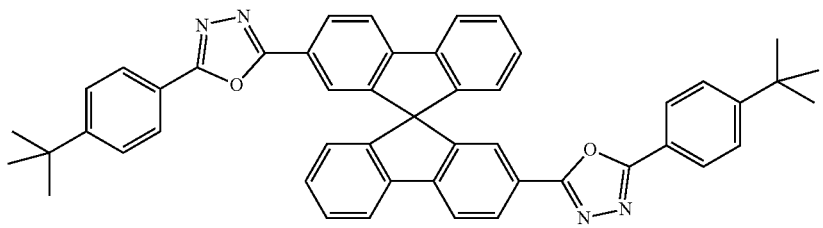
F116
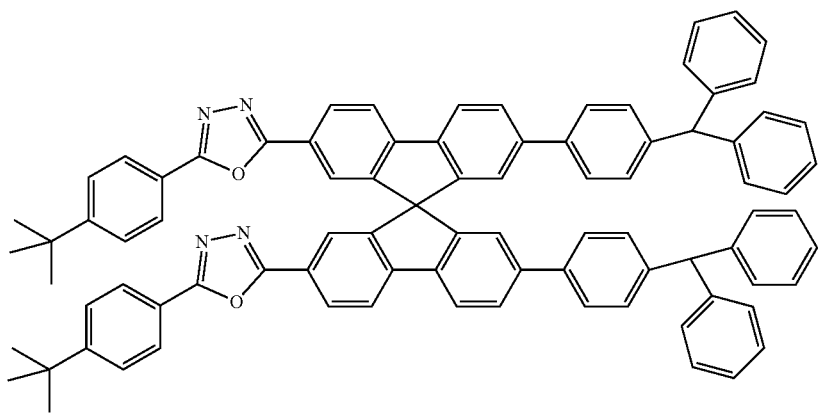
F117
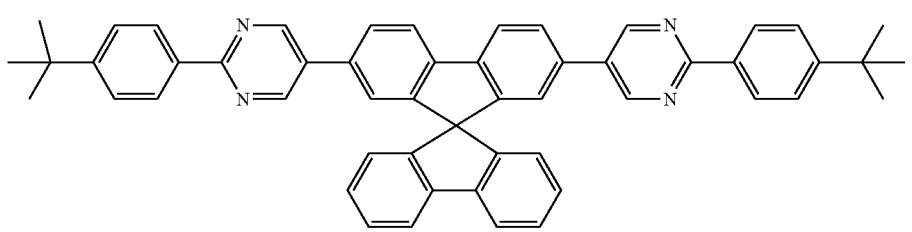

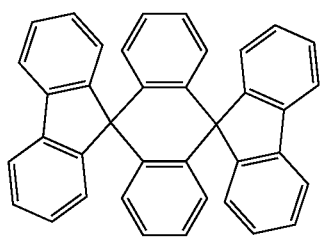
F118
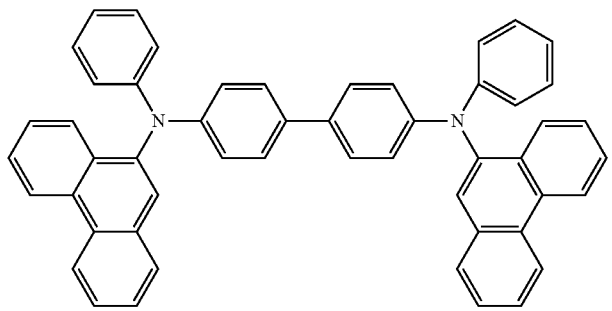
F119
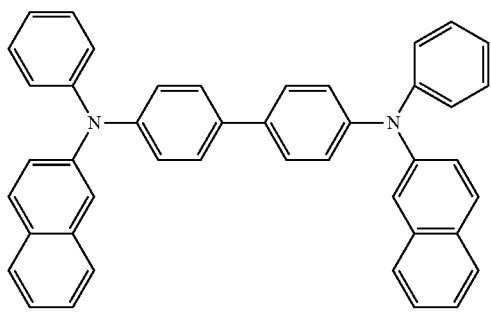
F120
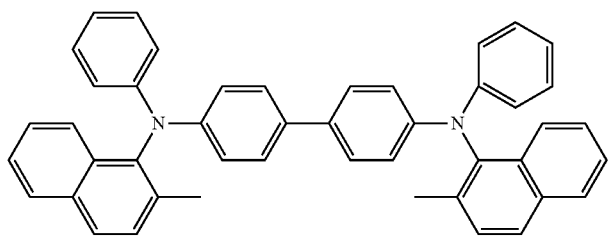
F121
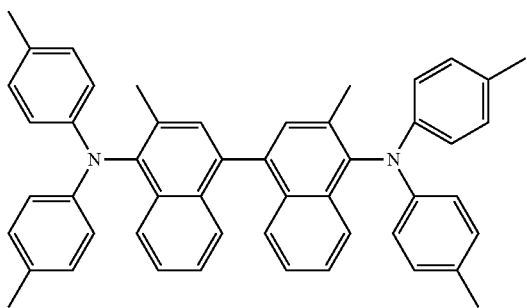
F122

-continued
F123
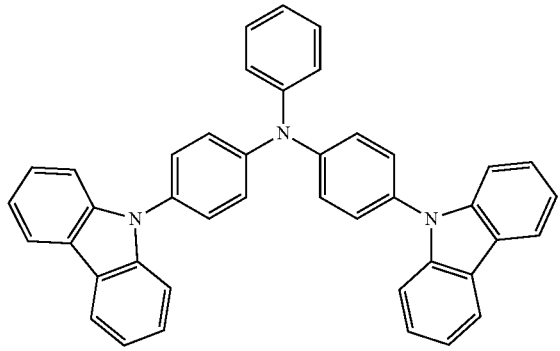
F124
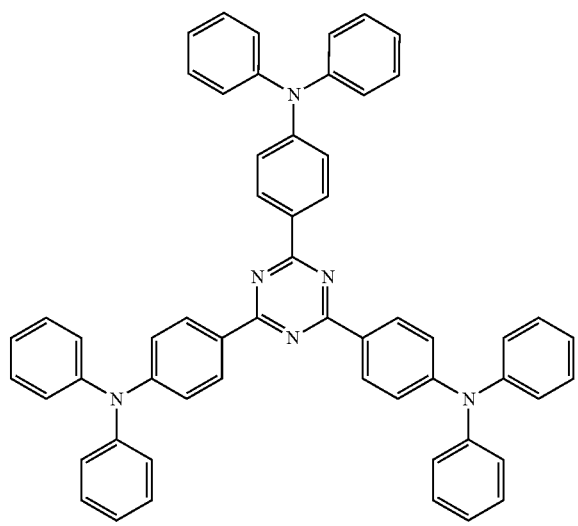
F125
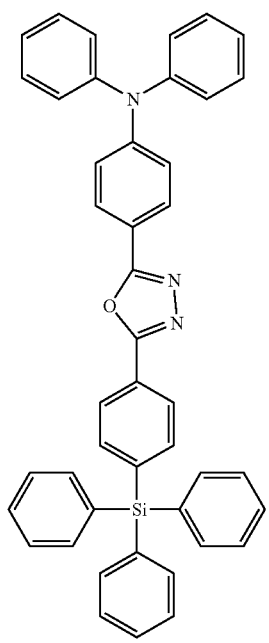

F126
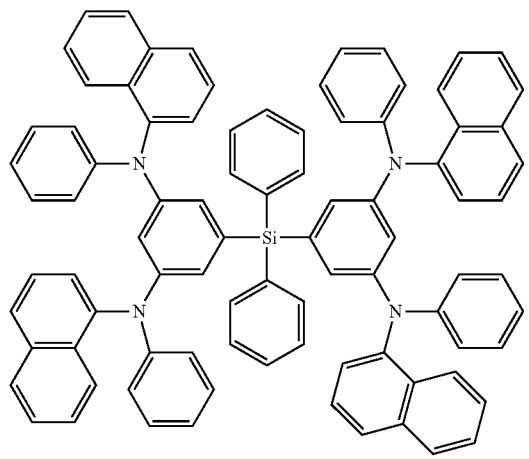
F127
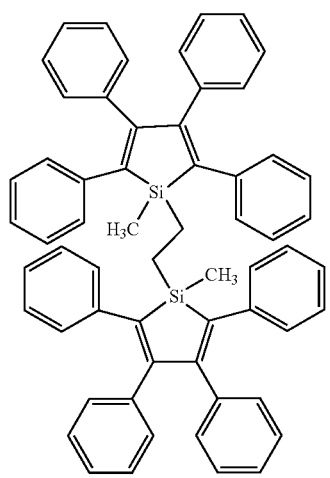
F128
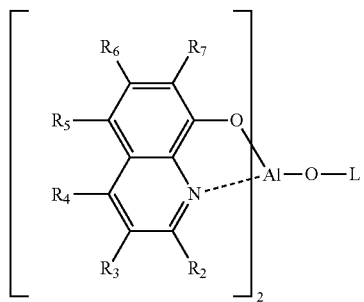
R2 - R7 = H or substituent, L = ligand -continued
F129
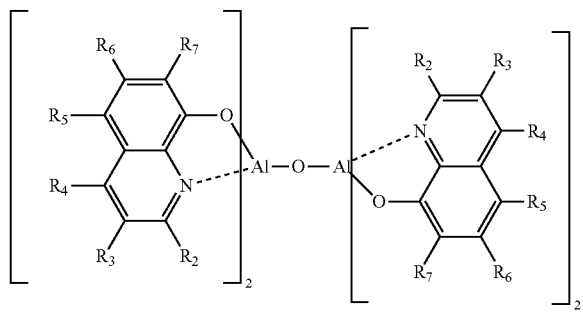
R2 - R7 = H or substituent, L = ligand
F130
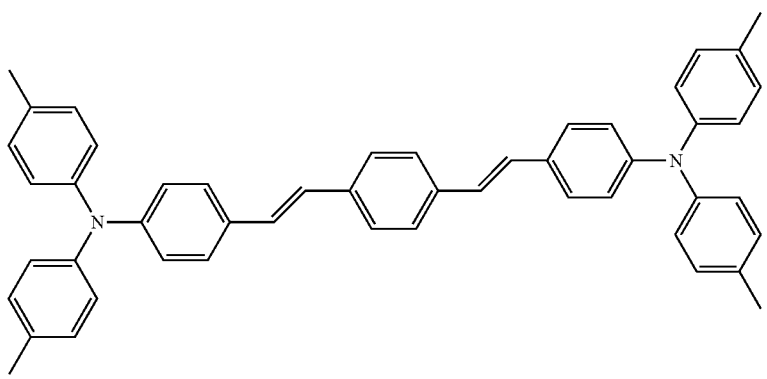
F131
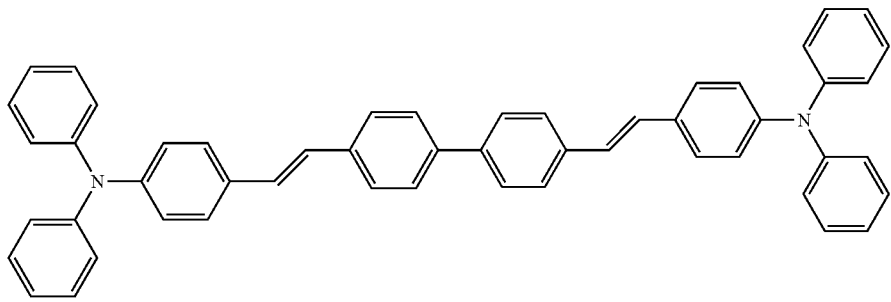
F132
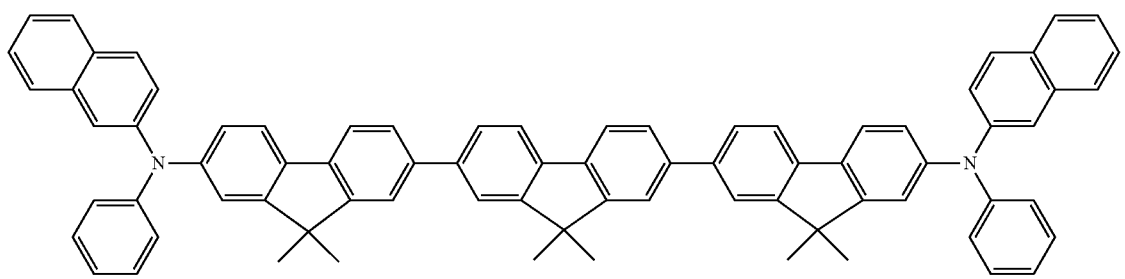
F133
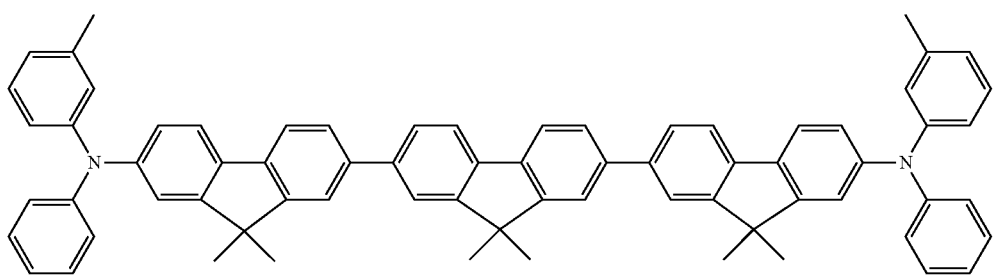

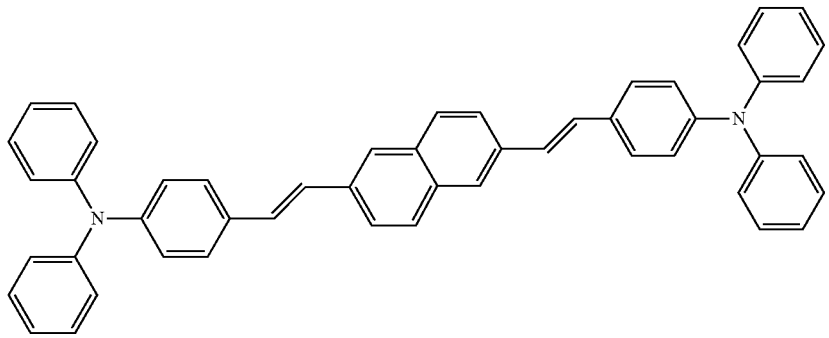
F134
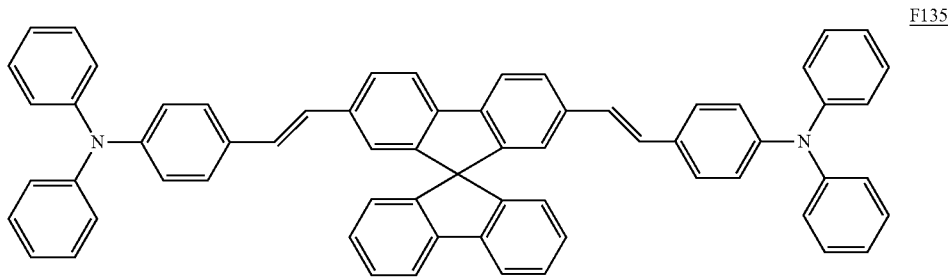
F135
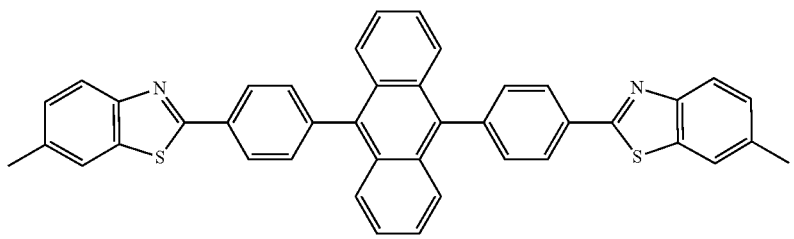
F136
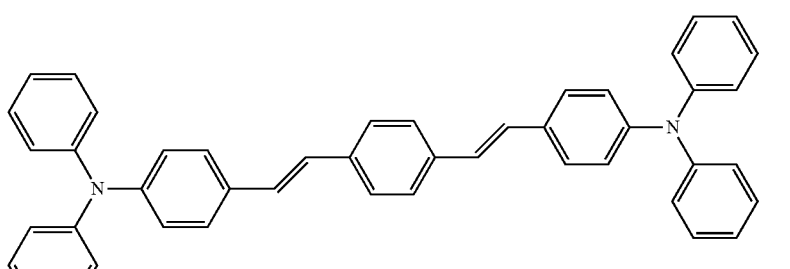
F137
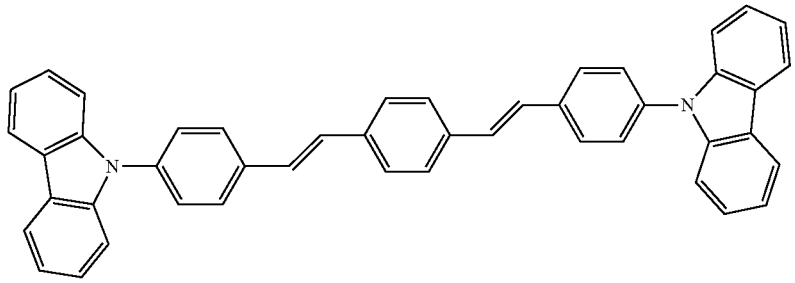
F138

-continued
F139
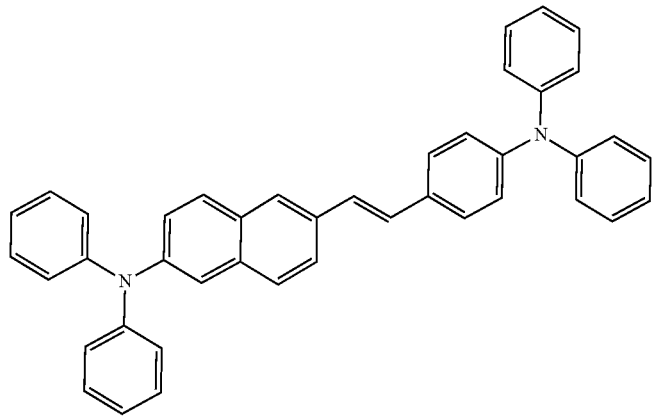
F140
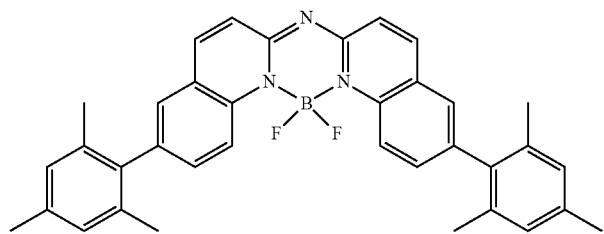
F141
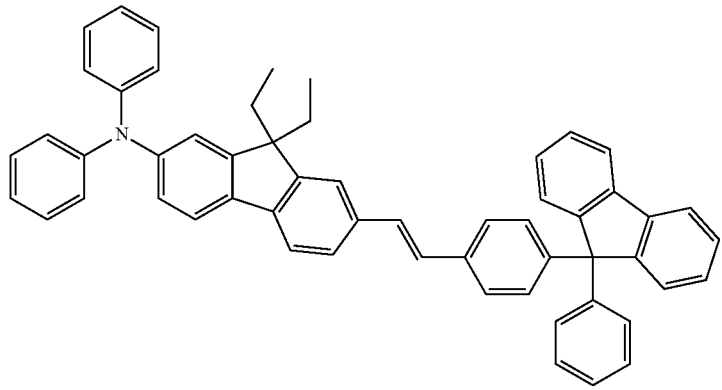
F142
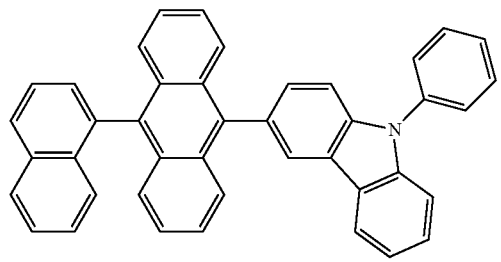
F143
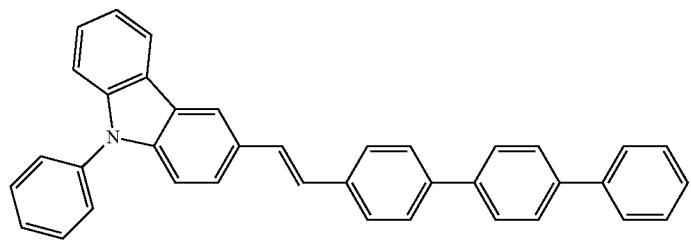

-continued
F144
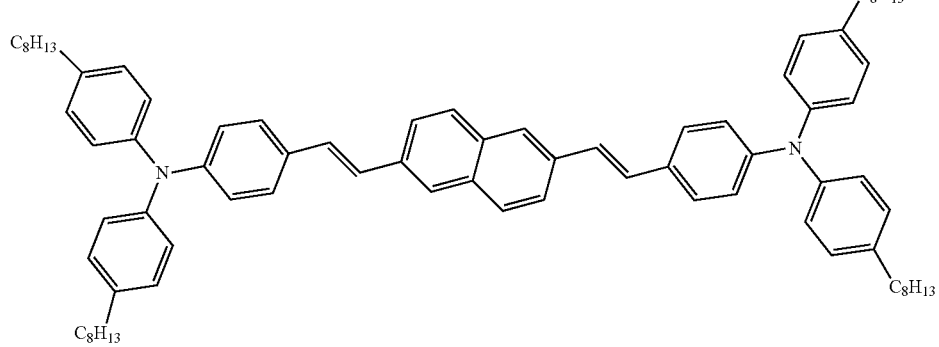
F145
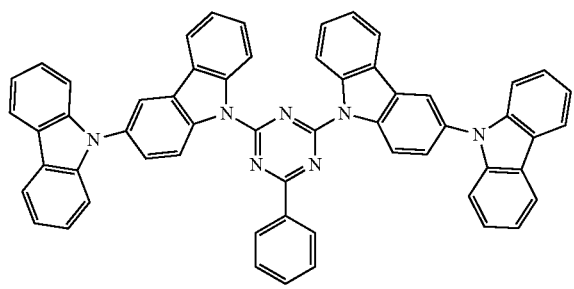
F146
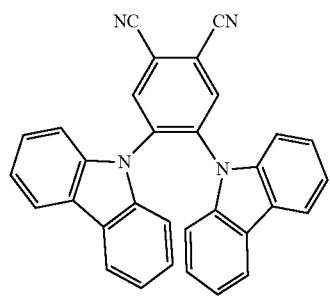
F147
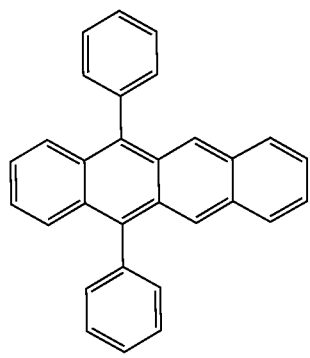

-continued
F148
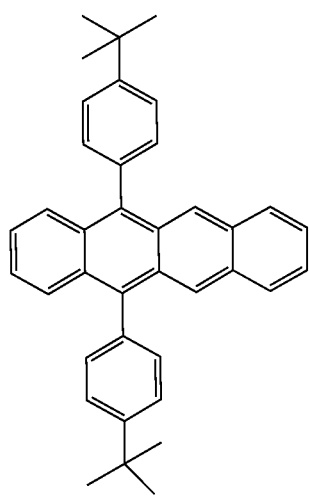
F149
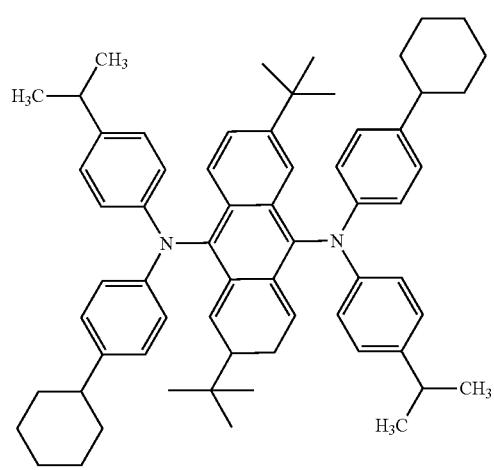
F150
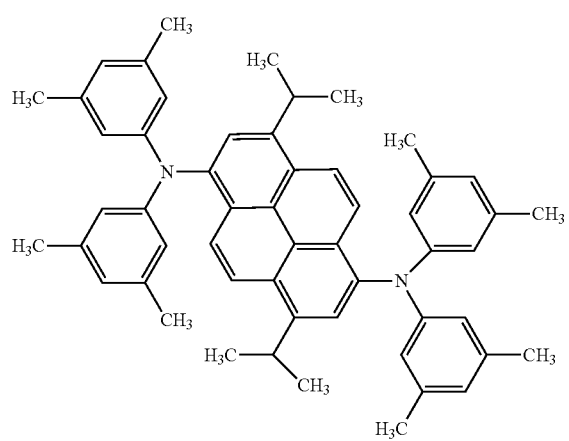

-continued
F151
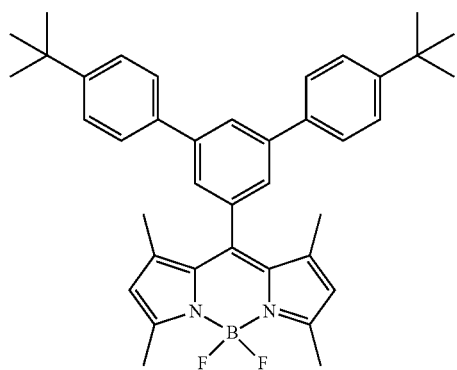
F152
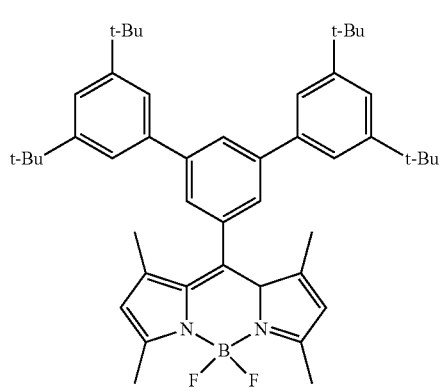
F153
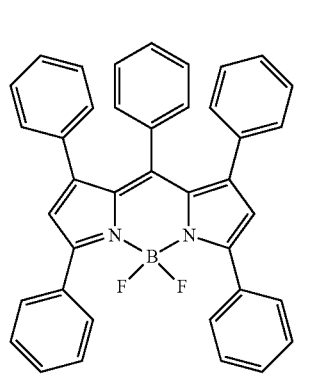
F154
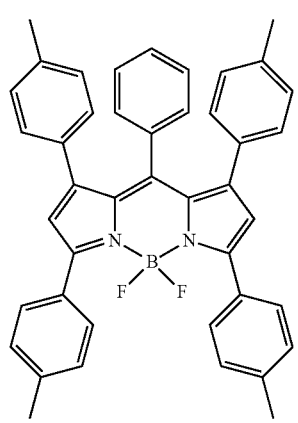

-continued
F155

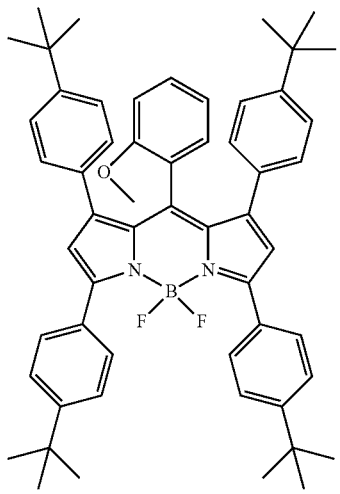

(Light Emitting Composition)

The composition of the present invention containing the first compound and the second compound is useful as a light emitting composition.

The light emitting composition may be a solution state or may be a solid state. The solvent used for making the solution state can be appropriately selected from solvents that can dissolve the composition. For example, organic solvents, such as toluene, can be mentioned. In the case of a solid state, a film (film-form, thin film-form) is preferred. In the case of a thin film state, for example, a film may be formed as a layer of a light emitting element having a laminate structure.

In an embodiment, a film containing the composition of the present invention can be formed through a wet process. In a wet process, a solution having the composition of the present invention dissolved therein is applied on a surface, and the solvent is removed and then a film is formed. As the wet process, a spin coating method, a slit coating method, an inkjet method (spray method), a gravure printing method, an offset printing method, and a flexographic printing method can be mentioned, but the process is not limited thereto. In the wet process, a suitable organic solvent that can dissolve the composition of the present invention is selected and used. In an embodiment, into a compound contained in the composition, a substituent (for example, alkyl group) that enhances the solubility in an organic solvent can be introduced.

In an embodiment, a film containing the composition of the present invention can be formed through a dry process. In an embodiment, as the dry process, a vacuum deposition method can be adopted, but the process is not limited thereto. When a vacuum deposition method is adopted, compounds constituting a film may be co-deposited from individual evaporation sources or may be co-deposited from a single evaporation source having the compounds mixed therein. When a single evaporation source is used, a mixed powder having powder compounds mixed may be used, a compressed molded body obtained by compressing the mixed powder may be used, or a mixture obtained by melting each compound with heat, followed by cooling may also be used. In an embodiment, by performing co-deposition under a condition in which the deposition rates (weight reduction rates) of the multiple compounds contained in a single evaporation source are the same or almost the same, a film of a composition ratio corresponding to the composition ratio of multiple compounds contained in the evaporation source can be formed. When multiple compounds are mixed at the same composition ratio as the composition ratio of the film to be formed to make an evaporation source, a film having a desired composition ratio can be conveniently formed. In an embodiment, the temperature at which the co-deposited compounds have the same weight reduction rate is specified, and the temperature can be adopted as the temperature in the co-deposition.

(Method for Providing Light Emitting Composition)

The present invention also relates to a method for providing a light emitting composition containing a first compound and a second compound.

The method for providing a light emitting composition of the present invention is a method for providing a light emitting composition containing a first compound and a second compound by designing the first compound to be combined with the second compound that has a $\Delta E_{ST}(2)$ less than 0.20 eV. The method is characterized by including designing the second compound so that $E_{S1}(1)$ is higher than $E_{S1}(2)$ and PBHT(1) is more than 0.730. In designing, the following step is preferably performed once or more times: the PBHT value and $E_{S1}$ of a specific molecular structure is determined, the PBHT value and $E_{S1}$ of a molecular structure obtained by partially modifying the specific molecular structure is determined, and while confirming that the $E_{S1}$ is equal to $E_{S1}(1)$, a structure having a larger PBHT value is selected. The step is preferably repeated multiple times until the PBHT value is no longer expected to be increased by modification of the molecular structure. The partial modification of the molecular structure can be achieved, for example, by changing a hydrogen atom in the molecular structure to a substituent or by changing a substituent in the molecular structure to another substituent. As the substituent as used herein, the examples mentioned as the substituent represented by R of the first compound can be exemplified. Also, a ring backbone forming atom can be changed, for example, from a carbon atom to a nitrogen atom or from a nitrogen atom to a carbon atom. Furthermore, a ring backbone forming atom can be changed, for example, from an oxygen atom to a sulfur atom or from a sulfur atom to an oxygen atom.

Alternatively, a substitution position of a substituent can be changed or a bonding position can be changed. While performing such modification and while confirming that $E_{S1}$ is equal to $E_{S1}(1)$, a structure having a larger PBHT value can be selected.

For example, the PBHT value and $E_{S1}$ of a compound having a specific structure represented by the general formula (1) are determined, the PBHT value and $E_{S1}$ of a compound obtained by partially modifying the structure are determined, and the values of $E_{s1}$ and PBHT are compared, whereby the method of the present invention can be conducted. In the modification, X of the general formula (1) can be changed, at least one of $Y^1$ to $Y^8$ and $Y^{11}$ to $Y^{18}$ can be changed from C—R to N or from N to C—R, R of at least one C—R of $Y^1$ to $Y^8$ and $Y^{11}$ to $Y^{18}$ can be changed, n can be changed, a substituent of L can be changed, the backbone of L can be changed, $Y^1$ to $Y^4$ bonded to L can be changed, or $Y^{11}$ to $Y^4$ bonded to L can be changed. Such a modification is appropriately performed, and while confirming that $E_{S1}$ is equal to $E_{S1}(1)$, a structure having a larger PBHT value can be selected.

In the method of the present invention, the PBHT value and $E_{S1}$ can be determined by calculation. A program that executes the method of the present invention may be created and the program may be used to execute the method. The program can be operated by using a computer, such as a personal computer.

(Organic Light Emitting Element)

The composition of the present invention is useful as a light emitting composition. Thus, by using the composition of the present invention, an excellent organic light emitting element, such as an organic photoluminescence element (organic PL element) or an organic electroluminescence element (organic EL element), can be provided. An organic photoluminescence element has a structure in which at least a light emitting layer is formed on a substrate. An organic electroluminescence element has a structure including at least an anode, a cathode, and an organic layer formed between the anode and the cathode. The organic layer includes at least a light emitting layer, and may be composed only of the light emitting layer or may have one or more organic layers other than the light emitting layer. As the other organic layer, a hole transporting layer, a hole injecting layer, an electron barrier layer, a hole barrier layer, an electron injecting layer, an electron transporting layer, and an exciton barrier layer can be mentioned. The hole transporting layer may be a hole injecting transporting layer having a hole injecting function, the electron transporting layer may be an electron injecting transporting layer having an electron injecting function. A specific example of a structure of an organic electroluminescence element is illustrated in FIG. 1. In FIG. 1, 1 represents a substrate, 2 represents an anode, 3 represents a hole injecting layer, 4 represents a hole transporting layer, 5 represents a light emitting layer, 6 represents an electron transporting layer, and 7 represents a cathode. The composition of the present invention can be used in a light emitting layer.

Members and layers in the organic electroluminescence element will be described below. Note that the description of the substrate and light emitting layer also apply to the substrate and light emitting layer of an organic photoluminescence element.

Substrate:

In some embodiments, the organic electroluminescence element of the present invention is held by a substrate. The substrate is not particularly limited, and any material generally used in an organic electroluminescence element and, for example, formed of glass, a transparent plastic, quartz, and silicon may be used.

Anode

In some embodiments, the anode of the organic electroluminescent device is made of a metal, an alloy, an electroconductive compound, or a combination thereof. In some embodiments, the metal, alloy, or electroconductive compound has a large work function (4 eV or more). In some embodiments, the metal is Au. In some embodiments, the electroconductive transparent material is selected from CuI, indium tin oxide (ITO), $SnO_2$, and ZnO. In some embodiments, an amorphous material capable of forming a transparent electroconductive film, such as IDIXO ($In_2O_3$—ZnO), is be used. In some embodiments, the anode is a thin film. In some embodiments the thin film is made by vapor deposition or sputtering. In some embodiments, the film is patterned by a photolithography method. In some embodiments, where the pattern may not require high accuracy (for example, approximately 100 μm or more), the pattern may be formed with a mask having a desired shape on vapor deposition or sputtering of the electrode material.

In some embodiments, when a material can be applied as a coating, such as an organic electroconductive compound, a wet film forming method, such as a printing method and a coating method is used. In some embodiments, when the emitted light goes through the anode, the anode has a transmittance of more than 10%, and the anode has a sheet resistance of several hundred Ohm per square or less. In some embodiments, the thickness of the anode is from 10 to 1,000 nm. In some embodiments, the thickness of the anode is from 10 to 200 nm. In some embodiments, the thickness of the anode varies depending on the material used.

Cathode

In some embodiments, the cathode is made of an electrode material a metal having a small work function (4 eV or less) (referred to as an electron injection metal), an alloy, an electroconductive compound, or a combination thereof. In some embodiments, the electrode material is selected from sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal In some embodiments, a mixture of an electron injection metal and a second metal that is a stable metal having a larger work function than the electron injection metal is used. In some embodiments, the mixture is selected from a magnesium-silver mixture, a magnesium-aluminum mixture, a magnesium-indium mixture, an aluminum-aluminum oxide ($Al_2O_3$) mixture, a lithium-aluminum mixture, and aluminum. In some embodiments, the mixture increases the electron injection property and the durability against oxidation. In some embodiments, the cathode is produced by forming the electrode material into a thin film by vapor deposition or sputtering. In some embodiments, the cathode has a sheet resistance of several hundred Ohm per square or less. In some embodiments, the thickness of the cathode ranges from 10 nm to 5 μm. In some embodiments, the thickness of the cathode ranges from 50 to 200 nm. In some embodiments, for transmitting the emitted light, any one of the anode and the cathode of the organic electroluminescent device is transparent or translucent. In some embodiments, the transparent or translucent electroluminescent devices enhances the light emission luminance.

In some embodiments, the cathode is formed with an electroconductive transparent material, as described for the anode, to form a transparent or translucent cathode. In some embodiments, a device comprises an anode and a cathode, both being transparent or translucent.

Light-Emitting Layer

In some embodiments, the light-emitting layer is a layer, in which holes and electrons, injected respectively from the anode and the cathode, are recombined to form excitons. In some embodiments the layer emits light.

The composition of the present invention is used in a light emitting layer. In some embodiments, the emitted light includes both fluorescence and delayed fluorescence. In some embodiments, the emitted light includes phosphorescence. In some embodiments, the emitted light includes emitted light from the second compound. In some embodiments, the emitted light includes emitted light from the second compound and emitted light from the first compound. In an embodiment in which the third compound is used, the emitted light includes emitted light from the third compound. In another embodiment in which the third compound is used, the emitted light includes emitted light from the third compound and emitted light from the second compound. In another embodiment in which the third compound is used, the emitted light includes emitted light from the third compound, emitted light from the second compound, and emitted light from the first compound. In some embodiments in which the third compound is used, the second compound is an auxiliary dopant.

Injection Layer

An injection layer is a layer between the electrode and the organic layer. In some embodiments, the injection layer decreases the driving voltage and enhances the light emission luminance. In some embodiments the injection layer includes a hole injection layer and an electron injection layer. The injection layer can be positioned between the anode and the light-emitting layer or the hole transporting layer, and between the cathode and the light-emitting layer or the electron transporting layer. In some embodiments, an injection layer is present. In some embodiments, no injection layer is present.

Preferred examples of a compound that can be used as a hole injecting material are shown below.

MoO₃,

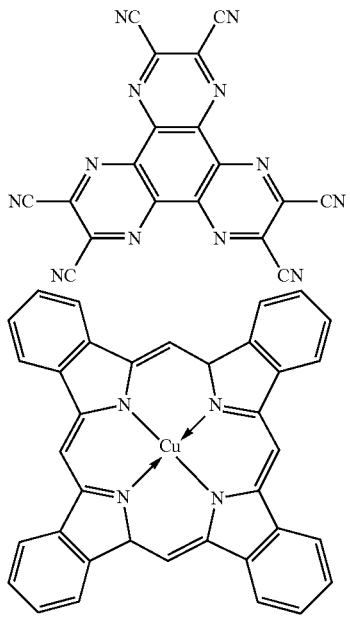

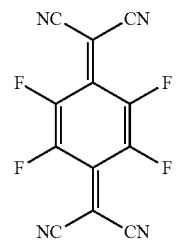

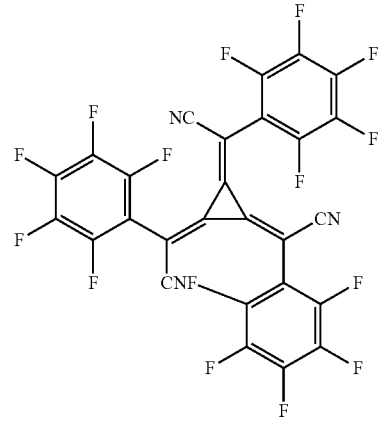

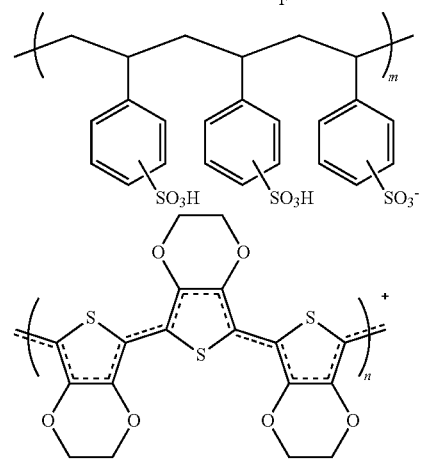

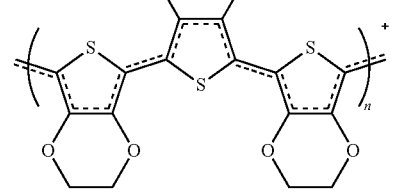

Next, preferred examples of a compound that can be used as an electron injecting material are shown below.

LiF, CsF, 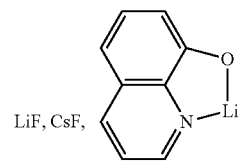

Barrier Layer

A barrier layer is a layer capable of inhibiting charges (electrons or holes) and/or excitons present in the light-emitting layer from being diffused outside the light-emitting layer. In some embodiments, the electron barrier layer is between the light-emitting layer and the hole transporting layer, and inhibits electrons from passing through the light-emitting layer toward the hole transporting layer. In some embodiments, the hole barrier layer is between the light-emitting layer and the electron transporting layer, and inhibits holes from passing through the light-emitting layer toward the electron transporting layer. In some embodiments, the barrier layer inhibits excitons from being diffused outside the light-emitting layer. In some embodiments, the electron barrier layer and the hole barrier layer are exciton barrier layers. As used herein, the term "electron barrier layer" or "exciton barrier layer" includes a layer that has the functions of both electron barrier layer and of an exciton barrier layer.

Hole Barrier Layer

A hole barrier layer acts as an electron transporting layer. In some embodiments, the hole barrier layer inhibits holes from reaching the electron transporting layer while transporting electrons. In some embodiments, the hole barrier layer enhances the recombination probability of electrons and holes in the light-emitting layer. The material for the hole barrier layer may be the same materials as the ones described for the electron transporting layer.

Next, preferred examples of a compound that can be used as a hole barrier layer are shown below.

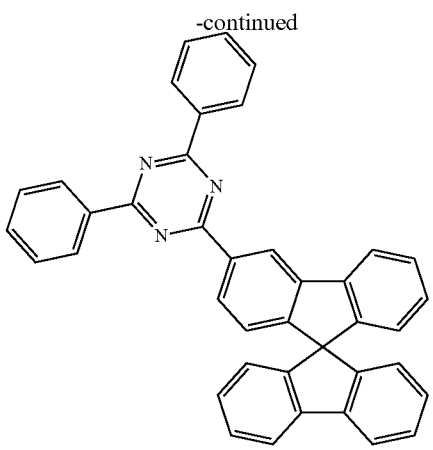

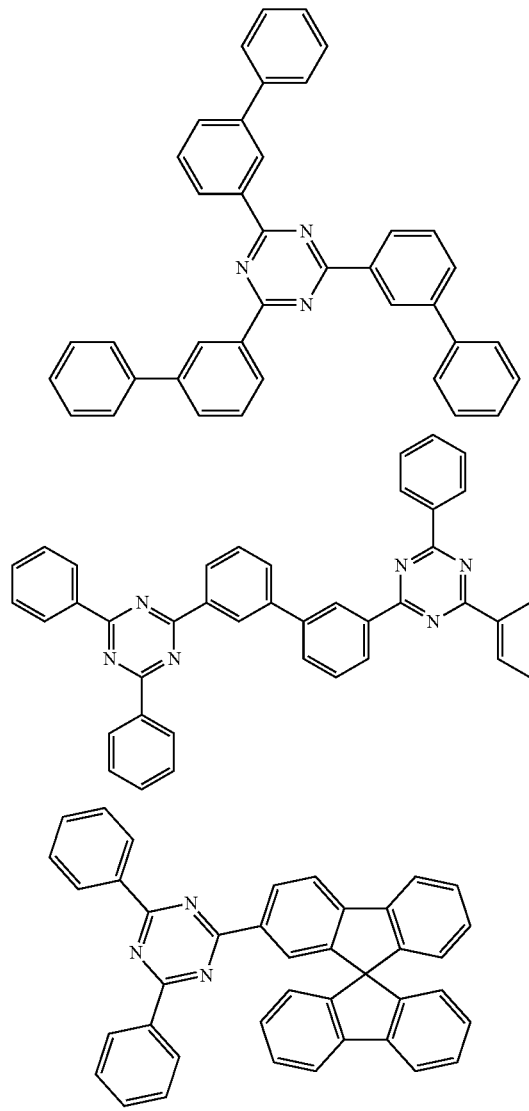

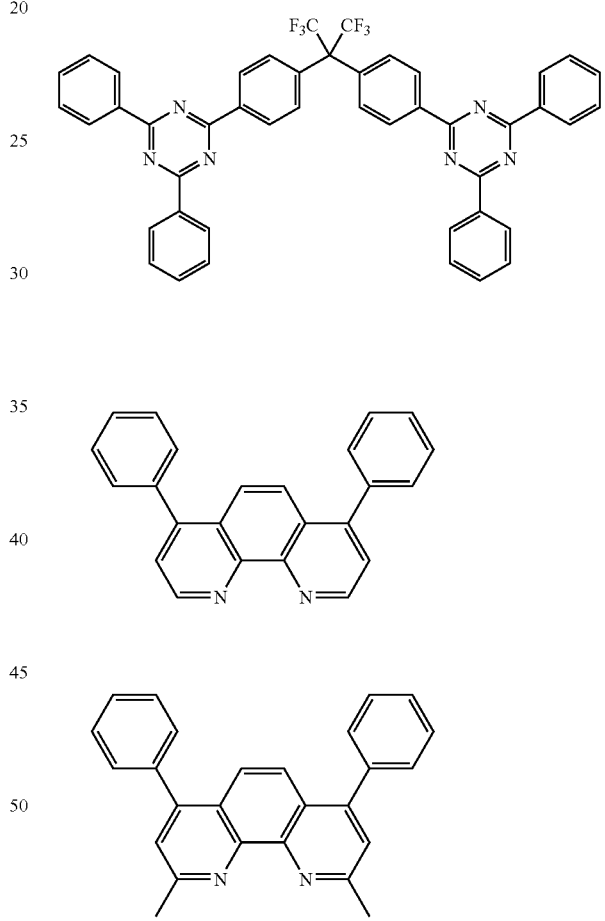

Electron Barrier Layer

As electron barrier layer transports holes. In some embodiments, the electron barrier layer inhibits electrons from reaching the hole transporting layer while transporting holes. In some embodiments, the electron barrier layer enhances the recombination probability of electrons and holes in the light-emitting layer. The material for the electron barrier layer may be the same materials as the ones described for the hole transporting layer.

Specific preferred examples of a compound that can be used as an electron barrier material are shown below.

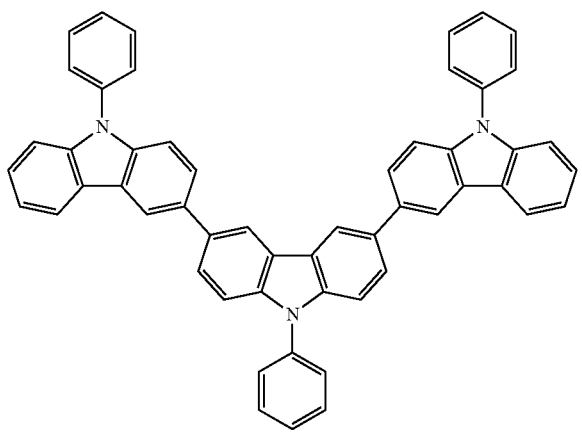

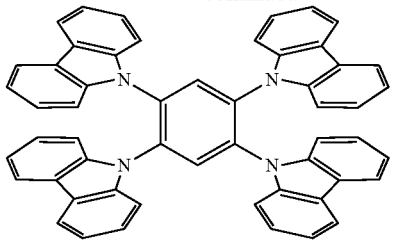

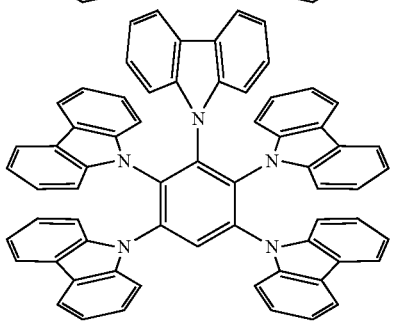

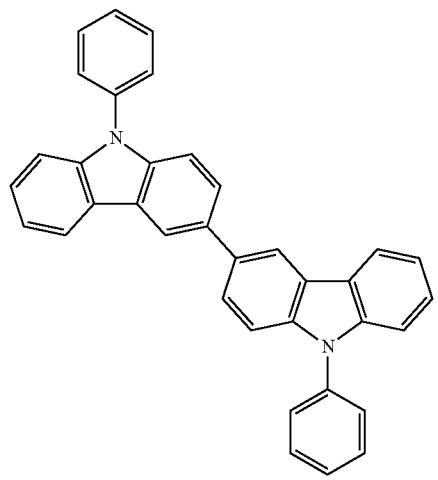

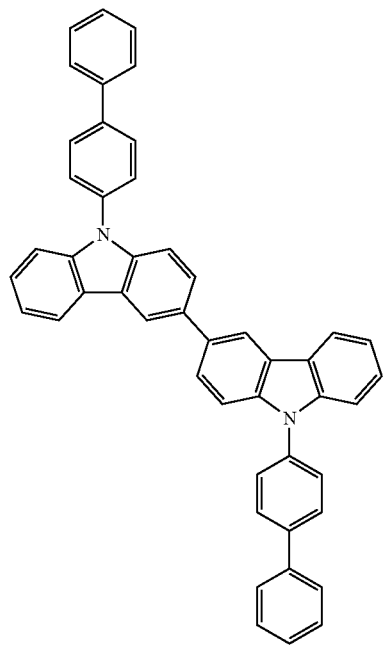

Exciton Barrier Layer

An exciton barrier layer inhibits excitons generated through recombination of holes and electrons in the light-emitting layer from being diffused to the charge transporting layer. In some embodiments, the exciton barrier layer enables effective confinement of excitons in the light-emitting layer. In some embodiments, the light emission efficiency of the device is enhanced. In some embodiments, the exciton barrier layer is adjacent to the light-emitting layer on any of the side of the anode and the side of the cathode, and on both the sides. In some embodiments, where the exciton barrier layer is on the side of the anode, the layer can be between the hole transporting layer and the light-emitting layer and adjacent to the light-emitting layer. In some embodiments, where the exciton barrier layer is on the side of the cathode, the layer can be between the light-emitting layer and the cathode and adjacent to the light-emitting layer. In some embodiments, a hole injection layer, an electron barrier layer, or a similar layer is between the anode and the exciton barrier layer that is adjacent to the light-emitting layer on the side of the anode. In some embodiments, a hole injection layer, an electron barrier layer, a hole barrier layer, or a similar layer is between the cathode and the exciton barrier layer that is adjacent to the light-emitting layer on the side of the cathode. In some embodiments, the exciton barrier layer comprises excited singlet energy and excited triplet energy, at least one of which is higher than the excited singlet energy and the excited triplet energy of the light-emitting material, respectively.

Hole Transporting Layer

The hole transporting layer comprises a hole transporting material. In some embodiments, the hole transporting layer is a single layer. In some embodiments, the hole transporting layer comprises a plurality layers.

In some embodiments, the hole transporting material has one of injection or transporting property of holes and barrier property of electrons. In some embodiments, the hole transporting material is an organic material. In some embodiments, the hole transporting material is an inorganic material. Examples of known hole transporting materials that may be used herein include but are not limited to a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer, or a combination thereof. In some embodiments, the hole transporting material is selected from a porphyrin compound, an aromatic tertiary amine compound, and a styrylamine compound. In some embodiments, the hole transporting material is an aromatic tertiary amine compound.

Specific preferred examples of a compound that can be used as a hole transporting material are shown below.

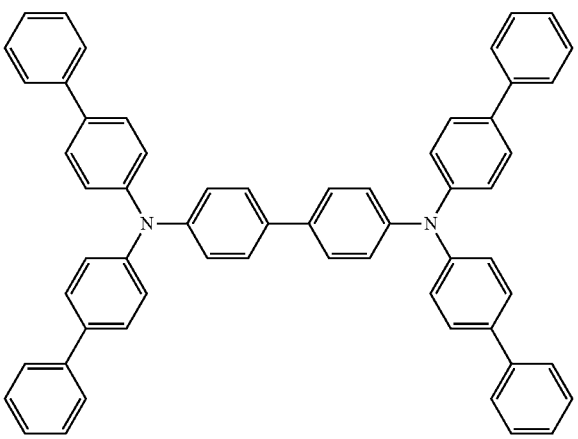

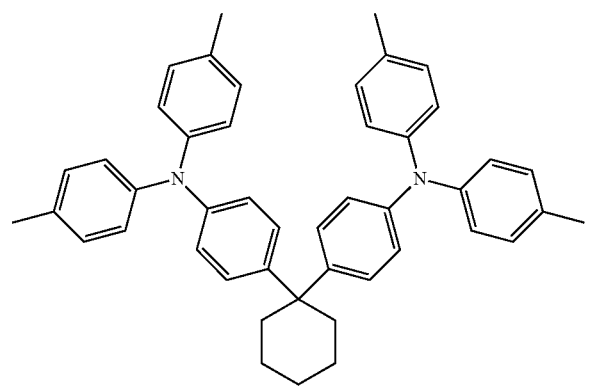

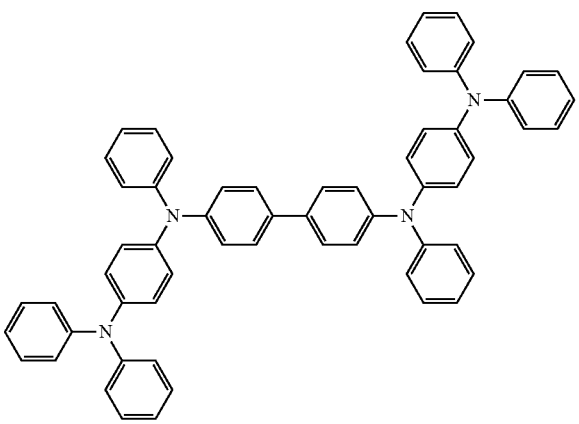

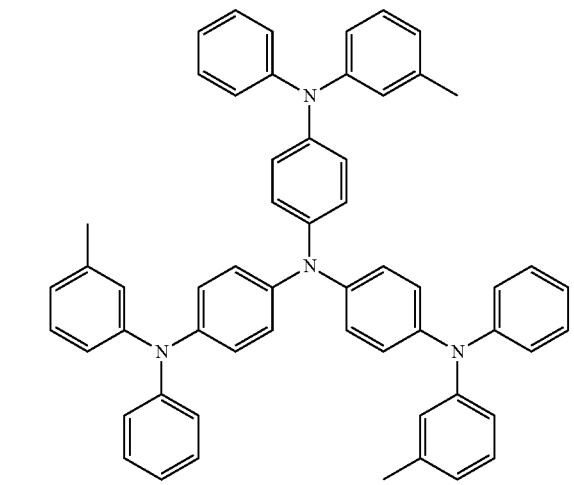

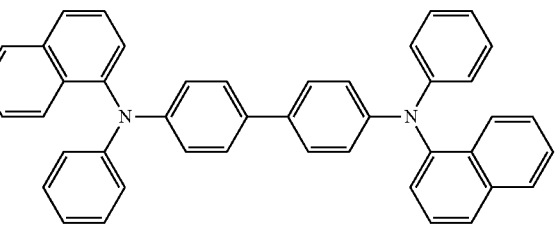

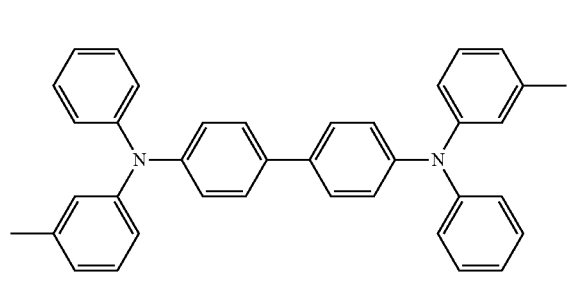

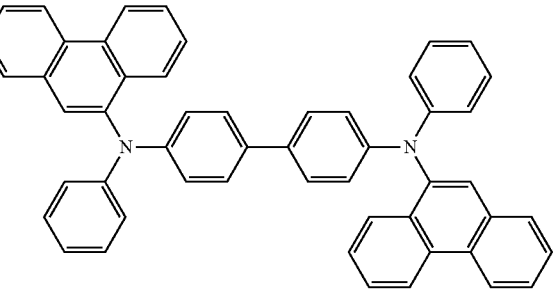

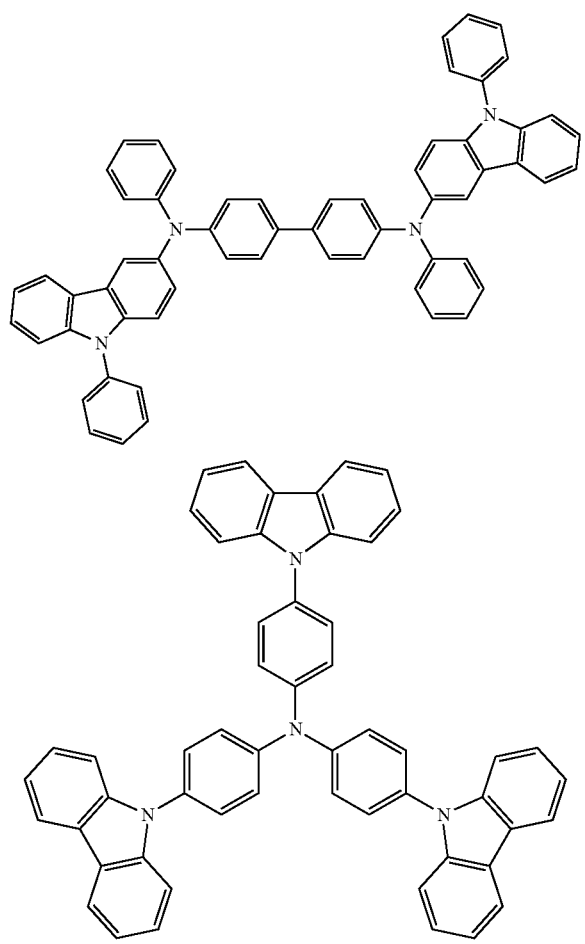

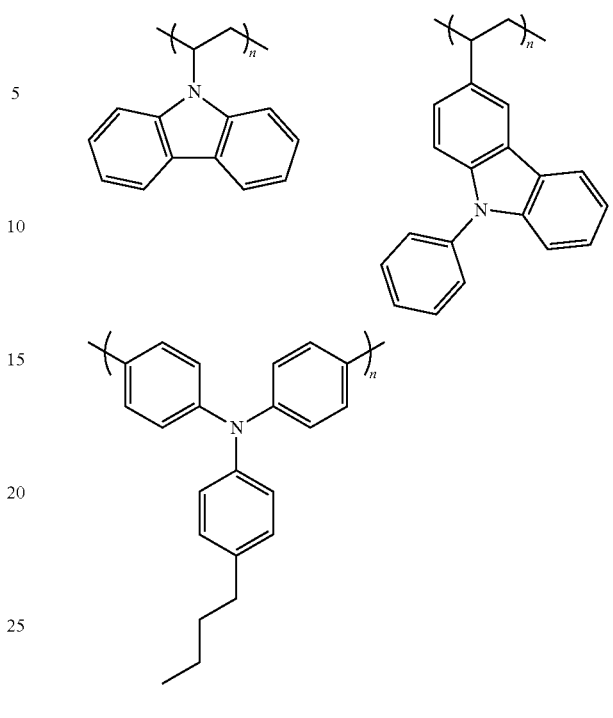

Electron Transporting Layer

The electron transporting layer comprises an electron transporting material. In some embodiments, the electron transporting layer is a single layer. In some embodiments, the electron transporting layer comprises a plurality of layer.

In some embodiments, the electron transporting material needs only to have a function of transporting electrons, which are injected from the cathode, to the light-emitting layer. In some embodiments, the electron transporting material also function as a hole barrier material. Examples of the electron transporting layer that may be used herein include but are not limited to a nitro-substituted fluorene derivative, a diphenylquinone derivative, a thiopyran dioxide derivative, carbodiimide, a fluorenylidene methane derivative, anthraquinodimethane, an anthrone derivatives, an azole derivative, an azine derivative, an oxadiazole derivative, or a combination thereof, or a polymer thereof. In some embodiments, the electron transporting material is a thiadiazole derivative, or a quinoxaline derivative. In some embodiments, the electron transporting material is a polymer material.

Specific preferred examples of a compound that can be used as an electron transporting material are shown below.

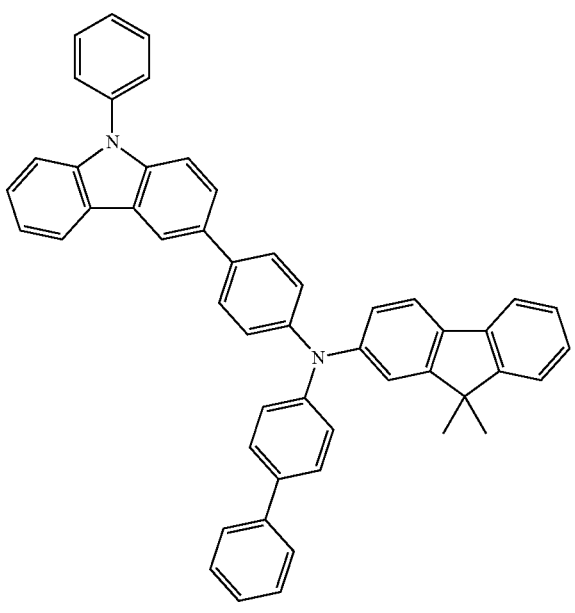

-continued

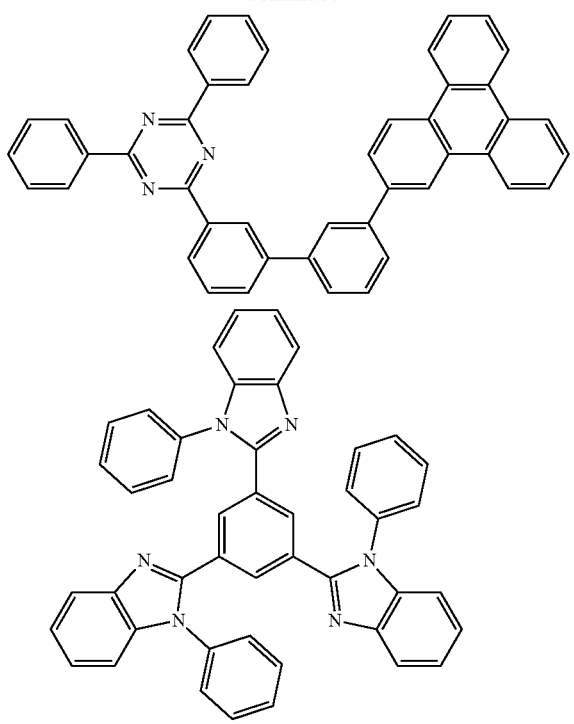
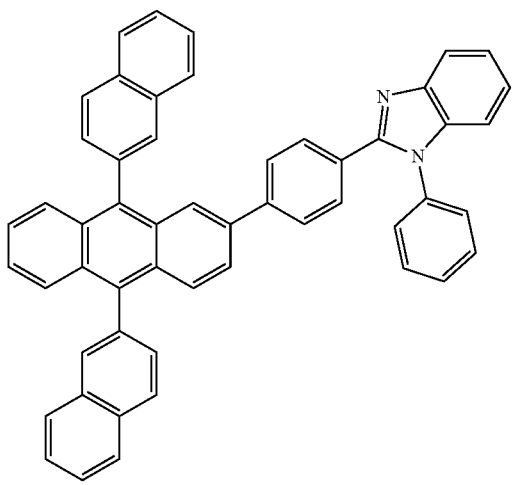
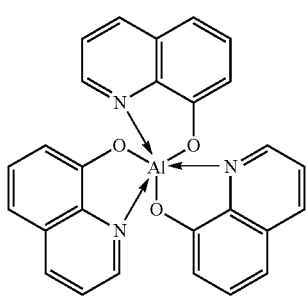

-continued

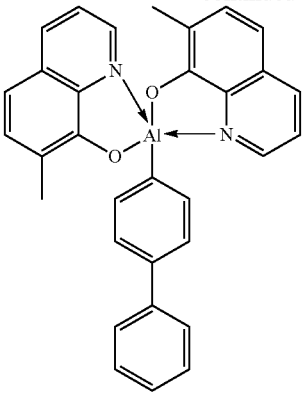
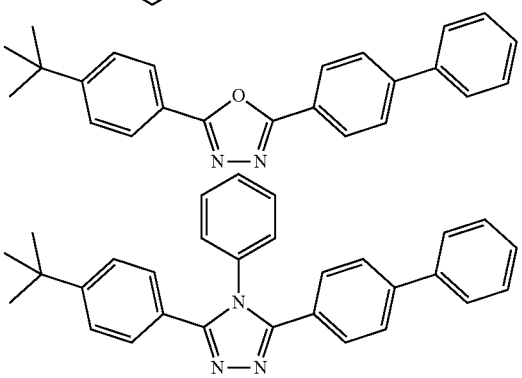

Preferred materials that can be used in an organic electroluminescence element are specifically exemplified above, but materials that can be used in the present invention are not limitedly construed by the compounds exemplified above. In addition, a compound exemplified as a material having a specific function can be diverted as a material having another function.

Devices

In some embodiments, the compounds represented by the formula (1) are incorporated into a device. For example, the device includes, but is not limited to an OLED bulb, an OLED lamp, a television screen, a computer monitor, a mobile phone, and a tablet.

In some embodiments, an electronic device comprises an OLED comprising an anode, a cathode, and at least one organic layer comprising a light emitting layer between the anode and the cathode, wherein the light emitting layer comprises a host material and a light emitting material.

In some embodiments, the light emitting layer of the OLED further comprises a fluorescent material which converts triplets to singlets.

In some embodiments, compositions described herein may be incorporated into various light-sensitive or light-activated devices, such as a OLEDs or photovoltaic devices. In some embodiments, the composition may be useful in facilitating charge transfer or energy transfer within a device and/or as a hole-transport material. The device may be, for example, an organic light-emitting diode (OLED), an organic integrated circuit (O—IC), an organic field-effect transistor (O-FET), an organic thin-film transistor (O-TFT), an organic light-emitting transistor (O-LET), an organic solar cell (O—SC), an organic optical detector, an organic photoreceptor, an organic field-quench device (O-FQD), a light-emitting electrochemical cell (LEC) or an organic laser diode (O-laser).

Bulbs or Lamps

In some embodiments, an electronic device comprises an OLED comprising an anode, a cathode, and at least one organic layer comprising a light emitting layer between the anode and the cathode, wherein the light emitting layer comprises a host material and a light emitting material; and an OLED driver circuit.

In some embodiments, a device comprises OLEDs that differ in color. In some embodiments, a device comprises an array comprising a combination of OLEDs. In some embodiments, the combination of OLEDs is a combination of three colors (e.g., RGB).

In some embodiments, the combination of OLEDs is a combination of colors that are not red, green, or blue (for example, orange and yellow green). In some embodiments, the combination of OLEDs is a combination of two, four, or more colors.

In some embodiments, a device is an OLED light comprising:
    a circuit board having a first side with a mounting surface and an opposing second side, and defining at least one aperture;
    at least one OLED on the mounting surface, the at least one OLED configured to emanate light, comprising:
        an anode, a cathode, and at least one organic layer comprising a light emitting layer between the anode and the cathode, wherein the light emitting layer comprises
        a host material;
        a compound of formula (I);
        wherein the compound of formula (I) is a light emitting material:
    a housing for the circuit board, and
    at least one connector arranged at an end of the housing, the housing and the connector defining a package adapted for installation in a light fixture.

In some embodiments, the OLED light comprises a plurality of OLEDs mounted on a circuit board such that light emanates in a plurality of directions. In some embodiments, a portion of the light emanated in a first direction is deflected to emanate in a second direction. In some embodiments, a reflector is used to deflect the light emanated in a first direction.

Displays or Screens

In some embodiments, the compounds of formula (1) can be used in a screen or a display. In some embodiments, the compounds of formula (1) are deposited onto a substrate using a process including, but not limited to, vacuum evaporation, deposition, vapor deposition, or chemical vapor deposition (CVD). In some embodiments, the substrate is a photoplate structure useful in a two-sided etch provides a unique aspect ratio pixel. The screen (which may also be referred to as a mask) is used in a process in the manufacturing of OLED displays. The corresponding artwork pattern design facilitates a very steep and narrow tie-bar between the pixels in the vertical direction and a large, sweeping bevel opening in the horizontal direction. This allows the close patterning of pixels needed for high definition displays while optimizing the chemical deposition onto a TFT backplane.

The internal pattering of the pixel allows the construction of a 3-dimensional pixel opening with varying aspect ratios in the horizontal and vertical directions. Additionally, the use of imaged "stripes" or halftone circles within the pixel area inhibits etching in specific areas until these specific patterns are undercut and fall off the substrate. At that point the entire pixel area is subjected to a similar etch rate but the depths are varying depending on the halftone pattern. Varying the size and spacing of the halftone pattern allows etching to be inhibited at different rates within the pixel allowing for a localized deeper etch needed to create steep vertical bevels.

A preferred material for the deposition mask is invar. Invar is a metal alloy that is cold rolled into long thin sheet in a steel mill. Invar cannot be electrodeposited onto a rotating mandrel as the nickel mask. A preferred and more cost feasible method for forming the open areas in the mask used for deposition is through a wet chemical etching.

In some embodiments, a screen or display pattern is a pixel matrix on a substrate. In some embodiments, a screen or display pattern is fabricated using lithography (e.g., photolithography and e-beam lithography). In some embodiments, a screen or display pattern is fabricated using a wet chemical etch. In further embodiments, a screen or display pattern is fabricated using plasma etching.

Methods of Manufacturing Devices Using the Disclosed Compounds

An OLED display is generally manufactured by forming a large mother panel and then cutting the mother panel in units of cell panels. In general, each of the cell panels on the mother panel is formed by forming a thin film transistor (TFT) including an active layer and a source/drain electrode on a base substrate, applying a planarization film to the TFT, and sequentially forming a pixel electrode, a light-emitting layer, a counter electrode, and an encapsulation layer, and then is cut from the mother panel.

An OLED display is generally manufactured by forming a large mother panel and then cutting the mother panel in units of cell panels. In general, each of the cell panels on the mother panel is formed by forming a thin film transistor (TFT) including an active layer and a source/drain electrode on a base substrate, applying a planarization film to the TFT, and sequentially forming a pixel electrode, a light-emitting layer, a counter electrode, and an encapsulation layer, and then is cut from the mother panel.

In another aspect, provided herein is a method of manufacturing an organic light-emitting diode (OLED) display, the method comprising:
    forming a barrier layer on a base substrate of a mother panel;
    forming a plurality of display units in units of cell panels on the barrier layer;
    forming an encapsulation layer on each of the display units of the cell panels;
    applying an organic film to an interface portion between the cell panels.

In some embodiments, the barrier layer is an inorganic film formed of, for example, SiNx, and an edge portion of the barrier layer is covered with an organic film formed of polyimide or acryl. In some embodiments, the organic film helps the mother panel to be softly cut in units of the cell panel.

In some embodiments, the thin film transistor (TFT) layer includes a light-emitting layer, a gate electrode, and a source/drain electrode. Each of the plurality of display units may include a thin film transistor (TFT) layer, a planarization film formed on the TFT layer, and a light-emitting unit formed on the planarization film, wherein the organic film applied to the interface portion is formed of a same material as a material of the planarization film and is formed at a same time as the planarization film is formed. In some embodiments, a light-emitting unit is connected to the TFT layer with a passivation layer and a planarization film therebetween and an encapsulation layer that covers and protects the light-emitting unit. In some embodiments of the method of manufacturing, the organic film contacts neither the display units nor the encapsulation layer.

Each of the organic film and the planarization film may include any one of polyimide and acryl. In some embodiments, the barrier layer may be an inorganic film. In some embodiments, the base substrate may be formed of polyimide. The method may further include, before the forming of the barrier layer on one surface of the base substrate formed of polyimide, attaching a carrier substrate formed of a glass material to another surface of the base substrate, and before the cutting along the interface portion, separating the carrier substrate from the base substrate. In some embodiments, the OLED display is a flexible display.

In some embodiments, the passivation layer is an organic film disposed on the TFT layer to cover the TFT layer. In some embodiments, the planarization film is an organic film formed on the passivation layer. In some embodiments, the planarization film is formed of polyimide or acryl, like the organic film formed on the edge portion of the barrier layer. In some embodiments, the planarization film and the organic film are simultaneously formed when the OLED display is manufactured. In some embodiments, the organic film may be formed on the edge portion of the barrier layer such that a portion of the organic film directly contacts the base substrate and a remaining portion of the organic film contacts the barrier layer w % bile surrounding the edge portion of the barrier layer.

In some embodiments, the light-emitting layer includes a pixel electrode, a counter electrode, and an organic light-emitting layer disposed between the pixel electrode and the counter electrode. In some embodiments, the pixel electrode is connected to the source/drain electrode of the TFT layer.

In some embodiments, when a voltage is applied to the pixel electrode through the TFT layer, an appropriate voltage is formed between the pixel electrode and the counter electrode, and thus the organic light-emitting layer emits light, thereby forming an image. Hereinafter, an image forming unit including the TFT layer and the light-emitting unit is referred to as a display unit.

In some embodiments, the encapsulation layer that covers the display unit and prevents penetration of external moisture may be formed to have a thin film encapsulation structure in which an organic film and an inorganic film are alternately stacked. In some embodiments, the encapsulation layer has a thin film encapsulation structure in which a plurality of thin films are stacked. In some embodiments, the organic film applied to the interface portion is spaced apart from each of the plurality of display units. In some embodiments, the organic film is formed such that a portion of the organic film directly contacts the base substrate and a remaining portion of the organic film contacts the barrier layer while surrounding an edge portion of the barrier layer.

In one embodiment, the OLED display is flexible and uses the soft base substrate formed of polyimide. In some embodiments, the base substrate is formed on a carrier substrate formed of a glass material, and then the carrier substrate is separated.

In some embodiments, the barrier layer is formed on a surface of the base substrate opposite to the carrier substrate. In one embodiment, the barrier layer is patterned according to a size of each of the cell panels. For example, while the base substrate is formed over the entire surface of a mother panel, the barrier layer is formed according to a size of each of the cell panels, and thus a groove is formed at an interface portion between the barrier layers of the cell panels. Each of the cell panels can be cut along the groove.

In some embodiments, the method of manufacture further comprises cutting along the interface portion, wherein a groove is formed in the barrier layer, wherein at least a portion of the organic film is formed in the groove, and wherein the groove does not penetrate into the base substrate. In some embodiments, the TFT layer of each of the cell panels is formed, and the passivation layer which is an inorganic film and the planarization film which is an organic film are disposed on the TFT layer to cover the TFT layer. At the same time as the planarization film formed of, for example, polyimide or acryl is formed, the groove at the interface portion is covered with the organic film formed of, for example, polyimide or acryl. This is to prevent cracks from occurring by allowing the organic film to absorb an impact generated when each of the cell panels is cut along the groove at the interface portion. That is, if the entire barrier layer is entirely exposed without the organic film, an impact generated when each of the cell panels is cut along the groove at the interface portion is transferred to the barrier layer, thereby increasing the risk of cracks. However, in one embodiment, since the groove at the interface portion between the barrier layers is covered with the organic film and the organic film absorbs an impact that would otherwise be transferred to the barrier layer, each of the cell panels may be softly cut and cracks may be prevented from occurring in the barrier layer. In one embodiment, the organic film covering the groove at the interface portion and the planarization film are spaced apart from each other. For example, if the organic film and the planarization film are connected to each other as one layer, since external moisture may penetrate into the display unit through the planarization film and a portion where the organic film remains, the organic film and the planarization film are spaced apart from each other such that the organic film is spaced apart from the display unit.

In some embodiments, the display unit is formed by forming the light-emitting unit, and the encapsulation layer is disposed on the display unit to cover the display unit. As such, once the mother panel is completely manufactured, the carrier substrate that supports the base substrate is separated from the base substrate. In some embodiments, when a laser beam is emitted toward the carrier substrate, the carrier substrate is separated from the base substrate due to a difference in a thermal expansion coefficient between the carrier substrate and the base substrate.

In some embodiments, the mother panel is cut in units of the cell panels. In some embodiments, the mother panel is cut along an interface portion between the cell panels by using a cutter. In some embodiments, since the groove at the interface portion along which the mother panel is cut is covered with the organic film, the organic film absorbs an impact during the cutting. In some embodiments, cracks may be prevented from occurring in the barrier layer during the cutting.

In some embodiments, the methods reduce a defect rate of a product and stabilize its quality.

Another aspect is an OLED display including: a barrier layer that is formed on a base substrate; a display unit that is formed on the barrier layer; an encapsulation layer that is formed on the display unit: and an organic film that is applied to an edge portion of the barrier layer.

<Definitions>

Unless otherwise defined herein, scientific and technical terms used in this application shall have the meanings that are commonly understood by those of ordinary skill in the art. Generally, nomenclature used in connection with, and techniques of, chemistry described herein, are those well-known and commonly used in the art.

The term "alkoxy" refers to an alkyl group, having an oxygen attached thereto. Representative alkoxy groups include methoxy, trifluoromethoxy, ethoxy, propoxy, tert-butoxy and the like.

The term "alkenyl", as used herein, refers to an aliphatic group comprising at least one double bond and is intended to include both "unsubstituted alkenyls" and "substituted alkenyls", the latter of which refers to alkenyl moieties having substituents replacing a hydrogen on one or more carbons of the alkenyl group. Typically, a straight chained or branched alkenyl group has from 1 to about 20 carbon atoms, preferably from 1 to about 10 unless otherwise defined. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group is a straight chained or branched non-aromatic hydrocarbon which is completely saturated. Typically, a straight chained or branched alkyl group has from 1 to about 20 carbon atoms, preferably from 1 to about 10 unless otherwise defined. In some embodiments, the alkyl group has from 1 to 8 carbon atoms, from 1 to 6 carbon atoms, from 1 to 4 carbon atoms, or from 1 to 3 carbon atoms. Examples of straight chained and branched alkyl groups include methyl, ethyl, n-propyl, iso-propyl, n-butyl, sec-butyl, tert-butyl, pentyl, hexyl, pentyl and octyl.

Moreover, the term "alkyl" as used throughout the specification, examples, and claims is intended to include both "unsubstituted alkyls" and "substituted alkyls", the latter of which refers to alkyl moieties having substituents replacing a hydrogen on one or more substitutable carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic orheteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters). —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkynyl", as used herein, refers to an aliphatic group comprising at least one triple bond and is intended to include both "unsubstituted alkynyls" and "substituted alkynyls", the latter of which refers to alkynyl moieties having substituents replacing a hydrogen on one or more carbons of the alkynyl group. Typically, a straight chained or branched alkynyl group has from 1 to about 20 carbon atoms, preferably from 1 to about 10 unless otherwise defined. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The terms "amine" and "amino" are art-recognized and refer to both unsubstituted and substituted amines and salts thereof, e.g., a moiety that can be represented by

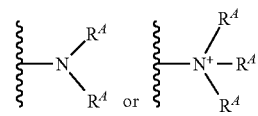

wherein each $R^A$ independently represents a hydrogen or a hydrocarbyl group, or two $R^A$ are taken together with the N atom to which they are attached complete a heterocycle having from 4 to 8 atoms in the ring structure.

The term "aryl" as used herein include substituted or unsubstituted single-ring aromatic groups in which each atom of the ring is carbon. Preferably the ring is a 6- or 20-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "halo" and "halogen" as used herein means halogen and includes chloro, fluoro, bromo, and iodo.

The terms "heteroaryl" and "hetaryl" include substituted or unsubstituted aromatic single ring structures, preferably 5- to 20-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 20-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Moieties that may be substituted can include any appropriate substituents described herein, for example, acyl, acylamino, acyloxy, alkoxy, alkoxyalkyl, alkenyl, alkyl, alkylamino, alkylthio, arylthio, alkynyl, amide, amino, aminoalkyl, aralkyl, carbamate, carbocyclyl, cycloalkyl, carbocyclylalkyl, carbonate, ester, ether, heteroaralkyl, heterocyclyl, heterocyclylalkyl, hydrocarbyl, silyl, sulfone, or thioether. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In various embodiments, compounds of this invention have an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof.

The term "compound." when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

EXAMPLES

Characteristics of the present invention will be described more specifically below with reference to examples. Materials, details and procedures of treatments, and the like shown below can be appropriately modified without departing from the gist of the present invention. Thus, the scope of the present invention is not to be limitedly construed by specific examples shown below. Note that evaluation of luminescent characteristics is performed by using a source meter (2400 series, manufactured by Keithley), a semiconductor parameter analyzer (E5273A, manufactured by Agilent Technologies Japan, Ltd.), an optical power meter (1930C, manufactured by Newport Corporation), an optical spectrometer (USB2000, manufactured by Ocean Optics, Inc.), a spectroradiometer (SR-3, manufactured by TOPCON CORPORATION), and a streak camera (model C4334, manufactured by Hamamatsu Photonics K.K.).

(Durability Test 1 of Blue Light Emitting Element)

As the first compound, any one selected from the compound 20, PYD2Cz, and Hosts 2 to 4, 6, and 7 was adopted, and as the second compound, T58 which is a blue delayed fluorescent material was adopted to perform a durability test of a blue light emitting element.

The blue light emitting element was produced so that the contents of the first compound and the second compound in a light emitting layer were 70% by mass and 30% by mass, respectively.

On a glass substrate having an indium-tin oxide (ITO) anode having a film thickness of 50 nm formed thereon, thin films were laminated by a vacuum deposition method at a degree of vacuum of $5.0 \times 10^{-5}$ Pa. First, on the ITO, HAT-CN was formed into a thickness of 10 nm, NPD was formed thereon into a thickness of 30 nm. Next, Tris-PCz was formed into a thickness of 10 nm, and PYD2Cz was formed thereon into a thickness of 5 nm. Next, the first compound and the second compound were co-deposited from different evaporation sources to form a layer having a thickness of 30 nm, thereby producing a light emitting layer. Next, SF3-TRZ was formed into a thickness of 10 nm, and then, Liq and SF3-TRZ were co-deposited from different evaporation sources to form a layer having a thickness of 30 nm. The contents of Liq and SF3-TRZ in this layer were 30% by mass and 70% by mass, respectively. In addition, Liq was formed into a thickness of 2 nm and subsequently, aluminum (Al) was deposited into a thickness of 100 nm, thereby forming a cathode. Thus, an organic electroluminescence element (EL element) was produced.

A time period until the intensity of emission of the blue light emitting element allowed to emit light at 1000 cd/m$^2$ reached 95% of the initial intensity was measured and defined as LT95. FIG. 2 shows a graph of a relation between the PBHT value of the first compound and the measurement result of the LT95. In the graph of FIG. 2, the LT95 of the HOST 3 was taken as 1. As is apparent from FIG. 2, it was found that a larger PBHT value tends to provide a longer LT95. In particular, for the element produced by using the compound 20 of the present invention which had the largest PBHT value, a LT95 that was 7.63 times longer than that of the element produced by using the Host 3 was observed, and thus, the element exhibited a good performance.

Each blue light emitting element was produced according to the above procedure except for using each of the compounds 13 to 19 and 21 to 26 as the first compound, and LT95 was measured. Then, a LT95 further longer than that of a blue light emitting element produced by using PYD2Cz (PBHT value was 0.671) as the first compound is observed.

(Durability Test 2 of Blue Light Emitting Element)

A durability test of a blue light emitting element was performed according to the same procedure as above except for using the compound 20 as the first compound, T58 as the second compound, and T80 as the third compound so that the contents of the first compound, the second compound, and the third compound in a light emitting layer were 69% by mass, 30% by mas, and 1% by mass, respectively. Then, a good LT95 was observed as with the above case.

(Durability Test 1 of Green Light Emitting Element)

Any one selected from Hosts 1 to 5 and the compound 13 was adopted as the first compound and a compound T8 (4CzIPN) which is a green delayed fluorescent material was adopted as the second compound to produce a green light emitting element, and the time period until the intensity of emission of the green light emitting element allowed to emit light at 12.5 mA/cm$^2$ was 95% of the initial intensity was measured and taken as LT95.

The green light emitting element was produced by laminating, on a glass substrate having an anode of indium tin oxide (ITO) having a film thickness of 50 nm formed thereon, thin films by a vacuum deposition method at a degree of vacuum of $5.0 \times 10^{-5}$ Pa. First, on the ITO, NPD (95% by mass) and H11 (5% by mass) were formed into a thickness of 5 nm, and NPD was formed thereon into a thickness of 60 nm. Next, PTCz was formed into a thickness of 10 nm. Next, the first compound (65% by mass) and the second compound (35% by mass) were co-deposited from different evaporation sources to form a layer of a thickness of 40 nm, thus producing a light emitting layer. Next, SF3-TRZ was formed into a thickness of 10 nm, and then, Liq (30% by mass) and SF3-TRZ (70% by mass) were co-deposited from different evaporation sources to form a layer of a thickness of 30 nm. Furthermore, Liq was formed into a thickness of 2 nm, and subsequently, aluminum (Al) was deposited into a thickness of 100 nm, thereby forming a cathode. Thus, an organic electroluminescence element (EL element) was produced.

FIG. 3 shows a graph of a relation between the PBHT value of the first compound and the measurement result of LT95. In the graph of FIG. 3, the LT95 of the HOST 3 was taken as 1. As is appearance from FIG. 3, it was found that a larger PBHT value tends to provide a longer LT95. In addition, it was found that a particularly longer LT95 was observed for a compound having PBHT more than 0.730 which was a PBHT value of the HOST 1. Furthermore, each green light emitting element was produced according to the same procedure as above except for using each of the compounds 14 to 26 as the first compound, and LT95 was measured. Then, a LT95 longer than that of the green light emitting element produced by using the Host 1 as the first compound is observed.

(Durability Test 2 of Green Light Emitting Element)

A green element was produced in the same manner as above except for selecting any one selected from the compound 20, the compound 21, and the compound 23 as the first compound and using T69 as the second compound so that the contents of the first compound and the second compound in a light emitting layer were 65% by mass and 35% by mass, respectively. Then, a good LT95 was observed as with the above case.

(Durability Test 3 of Green Light Emitting Element)

A durability test of a green light emitting element was performed according to the same procedure as above except for selecting any one selected from the compound 20, the compound 21, and the compound 23 as the first compound and using T67 as the second compound so that the contents of the first compound and the second compound in a light emitting layer were 65% by mass and 35% by mass, respectively. Then, a good LT95 was observed as with the above case.

Host 1
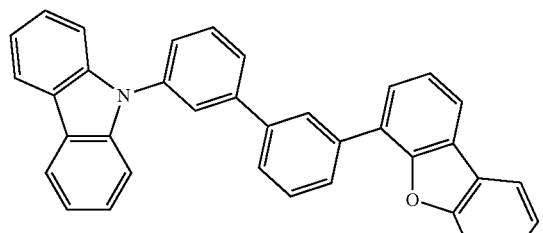
Host 2
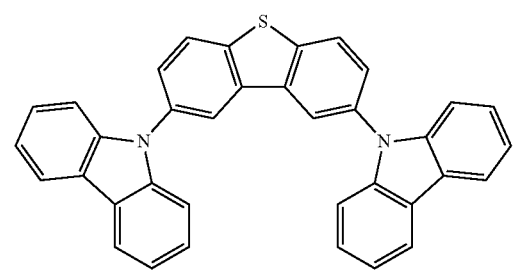
Host 3
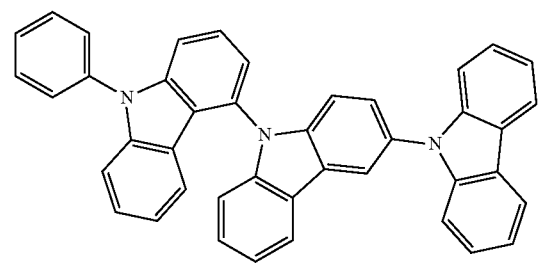
Host 4
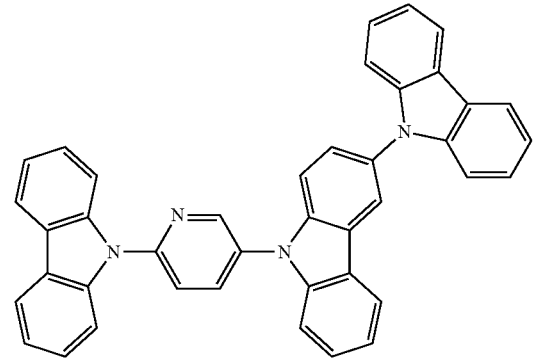
Host 5
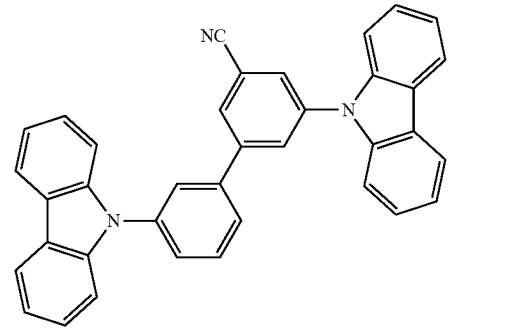
Host 6
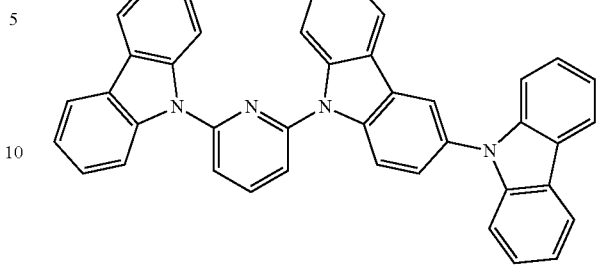
Host 7
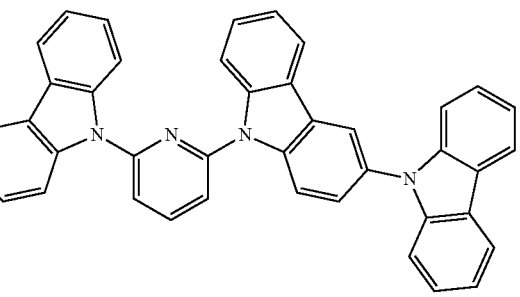
HAT-CN
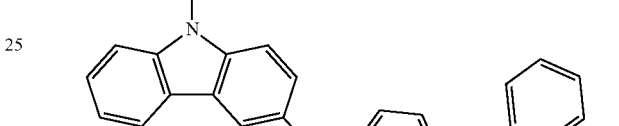
NPD
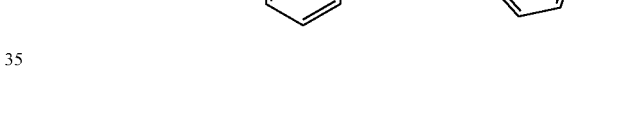

TrisPCz

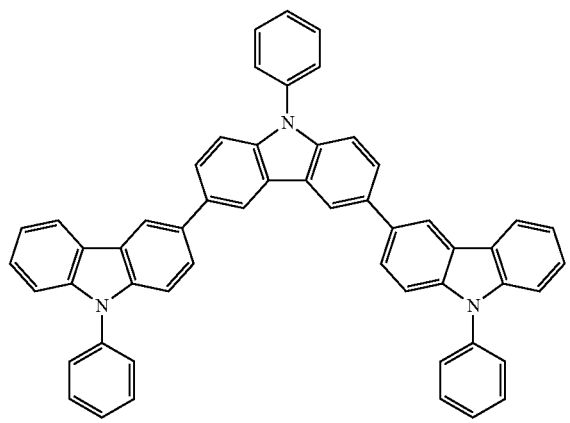

PYD2Cz

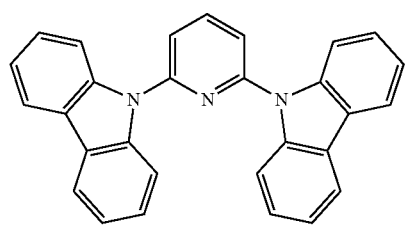

SF3-TRZ

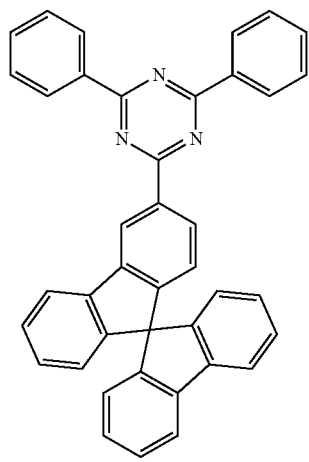

Liq

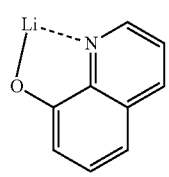

HI1

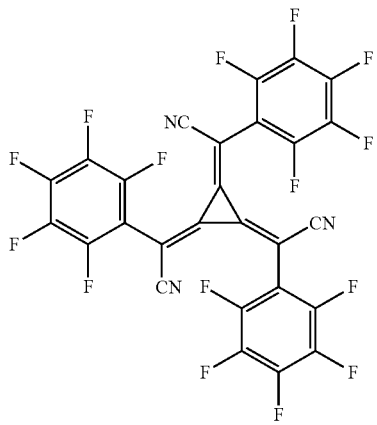

PTCz

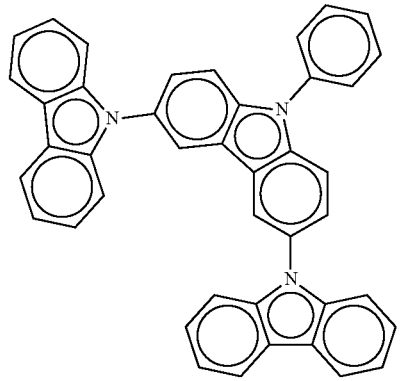

INDUSTRIAL APPLICABILITY OF INVENTION

When a composition satisfying the conditions of the present invention is used, an organic light emitting element having excellent durability can be provided. In addition, when the method of the present invention is used, a composition useful for producing an organic light emitting element having excellent durability can be conveniently designed. Thus, the present invention has high industrial applicability.

CITATION LIST

1: Substrate
2: Anode
3: Hole injecting layer
4: Hole transporting layer
5: Light emitting layer
6: Electron transporting layer
7: Cathode

The invention claimed is:

1. A composition consisting of both a first compound satisfying the following expression (1a) and a second compound satisfying the following expression (2b), or consisting of a first compound satisfying the following expression (1a), a second compound satisfying the following expression (2b) and a third compound that is a fluorescence material, the first compound and the second compound satisfying the following expression (A):

$$PBHT(1) > 0.830 \quad \text{expression (1a)}$$

$$\Delta E_{ST}(2) < 0.20 \text{ eV} \quad \text{expression (2b)}$$

$$E_{S1}(1) > E_{S1}(2) \quad \text{expression (A)}$$

the first compound, the second compound and the third compound satisfying the following expression (B):

$$E_{S1}(1) > E_{S1}(2) > E_{S1}(3) \quad \text{expression (B)}$$

wherein PBHT(1) is a PBHT value of the first compound, $\Delta E_{ST}(2)$ is a difference between a lowest excited singlet energy level $E_{S1}(2)$ of the second compound and a lowest excited triplet energy level $E_{T1}(2)$ of the second compound, and $E_{S1}(1)$ is a lowest excited singlet energy level of the first compound, and $E_{S1}(3)$ is a lowest excited singlet energy level of the third compound.

2. The composition according to claim 1, wherein the first compound also satisfies the following expression (1c):

$$BDE(1) > 4.20 \text{ eV} \quad \text{expression (1c)}$$

wherein BDE(1) is a cation bond dissociation energy of the first compound.

3. The composition according to claim 1, wherein the second compound also satisfies the following expression (2a):

$$0.200 < PBHT(2) < 0.400 \quad \text{expression (2a)}$$

wherein PBHT(2) is a PBHT value of the second compound.

4. The composition according to claim 1, wherein the first compound also satisfies the following expression (1c) and the second compound also satisfies the following expression (2a):

$$BDE(1) > 4.20 \text{ eV} \quad \text{expression (1c)}$$

$$0.200 < PBHT(2) < 0.400 \quad \text{expression (2a)}$$

wherein BDE(1) is a cation bond dissociation energy of the first compound and PBHT(2) is a PBHT value of the second compound.

5. The composition according to claim 1, wherein the PBHT(1) is more than 0.910.

6. The composition according to claim 1, wherein the second compound satisfies the following expression (2d):

$$\tau_{DELAY} < 10 \text{ μs} \quad \text{expression (2d)}$$

wherein $\tau_{DELAY}$ is a delayed fluorescence lifetime of the second compound.

7. The composition according to claim 1, wherein the first compound has one or more structures selected from the group consisting of a triazine structure, a carbazole structure, a fulvalene structure, and a thiovalene structure.

8. The composition according to claim 1, wherein the first compound has at least one of a dibenzofuran structure and a dibenzothiophene structure.

9. The composition according to claim 8, wherein the first compound has a structure represented by the following the general formula (1):

General formula (1)

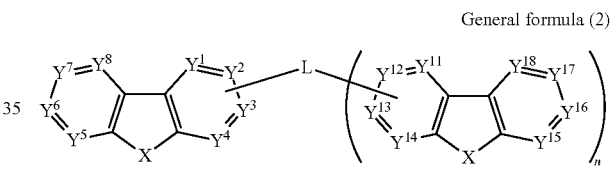

wherein multiple Xs each independently represent O or S, $Y^1$ to $Y^8$ and $Y^{11}$ to $Y^{18}$ each independently represent N or C—R wherein R represents a hydrogen atom, a substituent, or a direct bond to L, $Y^{21}$ to $Y^{28}$ each independently represent N or C—R' wherein R' represents a hydrogen atom or a substituent, L represents a (n+p+1)-valent conjugated linking group having at least one aromatic ring or heteroaromatic ring, n represents an integer of 0 or more, when n is 2 or more, multiple $Y^{11}$s to $Y^{18}$s may be the same as or different from each other, p represents an integer of 0 or more, when p is 2 or more, multiple $Y^{21}$s to $Y^{28}$s may be the same as or different from each other, and n+p is 1 or more.

10. The composition according to claim 8, wherein the first compound has a structure represented by the following general formula (2):

General formula (2)

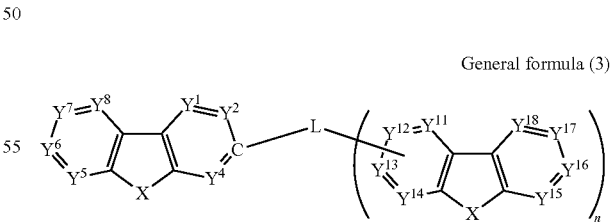

wherein multiple Xs each independently represent O or S, $Y^1$ to $Y^8$ and $Y^{11}$ to $Y^{18}$ each independently represent N or C—R wherein R represents a hydrogen atom, a substituent, or a direct bond to L, L represents a (n+1)-valent conjugated linking group containing at least one aromatic ring or heteroaromatic ring, n represents an integer of 1 or more, and when n is 2 or more, multiple $Y^{11}$s to $Y^{18}$s may be the same as or different from each other.

11. The composition according to claim 8, wherein the first compound has a structure represented by the following general formula (3):

General formula (3)

wherein multiple Xs each independently represent O or S, $Y^1, Y^2, Y^4$ to $Y^8$ and $Y^{11}$ to $Y^{18}$ each independently represent N or C—R wherein R represents a hydrogen atom, a substituent, or a direct bond to L, L represents a (n+1)-valent conjugated linking group containing at least one aromatic ring or heteroaromatic ring, n represents an integer of 2 or more, and multiple $Y^{11}$s to $Y^{18}$s may be the same as or different from each other.

12. The composition according to claim 8, wherein the first compound has a structure represented by the following general formula (4):

General formula (4)

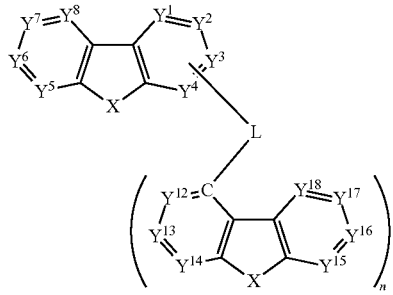

wherein multiple Xs each independently represent O or S, $Y^1$ to $Y^8$ and $Y^{12}$ to $Y^{18}$ each independently represent N or C—R wherein R represents a hydrogen atom, a substituent, or a direct bond to L, L represents a (n+1)-valent conjugated linking group containing at least one aromatic ring or heteroaromatic ring, n represents an integer of 2 or more, and multiple $Y^{11}$s to $Y^{18}$s may be the same as or different from each other.

13. The composition according to claim 8, wherein the first compound has a structure represented by the following general formula (5):

General formula (5)

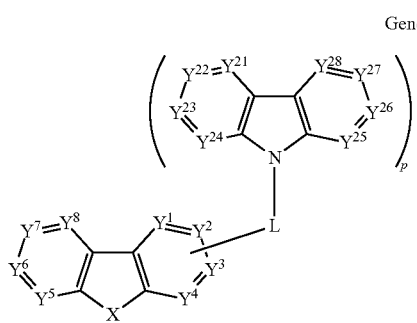

wherein X represents O or S, $Y^1$ to $Y^8$ each independently represent N or C—R wherein R represents a hydrogen atom, a substituent, or a direct bond to L, $Y^{21}$ to $Y^{28}$ each independently represent N or C—R' wherein R' represents a hydrogen atom or a substituent, L represents a (p+1)-valent conjugated linking group containing at least one aromatic ring or heteroaromatic ring, p represents an integer of 1 or more, and when p is 2 or more, multiple $Y^{21}$s to $Y^{28}$s may be the same as or different from each other.

14. The composition according to claim 9, wherein L has a structure having one or more rings linked, the rings being selected from the group consisting of a benzene ring and a pyridine ring.

15. The composition according to claim 9, wherein L comprises a 1,3-phenylene group or a 2,6-pyridylene group as a linking chain.

16. The composition according to claim 9, wherein L comprises a 1,4-phenylene group or a 2,6-pyridylene group as a linking chain.

17. The composition according to claim 9, wherein n is 2.

18. The composition according to claim 9, wherein R is a hydrogen atom or a substituted or unsubstituted aryl group.

19. The composition according to claim 1, wherein a content of the second compound is 0.01 to 70 parts by weight relative to 100 parts by weight of a content of the first compound.

20. The composition according to claim 1, wherein the third compound also satisfies the following expression (3b):

$$\Delta E_{ST}(3) < 0.20 \text{ eV} \qquad \text{expression(3b)}$$

wherein $\Delta E_{ST}(3)$ is a difference between the lowest excited singlet energy level $E_{S1}(3)$ of the third compound and a lowest excited triplet energy level $E_{T1}(3)$ of the third compound.

21. A film comprising the composition according to claim 1.

22. An organic light emitting element comprising the composition according to claim 1.

23. The organic light emitting element according to claim 22, which emits delayed fluorescence.

24. The organic light emitting element according to claim 22, which is an organic electroluminescence element.

25. The organic light emitting element according to claim 22, wherein the second compound emits light in the largest amount of all materials contained in the light emitting element.

26. The organic light emitting element according to claim 23, wherein the third compound emits light in the largest amount of all materials contained in the light emitting element.

27. The composition according to claim 1, wherein the first compound being represented by the following general formula (1) or (5):

General formula (1)

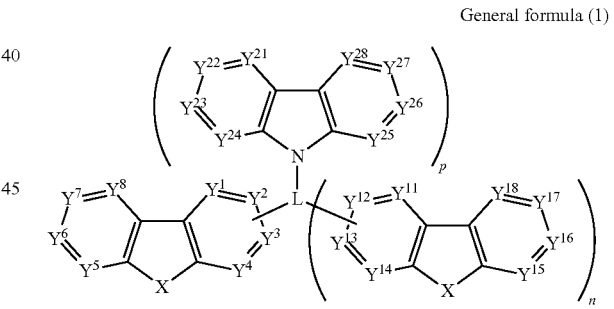

wherein multiple Xs each independently represent O or S, $Y^1$ to $Y^8$ and $Y^{11}$ to $Y^{18}$ each independently represent N or C—R wherein R represents a hydrogen atom, a substituent, or a direct bond to L, $Y^{21}$ to $Y^{28}$ each independently represent N or C—R' wherein R' represents a hydrogen atom or a substituent, L represents a (n+p+1)-valent conjugated linking group having at least one aromatic ring or heteroaromatic ring, n represents an integer of 1 or more, when n is 2 or more, multiple $Y^1$'s to $Y^{18}$s may be the same as or different from each other, p represents an integer of 1 or more, when p is 2 or more, multiple $Y^{21}$s to $Y^{28}$s may be the same as or different from each other, and n+p is 2 or more;

General formula (5)

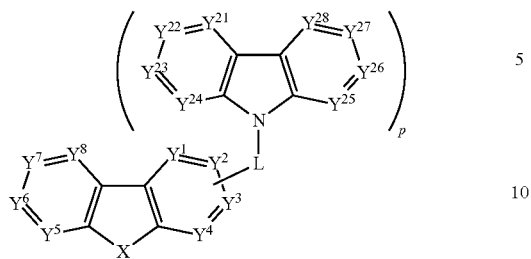

wherein X represents O or S, $Y^1$ to $Y^8$ each independently represent N or C—R wherein R represents a hydrogen atom, a substituent, or a direct bond to L, $Y^{21}$ to $Y^{28}$ each independently represent N or C—R' wherein R' represents a hydrogen atom or a substituent, L represents a (p+1)-valent conjugated linking group consisting of a monocyclic aromatic or monocyclic heteroaromatic ring, p represents an integer of 1 or more, and when p is 2 or more, multiple $Y^{21}$s to $Y^{28}$s may be the same as or different from each other.

* * * * *